(12) United States Patent
Clark et al.

(10) Patent No.: US 7,928,237 B2
(45) Date of Patent: Apr. 19, 2011

(54) FUSED RING AZADECALIN GLUCOCORTICOID RECEPTOR MODULATORS

(75) Inventors: Robin D. Clark, Kalaheo, HI (US); Nicholas C. Ray, Harlow (GB); Paul M. Blaney, Harlow (GB); Christopher A. Hurley, Harlow (GB); Karen Williams, Harlow (GB)

(73) Assignee: Corcept Therapeutics, Inc., Menlo Park, CA (US)

( * ) Notice: Subject to any disclaimer, the term of this patent is extended or adjusted under 35 U.S.C. 154(b) by 1014 days.

(21) Appl. No.: 10/591,884

(22) PCT Filed: Mar. 9, 2005

(86) PCT No.: PCT/US2005/008049
§ 371 (c)(1),
(2), (4) Date: May 7, 2007

(87) PCT Pub. No.: WO2005/087769
PCT Pub. Date: Sep. 22, 2005

(65) Prior Publication Data
US 2007/0281928 A1    Dec. 6, 2007

Related U.S. Application Data

(60) Provisional application No. 60/551,836, filed on Mar. 9, 2004.

(51) Int. Cl.
*C07D 487/04* (2006.01)
*C07D 471/04* (2006.01)
*A61K 31/437* (2006.01)

(52) U.S. Cl. .......................................... 546/83; 514/293
(58) Field of Classification Search .................... 546/83; 514/293
See application file for complete search history.

(56) References Cited

FOREIGN PATENT DOCUMENTS
EP        0375210 A1    6/1990

*Primary Examiner* — Rita J Desai
(74) *Attorney, Agent, or Firm* — Kilpatrick Townsend & Stockton LLP

(57) ABSTRACT

The present invention provides a novel class of fused ring azadecalin compounds and methods of using the compounds as glucocorticoid receptor modulators.

10 Claims, No Drawings

FUSED RING AZADECALIN GLUCOCORTICOID RECEPTOR MODULATORS

CROSS-REFERENCES TO RELATED APPLICATIONS

This application claims the benefit of U.S. Provisional Patent Application No. 60/551,836, filed Mar. 9, 2004, which is incorporated herein by reference in its entirety for all purposes.

BACKGROUND OF THE INVENTION

In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which differs in only the last fifteen amino acids. The two types of GR have high affinity for their specific ligands, and are considered to function through the same transduction pathways.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, block the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$ M (Cadepond (1997) *Annu. Rev. Med.* 48:129).

Patients with some forms of psychiatric illnesses have been found to have increased levels of cortisol (Krishnan (1992) *Prog. Neuro-Psychophannacol. & Biol. Psychiat.* 16:913-920). For example, some depressed individuals can be responsive to treatments which block the effect of cortisol, as by administering GR antagonists (Van Look (1995) *Human Reproduction Update* 1:19-34). In one study, a patient with depression secondary to Cushing's Syndrome (hyperadrenocorticism) was responsive to a high dose, up to 1400 mg per day, of GR antagonist mifepristone (Nieman (1985) *J. Clin Endocrinol. Metab.* 61:536). Another study which used mifepristone to treat Cushing's syndrome found that it improved the patients' conditions, including their psychiatric status (Chrousos, pp 273-284, In: Baulieu, ed. *The Antiprogestin Steroid RU 486 and Human Fertility Control*. Plenum Press, New York (1989), Sartor (1996) *Clin. Obstetrics and Gynecol.* 39:506-510).

Psychosis has also been associated with Cushing's syndrome (Gerson (1985) *Can. J. Psychiatry* 30:223-224; Saad (1984) *Am. J. Med.* 76:759-766). Mifepristone has been used to treat acute psychiatric disturbances secondary to Cushing's syndrome. One study showed that a relatively high dose of mifepristone (400 to 800 mg per day) was useful in rapidly reversing acute psychosis in patients with severe Cushing Syndrome due to adrenal cancers and ectopic secretion of ACTH from lung cancer (Van der Lely (1991) *Ann. Intern. Med.* 114:143; Van der Lely (1993) *Pharmacy World & Science* 15:89-90; Sartor (1996) supra).

A treatment for psychosis or the psychotic component of illnesses, such as psychotic major depression, has recently been discovered (Schatzberg et al., U.S. Pat. No. 6,150,349). The treatment includes administration of an amount of a glucocorticoid receptor antagonist effective to ameliorate the psychosis. The psychosis may also be associated with psychotic major depression, Alzheimer's Disease and cocaine addiction.

Thus, there exists a great need for a more effective and safer treatment for illnesses and conditions associated with the glucocorticoid receptors, including psychotic major depression. The present invention fulfills these and other needs.

SUMMARY OF THE INVENTION

In a first aspect, the present invention provides a compound having the formula:

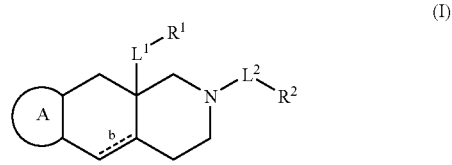

In Formula (I), $L^1$ and $L^2$ are independently selected from a bond, —O—, —S—, S(O)—, —S(O$_2$)—, —C(O)—, —C(O)O—, —C(O)NH—, substituted or unsubstituted alkylene, and substituted or unsubstituted heteroalkylene.

The dashed line b is optionally a bond.

The ring A is selected from substituted or unsubstituted cycloalkyl, substituted or unsubstituted heterocycloalkyl, substituted or unsubstituted aryl and substituted or unsubstituted heteroaryl.

$R^1$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$^{1A}$, —NR$^{1C}$R$^{1D}$, C(O)NR$^{1C}$R$^{1D}$, C(O)OR$^{1A}$. R$^{1A}$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{1C}$ and $R^{1D}$ are selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Alternatively $R^{1C}$ and $R^{1D}$ may be joined together with the nitrogen atom to which they are attached to form a substituted or unsubstituted ring optionally containing a second heteroatom selected from O, N or S.

$R^2$ is selected from substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —S(O$_2$)R$^{2A}$, —S(O$_2$)NR$^{2B}$R$^{2C}$, =NOR$^{2D}$. R$^{2A}$, R$^{2B}$, R$^{2C}$, and R$^{2D}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In another aspect, the present invention provides methods of treating a disorder or condition through modulating a glucocorticoid receptor. The method includes administering to a subject in need of such treatment, an effective amount of the compound of the present invention.

In another aspect, the present invention provides methods of treating a disorder or condition through antagonizing a glucocorticoid receptor. The method includes administering to a subject in need of such treatment, an effective amount of the compound of the present invention.

In another aspect, the present invention provides methods of modulating a glucocorticoid receptor including the steps of contacting a glucocorticoid receptor with an effective amount of the compound of the present invention and detecting a change in the activity of the glucocorticoid receptor.

In another aspect, the present invention provides a pharmaceutical composition including a pharmaceutically acceptable excipient and the compound of the present invention.

DETAILED DESCRIPTION OF THE INVENTION

Abbreviations and Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having five or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—OH, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —S(O)$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). Likewise, the term "heteroarylalkyl" is meant to include those radicals in which a heteroaryl group is attached to an alkyl group.

The term "oxo" as used herein means an oxygen that is double bonded to a carbon atom.

Each of the above terms (e.g., "alkyl," "heteroalkyl," "aryl" and "heteroaryl") are meant to include both substituted and unsubstituted forms of the indicated radical. Examples of substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NR(SO$_2$)R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NR(SO$_2$)R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Where two substituents are "optionally joined together to form a ring," the two substituents are covalently bonded together with the atom or atoms to which the two substituents are joined to form a substituted or unsubstituted aryl, a substituted or unsubstituted heteroaryl, a substituted or unsubstituted cycloalkyl, or a substituted or unsubstituted heterocycloalkyl ring.

The term "cortisol" refers to a family of compositions also referred to as hydrocortisone, and any synthetic or natural analogues thereof.

The term "glucocorticoid receptor" ("GR") refers to a family of intracellular receptors also referred to as the cortisol receptor, which specifically bind to cortisol and/or cortisol analogs (e.g. dexamethasone). The term includes isoforms of GR, recombinant GR and mutated GR.

The term "glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," we intend the drug to preferentially bind to the GR rather than another nuclear receptors, such as mineralocorticoid receptor (MR) or progesterone receptor (PR).

"Fused ring azadecalin," as used herein, means a glucocorticoid receptor modulator as described by any of the Formulae (I)-(XI) below. A fused ring azadecalin compound may also be referred to herein as a "compound of the present invention."

The term "treating" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the methods of the invention successfully treat a patient's delirium by decreasing the incidence of disturbances in consciousness or cognition.

An "additional ring heteroatom" refers to a heteroatom that forms part of a substituted or unsubstituted ring (e.g., a heterocycloalkyl or heteroaryl) that is not the point of attachment of the ring toward the azadecalin core. The azadecalin core is the fused ring portion of the compound of Formula (I), excluding ring A.

A "substituent group," as used herein, means a group selected from the following moieties:

(A) —OH, —NH$_2$, —SH, —CN, —CF$_3$, —COOH, —C(O)NH$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —COOH, —C(O)NH$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —COOH, —C(O)NH$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a "substituent group" as defined above, wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein means a "substituent group" as defined above, wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)— or (S)— or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)— and (S)—, or (D)- and (L)-isomers may be prepared using chiral synthons or chiral reagents, or resolved using conventional techniques.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or. $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The terms "a," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substitutent group, the compound is substituted with at least one substituent group, wherein each substitutent group is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

The terms "treating" or "treatment" in reference to a particular disease includes prevention of the disease.

DESCRIPTION OF THE EMBODIMENTS

I. Glucocorticoid Receptor Modulators

It has now been discovered that fused ring azadecalin compounds are potent modulators of glucocorticoid receptors ("GR"). GR modulators typically act as agonists, partial agonists or antagonists of GR thereby affecting a wide array of cellular functions, physiological functions and disease states.

Cortisol acts by binding to an intracellular glucocorticoid receptor. In humans, glucocorticoid receptors are present in two forms: a ligand-binding GR-alpha of 777 amino acids; and, a GR-beta isoform that differs in only the last fifteen amino acids. The two types of GR have high affinity for their specific ligands, and are considered to function through the same transduction pathways.

GR modulators are typically efficacious agents for influencing important cellular and physiological functions such as carbohydrate, protein and lipid metabolism; electrolyte and water balance; and functions of the cardiovascular system, kidney, central nervous system, immune system, skeletal muscle system and other organ and tissue systems. GR modulators may also affect a wide variety of disease states, such as obesity, diabetes, cardiovascular disease, hypertension, Syndrome X, depression, anxiety, glaucoma, human immunodeficiency virus (HIV) or acquired immunodeficiency syndrome (AIDS), neurodegeneration (e.g. Alzheimer's disease and Parkinson's disease), cognition enhancement, Cushing's Syndrome, Addison's Disease, osteoporosis, frailty, inflammatory diseases (e.g., osteoarthritis, rheumatoid arthritis, asthma and rhinitis), adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism, and muscle frailty.

In a first aspect, the present invention provides a compound having the formula:

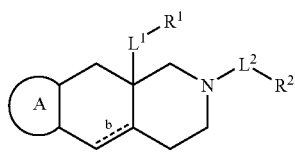

In Formula (I), $L^1$ and $L^2$ are independently selected from a bond, —O—, —S—, S(O)—, —S(O$_2$)—, —C(O)—, —C(O)O—, —C(O)NH—, substituted or unsubstituted alkylene, and substituted or unsubstituted heteroalkylene.

The dashed line b is optionally a bond.

The ring A is selected from substituted or unsubstituted cycloalkyl, substituted or unsubstituted heterocycloalkyl, substituted or unsubstituted aryl, and substituted or unsubstituted heteroaryl.

$R^1$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —OR$^{1A}$, —NR$^{1C}$R$^{1D}$, —C(O)NR$^{1C}$R$^{1D}$, —C(O)OR$^{1A}$. $R^{1A}$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{1C}$ and $R^{1D}$ are selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Alternatively, $R^{1C}$ and $R^{1D}$ may be joined together with the nitrogen atom to which they are attached to form a substituted or unsubstituted ring optionally containing a second heteroatom selected from O, N or S. In some embodiments, the substituted or unsubstituted ring is a 4 to 8 membered ring and the second heteroatom is a nitrogen. In other embodiments, where $R^1$ is a substituted or unsubstituted alkyl, the alkyl moiety is a substituted or unsubstituted $C_1$-$C_{20}$ alkyl (e.g. a $C_6$-$C_{20}$ alkyl).

$R^2$ is selected from substituted or unsubstituted alkyl substituted or unsubstituted heteroalkyl, substituted or unsubstituted cycloalkyl, substituted or unsubstituted heterocycloalkyl, substituted or unsubstituted aryl, substituted or unsubstituted heteroaryl, —S(O$_2$)R$^{2A}$, —S(O$_2$)NR$^{2B}$R$^{2C}$, =NOR$^{2D}$. $R^{2A}$, $R^{2B}$, $R^{2C}$, or $R^{2D}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

$L^1$ and $L^2$ may also be independently selected from a bond, substituted or unsubstituted ($C_1$-$C_6$)alkylene, and substituted or unsubstituted 2 to 5 membered heteroalkylene. In a related embodiment, $L^1$ and $L^2$ are independently selected from a bond and —C(O)—. In another related embodiment, $L^1$ and $L^2$ are independently selected from a bond and unsubstituted ($C_1$-$C_6$) alkylene.

In some embodiments, the ring A is selected from substituted or unsubstituted 5 to 6 membered heterocycloalkyl, and substituted or unsubstituted heteroaryl. A may also be selected from unsubstituted 5 to 6 membered heterocycloalkyl including at least one heteroatom selected from N, O and S; substituted 5 to 6 membered heterocycloalkyl having 1 to 3 substituents and at least one ring heteroatom selected from N, O and S; unsubstituted aryl having at least one heteroatom selected from N, O and S; and substituted aryl having 1 to 3 substituents and at least one ring heteroatom selected from N, O and S.

A variety of heterocycloalkyl groups are useful as A ring groups, including substituted or unsubstituted pyrrolidinyl, substituted or unsubstituted pyrrolyl, substituted or unsubstituted pyrazolyl, substituted or unsubstituted imidazolyl, substituted or unsubstituted furanyl, substituted or unsubstituted oxazolyl, substituted or unsubstituted isoxazolyl, substituted or unsubstituted thienyl, substituted or unsubstituted thiazolyl, substituted or unsubstituted isothiazolyl, substituted or unsubstituted pyridinyl, substituted or unsubstituted pyrimidinyl, substituted or unsubstituted pyrazinyl, and substituted or unsubstituted pyrimidinyl and substituted or unsubstituted piperidinyl. In some embodiments, A is a substituted or unsubstituted pyrazolyl.

Where A is substituted, the substituent may be selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —NR$^{3A}$R$^{3B}$, and —OR$^{3C}$. The ring A substituent may also be selected from hydrogen, substituted or unsubstituted ($C_1$-$C_{10}$) alkyl, substituted or unsubstituted 2-10 membered heteroalkyl, substituted or unsubstituted ($C_3$-$C_7$) cycloalkyl, substituted or unsubstituted 3-7 membered heterocycloalkyl, substituted or unsubstituted aryl, and substituted or unsubstituted heteroaryl, —NR$^{3A}$R$^{3B}$, and —OR$^{3C}$. The ring A substituent may also be selected from hydrogen, substituted or unsubstituted alkyl, substituted or unsubstituted heteroaryl, substituted or unsubstituted aryl, —NR$^{3A}$R$^{3B}$, and —OR$^{3C}$. $R^{3A}$ and $R^{3B}$ are independently selected from hydrogen, substituted or unsubstituted alkyl, substituted or unsubstituted heteroalkyl, substituted or unsubstituted heterocycloalkyl, and substituted or unsubstituted heteroaryl. $R^{3A}$ and $R^{3B}$ are optionally joined to form a substituted or unsubstituted ring with the nitrogen to which they are attached, wherein the ring optionally comprises an additional ring heteroatom. $R^{3C}$ is a selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

$R^{3A}$, $R^{3B}$, and $R^{3C}$ may be selected from substituted or unsubstituted ($C_1$-$C_{10}$) alkyl, substituted or unsubstituted 2-10 membered heteroalkyl, substituted or unsubstituted ($C_3$-$C_7$) cycloalkyl, substituted or unsubstituted 3-7 membered heterocycloalkyl, substituted or unsubstituted aryl, and substituted or unsubstituted heteroaryl.

In a related embodiment, A is substituted with at least two substituents. The first substituent is selected from hydrogen, substituted or unsubstituted alkyl, substituted or unsubstituted heteroaryl, substituted or unsubstituted aryl, —NR$^{3A}$R$^{3B}$, and —OR$^{3C}$. The second substituent is selected from hydrogen, substituted or unsubstituted alkyl, substituted or unsubstituted aryl, and substituted or unsubstituted heteroaryl.

$R^1$ may be selected from substituted or unsubstituted ($C_1$-$C_{10}$) alkyl, substituted or unsubstituted 2-10 membered heteroalkyl, substituted or unsubstituted ($C_3$-$C_7$) cycloalkyl, substituted or unsubstituted 3-7 membered heterocycloalkyl, substituted or unsubstituted aryl, and substituted or unsubstituted heteroaryl. In some embodiments, $R^1$ is a substituted or unsubstituted ($C_6$-$C_{10}$) alkyl.

In some embodiments, $R^1$ has the formula:

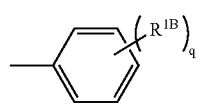

(III)

In Formula (III), q is an integer selected from 1 to 5. In some embodiments, q is an integer selected from 1 to 3. The integer q may also be 1.

The symbol $R^{1B}$ in Formula (III) may be selected from hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $-NR^{1B1}R^{1B2}$, $-OR^{1B3}$, $-C(O)NR^{1B4}R^{1B5}$, and $-S(O_2)R^{1B6}$. In another embodiment, $R^{1B}$ is selected from hydrogen, substituted alkyl, substituted or unsubstituted heteroalkyl, substituted cycloalkyl, substituted or unsubstituted heterocycloalkyl, substituted aryl, and substituted or unsubstituted heteroaryl. In some embodiments, $R^{1B}$ is selected from substituted or unsubstituted $(C_1-C_{10})$ alkyl, substituted or unsubstituted 2-10 membered heteroalkyl, substituted or unsubstituted $(C_3-C_7)$ cycloalkyl, substituted or unsubstituted 3-7 membered heterocycloalkyl, substituted or unsubstituted aryl, and substituted or unsubstituted heteroaryl.

$R^{1B1}$ and $R^{1B2}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $-COR^{1B10}$, and $-S(O_2)R^{1B9}$. $R^{1B9}$ and $R^{1B10}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{1B1}$ and $R^{1B2}$ are optionally joined to form a substituted or unsubstituted ring with the nitrogen to which they are attached. The ring formed by $R^{1B1}$ and $R^{1B2}$ optionally includes an additional ring heteroatom. $R^{1B1}$ and $R^{1B2}$ may also be independently selected from substituted alkyl, substituted or unsubstituted heteroalkyl, substituted or unsubstituted heterocycloalkyl, and substituted or unsubstituted heteroaryl.

$R^{1B3}$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $R^{1B3}$ is selected from hydrogen, substituted or unsubstituted heteroalkyl having a nitrogen; substituted or unsubstituted heterocycloalkyl having a ring nitrogen; substituted or unsubstituted heteroaryl having a ring nitrogen; and alkyl substituted with a substituted or unsubstituted heteroalkyl having a nitrogen, substituted or unsubstituted heterocycloalkyl having a ring nitrogen, and substituted or unsubstituted heteroaryl having a ring nitrogen.

$R^{1B6}$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and $-NR^{1B7}R^{1B8}$. $R^{1B7}$ and $R^{1B8}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{1B7}$ and $R^{1B8}$ are optionally joined with the nitrogen to which they are attached to form a substituted or unsubstituted ring.

In a related embodiment, $R^{1B}$ is selected from $-C(O)NR^{1B4}R^{1B5}$ and substituted or unsubstituted heteroaryl having a ring nitrogen. $R^{1B4}$ and $R^{1B5}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $R^{1B4}$ and $R^{1B5}$ are independently selected from hydrogen; substituted or unsubstituted heteroalkyl having a nitrogen; substituted or unsubstituted heterocycloalkyl having a ring nitrogen; substituted or unsubstituted heteroaryl having a ring nitrogen; and alkyl substituted with a substituted or unsubstituted heteroalkyl having a nitrogen, substituted or unsubstituted heterocycloalkyl having a ring nitrogen, and substituted or unsubstituted heteroaryl having a ring nitrogen. $R^{1B4}$ and $R^{1B5}$ are optionally joined to form a substituted or unsubstituted ring with the nitrogen to which they are attached. The ring formed by $R^{1B4}$ and $R^{1B5}$ optionally contains an additional heteroatom.

In another embodiment, $R^{1B1}$, $R^{1B2}$, $R^{1B3}$, $R^{1B4}$, $R^{1B5}$, $R^{1B6}$, $R^{1B7}$, $R^{1B8}$, $R^{1B9}$ and $R^{1B10}$ are independently selected from $R^{1B}$ is selected from substituted or unsubstituted $(C_1-C_{10})$ alkyl, substituted or unsubstituted 2-10 membered heteroalkyl, substituted or unsubstituted $(C_3-C_7)$ cycloalkyl, substituted or unsubstituted 3-7 membered heterocycloalkyl, substituted or unsubstituted aryl, and substituted or unsubstituted heteroaryl. In some embodiments, the rings formed by $R^{1B4}$ and $R^{1B5}$, $R^{1B7}$ and $R^{1B8}$, and $R^{1B1}$ and $R^{1B}$ are independently selected from, substituted or unsubstituted 3-7 membered heterocycloalkyl and substituted or unsubstituted heteroaryl.

$R^{1B1}$, $R^{1B2}$, $R^{1B3}$, $R^{1B4}$ and $R^{1B5}$ may also be independently selected from hydrogen and a substituted or unsubstituted ring, wherein the ring optionally contains a nitrogen atom and at least one additional ring heteroatom.

$R^1$ may also have the formula:

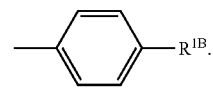

(IV)

In Formula (IV), $R^{1B}$ is selected from hydrogen, $-NR^{1B1}R^{1B2}$, $-OR^{1B3}$, substituted or unsubstituted $(C_1-C_{10})$ alkyl, substituted or unsubstituted 2-10 membered heteroalkyl, substituted or unsubstituted $(C_3-C_7)$cycloalkyl, substituted or unsubstituted 3-7 membered heterocycloalkyl, substituted or unsubstituted aryl, and substituted or unsubstituted heteroaryl.

In an exemplary embodiment, $R^{1A}$ is selected from hydrogen, substituted or unsubstituted $C_1-C_{10}$ alkyl, substituted or unsubstituted 2 to 10 membered heteroalkyl, substituted or unsubstituted $C_3-C_7$ membered cycloalkyl, substituted or unsubstituted 3-7 membered heterocycloalkyl, substituted or unsubstituted aryl, and substituted or unsubstituted heteroaryl. $R^{1C}$ and $R^{1D}$ are independently selected from hydrogen, substituted or unsubstituted $C_1-C_{10}$ alkyl, substituted or unsubstituted 2 to 10 membered heteroalkyl, substituted or unsubstituted $C_3-C_7$ membered cycloalkyl, substituted or unsubstituted 3-7 membered heterocycloalkyl, substituted or unsubstituted aryl, and substituted or unsubstituted heteroaryl. $R^{1C}$ and $R^{1D}$ may be joined together with the nitrogen atom to which they are attached to form a substituted or unsubstituted heteroaryl of 4 to 8 membered heterocycloalkyl. In some embodiments, $R^{1A}$ is hydrogen.

In some embodiments, $R^1$ is selected from $OR^{1A}$, $-NR^{1C}R^{1D}$, $-C(O)OR^{1A}$, and $-C(O)NR^{1C}R^{1D}$. In a related embodiment, $L^1$ is a substituted or unsubstituted ($C_1$-$C_6$)alkylene. In a further related embodiment, $L^1$ is an unsubstituted ($C_1$-$C_6$)alkylene.

In other embodiments, $R^1$ is selected from $-C(O)OR^{1A}$, $-C(O)NR^{1B}R^{1C}$, and $L^1$ is selected from a bond or substituted or unsubstituted ($C_1$-$C_6$)alkylene. In a related embodiment, $L^1$ is selected from a bond or unsubstituted ($C_1$-$C_6$) alkylene In still other embodiments, $R^1$ has the formula of formula (III) above, and $L^1$ is $-C(O)-$.

In an exemplary embodiment, $R^2$ is selected from substituted or unsubstituted ($C_1$-$C_{10}$) alkyl, substituted or unsubstituted 2-10 membered heteroalkyl, substituted or unsubstituted ($C_3$-$C_7$) cycloalkyl, substituted or unsubstituted 3-7 membered heterocycloalkyl, substituted or unsubstituted aryl, and substituted or unsubstituted heteroaryl.

In another exemplary embodiment, $R^{2A}$, $R^{2B}$, $R^{2C}$, and $R^{2D}$ are independently selected from substituted or unsubstituted ($C_1$-$C_{10}$) alkyl, substituted or unsubstituted 2-10 membered heteroalkyl, substituted or unsubstituted ($C_3$-$C_7$) cycloalkyl, substituted or unsubstituted 3-7 membered heterocycloalkyl, substituted or unsubstituted aryl, and substituted or unsubstituted heteroaryl.

$R^2$ may also have the formula:

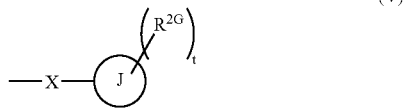

(V)

In Formula (V), $R^{2G}$ is selected from halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In a related embodiment, $R^{2G}$ is selected from hydrogen, substituted or unsubstituted ($C_1$-$C_{10}$) alkyl, substituted or unsubstituted 2-10 membered heteroalkyl, substituted or unsubstituted ($C_3$-$C_7$) cycloalkyl, substituted or unsubstituted 3-7 membered heterocycloalkyl, substituted or unsubstituted aryl, and substituted or unsubstituted heteroaryl. In another related embodiment, $R^{2G}$ is a branched or unbranched ($C_1$-$C_{10}$) alkyl. The symbol t is an integer selected from 0 to 5.

One of skill in the art will immediately recognize that the value for t is limited by the number of ring members in ring J. For example, the symbol t is an integer from 0 to 5 where J is a 6 or 7 membered substituted or unsubstituted ring. The symbol t is an integer from 0 to 4 where J is a 5 membered substituted or unsubstituted ring. The symbol t is an integer from 0 to 3 where J is a 4 membered substituted or unsubstituted ring. The symbol t is an integer from 0 to 2 where J is a 3 membered substituted or unsubstituted ring.

In some embodiments, the symbol t is 1.

J is selected from substituted or unsubstituted ring selected from substituted or unsubstituted ($C_3$-$C_7$) cycloalkyl, substituted or unsubstituted 3-7 membered heterocycloalkyl, substituted or unsubstituted aryl, and substituted or unsubstituted heteroaryl. In some embodiments, J is a substituted or unsubstituted ring selected from substituted or unsubstituted 3-7 membered heterocycloalkyl, substituted or unsubstituted aryl, and substituted or unsubstituted heteroaryl.

X is selected from a bond, $-S(O_2)-$, and $-S(O_2)NR^{2I}-$. $R^{2I}$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, $R^{2I}$ is selected from substituted or unsubstituted ($C_1$-$C_{10}$) alkyl, substituted or unsubstituted 2-10 membered heteroalkyl, substituted or unsubstituted ($C_3$-$C_7$) cycloalkyl, substituted or unsubstituted 3-7 membered heterocycloalkyl, substituted or unsubstituted aryl, and substituted or unsubstituted heteroaryl. In another embodiment, $R^{2I}$ is selected from hydrogen, substituted or unsubstituted alkyl, and substituted or unsubstituted heteroalkyl.

In another exemplary embodiment, the compound of the present invention has the formula

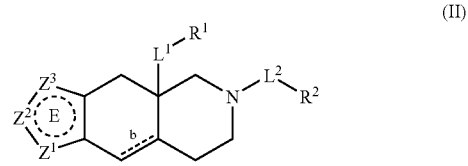

(II)

In Formula (II), the dashed ring represents unsaturated, partially saturated, or fully saturated bonds within ring E. Thus, a double bond is optionally present at any of the bonds within ring E. The dashed line b is optionally a bond.

$Z^1$ is selected from $-NR^5-$, $=N-$, $-O-$, and $-S-$. $R^5$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted heteroaryl, and substituted or unsubstituted aryl. $R^5$ may also be selected from hydrogen, substituted or unsubstituted alkyl, substituted or unsubstituted heteroalkyl, and substituted or unsubstituted aryl. Alternatively, $R^5$ may be selected from hydrogen and substituted or unsubstituted aryl. In another embodiment, $R^5$ is an substituted or unsubstituted $C_1$-$C_{10}$ alkyl, or substituted or unsubstituted aryl. In some embodiments, $R^5$ is an unsubstituted $C_1$-$C_{10}$ alkyl, unsubstituted aryl, or fluoro-substituted aryl.

$Z^2$ is selected from $-CR^{6A}R^{6B}-$, $=CR^{6A}-$, $-C(O)-$, $-NR^{6C}-$, $=N-$, $-O-$, $-S-$, $-CR^{6A}R^{6B}-NR^{6C}-$, $=CR^{6A}-NR^{6C}-$, $-CR^{6A}=N-$, $-CR^{6A}R^{6B}-N=$, and $=CR^{6A}-N=$. $R^{6C}$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted heteroaryl, and substituted or unsubstituted aryl. $R^{6C}$ may also be selected from hydrogen, substituted or unsubstituted alkyl, substituted or unsubstituted heteroaryl, substituted or unsubstituted aryl.

$R^{6A}$ and $R^{6B}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted heteroaryl, substituted or unsubstituted aryl, $-NR^{6A1}R^{6A2}$, and $-OR^{6A3}$. $R^{6A}$ and $R^{6C}$ are optionally joined together to form a substituted or unsubstituted ring, wherein the ring optionally comprises an additional ring heteroatom. $R^{6A}$ and $R^{6B}$ may also be independently selected from hydrogen, substituted or unsubstituted alkyl, substituted or unsubstituted heteroaryl, substituted or unsubstituted aryl, —$NR^{6A1}R^{6A2}$, and —$OR^{6A3}$.

$R^{6A1}$ and $R^{6A2}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{6A1}$ and $R^{6A2}$ are optionally joined to form a substituted or unsubstituted ring with the nitrogen to which they are attached. The ring formed by $R^{6A1}$ and $R^{6A2}$ optionally contains an additional ring heteroatom.

$R^{6A3}$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

$Z^3$ is selected from —$CR^{7A}R^{7B}$—, =$CR^{7A}$—, —C(O)—, —$NR^{7C}$—, =N—, —O—, and —S—. $R^{7C}$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted heteroaryl, and substituted or unsubstituted aryl. $R^{7C}$ may also be selected from hydrogen, substituted or unsubstituted alkyl, substituted or unsubstituted heteroaryl, and substituted or unsubstituted aryl.

$R^{7A}$ and $R^{7B}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted heteroaryl, substituted or unsubstituted aryl, —$NR^{7A1}R^{7A2}$, and —$OR^{7A3}$. $R^{7A}$ and $R^{7B}$ may also be independently selected from hydrogen, substituted or unsubstituted alkyl, substituted or unsubstituted heteroaryl, substituted or unsubstituted aryl, —$NR^{7A1}R^{7A2}$, and —$OR^{7A3}$.

$R^{7A1}$ and $R^{7A2}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{7A1}$ and $R^{7A2}$ are optionally joined to form a substituted or unsubstituted ring with the nitrogen to which they are attached. The ring formed by $R^{7A1}$ and $R^{7A2}$ optionally contains an additional ring heteroatom.

$R^{7A3}$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In some embodiments, $R^5$, $R^{6A}$, $R^{6B}$, $R^{6C}$, $R^{6A1}$, $R^{6A2}$, $R^{6A3}$, $R^{7A}$, $R^{7B}$, $R^{7C}$, $R^{7A1}$, $R^{7A2}$, $R^{7A3}$ are independently selected from substituted or unsubstituted ($C_1$-$C_{10}$) alkyl, substituted or unsubstituted 2-10 membered heteroalkyl, substituted or unsubstituted ($C_3$-$C_7$) cycloalkyl, substituted or unsubstituted 3-7 membered heterocycloalkyl, substituted or unsubstituted aryl, and substituted or unsubstituted heteroaryl.

A variety of substituted or unsubstituted rings may be formed by connecting some of the substituents described above. For example, $R^5$ is optionally joined with $R^{6A}$ or $R^{6C}$ to form a substituted or unsubstituted ring optionally including an additional ring heteroatom. In addition, $R^{7A}$ is optionally joined with $R^{6A}$ or $R^{6C}$ to form a substituted or unsubstituted ring optionally including an additional ring heteroatom. Still further, $R^{7C}$ is optionally joined with $R^{6A}$ or $R^{6C}$ to form a substituted or unsubstituted ring optionally including an additional ring heteroatom. In some related embodiments, where a ring is formed by $R^5$ or $R^{7A}$ as described above, the ring is selected from substituted or unsubstituted ($C_3$-$C_7$) cycloalkyl, substituted or unsubstituted 3-7 membered heterocycloalkyl, substituted or unsubstituted aryl, and substituted or unsubstituted heteroaryl.

In some embodiments of the Formula (II) compound, $Z^1$ is —$NR^5$—, $Z^2$ is =N—, and $Z^3$ is =$CR^{7A}$—. In a related embodiment, $R^{7A}$ is hydrogen and $R^5$ is a member selected from hydrogen, substituted or unsubstituted aryl, substituted or unsubstituted heteroaryl, substituted or unsubstituted arylalkyl and substituted or unsubstituted heteroarylalkyl. In a further related embodiment, $R^{7A}$ is hydrogen and $R^5$ is a member selected from substituted or unsubstituted alkyl and substituted or unsubstituted cycloalkyl.

$R^5$ may also have the formula:

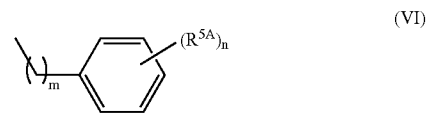

(VI)

In Formula (VI), $R^{5A}$ is a member selected from hydrogen, halogen, —$OR^{5A1}$, —$NR^{5A2}R^{5A3}$, —$S(O_2)NR^{5A2}R^{5A3}$, CN, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. The symbol m is an integer independently selected from 0 to 10. The symbol n is an integer independently selected from 1 to 5.

$R^{5A1}$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{5A2}$ and $R^{5A3}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $R^{5A2}$ and $R^{5A3}$ are optionally joined to form a substituted or unsubstituted ring with the nitrogen to which they are joined. The ring formed by $R^{5A2}$ and $R^{5A3}$ may be a substituted or unsubstituted ($C_3$-$C_7$) cycloalkyl, substituted or unsubstituted 3-7 membered heterocycloalkyl, substituted or unsubstituted aryl, or substituted or unsubstituted heteroaryl.

In some embodiments, $R^{5A}$, $R^{5A1}$, $R^{5A2}$, $R^{5A3}$ are independently selected from substituted or unsubstituted ($C_1$-$C_{10}$) alkyl, substituted or unsubstituted 2-10 membered heteroalkyl, substituted or unsubstituted ($C_3$-$C_7$) cycloalkyl, substituted or unsubstituted 3-7 membered heterocycloalkyl, substituted or unsubstituted aryl, and substituted or unsubstituted heteroaryl.

In some embodiments of Formula (VI), n is 1 and m is selected from 0 and 1. In a related embodiment, n is 1 and m is 1. In another related embodiment, $R^{5A1}$, $R^{5A2}$ and $R^{5A3}$ are hydrogen.

In another related embodiment, $R^5$ and $R^{7A}$ are hydrogen.

In yet another related embodiment, b is a bond.

In some embodiments of the Formula (II) compound, $Z^1$ is —$NR^5$—, $Z^2$ is =$CR^{6A}$—, and $Z^3$ is =N—. In a related embodiment, $R^5$ is a member selected from hydrogen and substituted or unsubstituted aryl.

In an exemplary embodiment of the compound of Formula (I), the dashed line b is a bond; $R^1$ is substituted or unsubstituted benzyl; $L^1$ is a bond; $L^2$ is a bond; and $R^2$ has the formula:

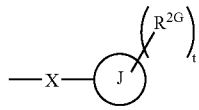

(V)

In this exemplary embodiment, $R^{2G}$ is selected from hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. J is a substituted or unsubstituted ring selected from substituted or unsubstituted $(C_3$-$C_7)$ cycloalkyl, substituted or unsubstituted 3-7 membered heterocycloalkyl, substituted or unsubstituted aryl, and substituted or unsubstituted heteroaryl. X is $—S(O_2)—$. The symbol t is an integer selected from 0 to 5.

In another embodiment, the compound of Formula (I) has the formula

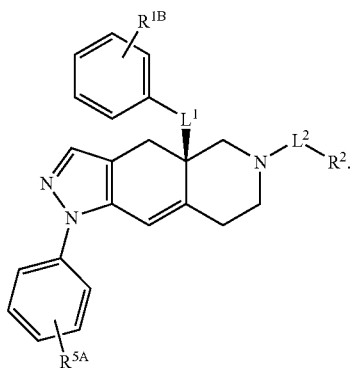

(VII)

In Formula (VII), $L^2$ and $R^2$ are as defined above in the discussion of Formula (I). $R^{1B}$ is as defined above in the discussion of Formula (III). $R^{5A}$ is as defined above in the discussion of Formula (VI). $L^1$ is selected from $—CH_2—$ and $—C(O)—$.

In another exemplary embodiment, the compound of Formula (I) has the formula

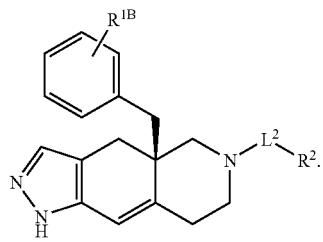

(VIII)

In Formula (VIII), $L^2$ and $R^2$ are as defined above in the discussion of Formula (I). $R^{1B}$ is as defined above in the discussion of Formula (III).

In another exemplary embodiment, the compound of Formula (I) has the formula

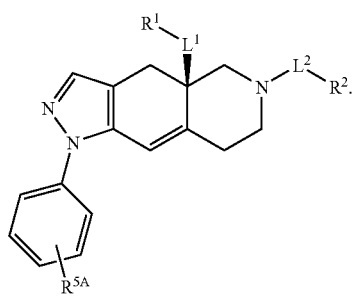

(IX)

In Formula (X), $L^2$ and $R^2$ are as defined above in the discussion of Formula (I). $R^{5A}$ is as defined above in the discussion of Formula (VI). -$L^1$-$R^1$ is selected from methyl (i.e. $L^1$ is a bond and $R^1$ is methyl), $—OR^{1A}$, $—C(O)OR^{1A}$ (i.e. $L^1$ is a $—C(O)—$ and $R^1$ is $—OR^{1A}$), $—CH_2—OR^{1A}$, $—(CH_2)_2—OR^{1A}$, $—NR^{1C}R^{1D}$, $—C(O)NR^{1C}R^{1D}$, $—CH_2—NR^{1C}R^{1D}$, and $—(CH_2)_2—NR^{1C}R^{1D}$.

In another exemplary embodiment, the compound of Formula (I) has the formula

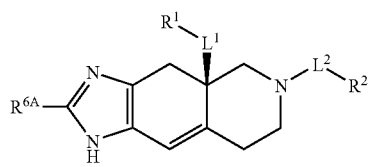

(X)

In Formula (X), $L^1$, $R^1$, $L^2$ and $R^2$ are as defined above in the discussion of Formula (I). $R^{6A}$ is as defined above in the discussion of Formula (II).

In another exemplary embodiment, the compound of Formula (I) has the formula

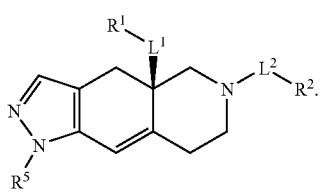

(XI)

In Formula (XI), $R^{1A}$, $L^2$ and $R^2$ are as defined above in the discussion of Formula (I). $R^5$ is as defined above in the discussion of Formula (II). -$L^1$-$R^1$ is selected from methyl (i.e. $L^1$ is a bond and $R^1$ is methyl), $—OR^{1A}$, $—C(O)OR^{1A}$ (i.e. $L^1$ is a $—C(O)—$ and $R^1$ is $—OR^{1A}$), $—CH_2—OR^{1A}$, $—(CH_2)_2—OR^{1A}$, $—NR^{1C}R^{1D}$, $—C(O)NR^{1C}R^{1D}$, $—CH_2—NR^{1C}R^{1D}$, and $—(CH_2)_2—NR^{1C}R^{1D}$. In a related embodiment, -$L^1$-$R^1$ is selected from $—CH_2—OR^{1A}$, and $—CH_2—NR^{1C}R^{1D}$.

In an exemplary embodiment of the compound of Formula (II), the dashed line b is a bond; $R^1$ is substituted or unsubstituted benzyl; $L^1$ is a bond; $L^2$ is a bond; $Z^1$ is —NR$^5$—; $Z^2$ is =CR$^{6A}$—, $Z^3$ is =N—; and R$^2$ has the formula:

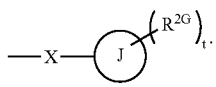

(V)

In this exemplary embodiment, R$^{2G}$ is selected from hydrogen, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. J is a substituted or unsubstituted ring selected from substituted or unsubstituted ($C_3$-$C_7$) cycloalkyl, substituted or unsubstituted 3-7 membered heterocycloalkyl, substituted or unsubstituted aryl, and substituted or unsubstituted heteroaryl. The symbol t is 1. X is —S(O$_2$)—. R$^5$ is hydrogen, alkyl, cycloalkyl, aryl or heteroaryl. R$^{6A}$ is as defined in the description of Formula (II).

In another exemplary embodiment, the compound of Formula (I) is selected from one of the compounds set forth in Examples 15-23, 25, 28-29, or 33-62.

In some embodiments of the compounds of Formulae (I)-(XI), each substituted alkylene, substituted heteroalkylene, substituted alkyl, substituted heteroalkyl, substituted cycloalkyl, substituted heterocycloalkyl, substituted aryl, substituted heteroaryl, substituted arylalkyl, substituted heteroarylalkyl, and substituted ring structures are substituted with a substituent group. In other embodiments of the compounds of Formulae (I)-(XI), each substituted alkylene, substituted heteroalkylene, substituted alkyl, substituted heteroalkyl, substituted cycloalkyl, substituted heterocycloalkyl, substituted, substituted heteroaryl, substituted alkylene, substituted heteroalkylene, substituted arylalkyl, and substituted heteroarylalkyl is substituted with a size-limited substituent group. In another embodiments of the compounds of Formulae (I)-(XI), each substituted alkylene, substituted heteroalkylene, substituted alkyl, substituted heteroalkyl, substituted cycloalkyl, substituted heterocycloalkyl, substituted, substituted heteroaryl, substituted alkylene, substituted heteroalkylene, substituted arylalkyl, and substituted heteroarylalkyl is substituted with a lower substituent group.

For example, where R$^1$, R$^{1A}$, R$^{1B}$, R$^{1B1}$, R$^{1B2}$, R$^{1B3}$, R$^{1B4}$, R$^{1B5}$, R$^{1B6}$, R$^{1B7}$, R$^{1B8}$, R$^{1B9}$, R$^{1B10}$, R$^{1C}$, R$^{1D}$, R$^{2A}$, R$^{2B}$, R$^{2C}$, R$^{2D}$, R$^{2G}$, R$^{2I}$, R$^{3A}$, R$^{3B}$, R$^{3C}$, R$^5$, R$^{5A}$, R$^{5A1}$, R$^{5A2}$, R$^{5A3}$, R$^{6A}$, R$^{6B}$, R$^{6C}$, R$^{6A1}$, R$^{6A2}$, R$^{6A3}$, R$^{7A}$, R$^{7B}$, R$^{7C}$, R$^{7A1}$, R$^{7A2}$, R$^{7A3}$, R$^{2A}$ are independently selected from a substituted alkylene, substituted heteroalkylene, substituted alkyl, substituted heteroalkyl, substituted cycloalkyl, substituted heterocycloalkyl, substituted aryl, substituted heteroaryl, substituted arylalkyl, substituted heteroarylalkyl, or form substituted ring structures, the designated R group may be substituted with a substituent group. Alternatively, the designated R group may be substituted with a size-limited substituent group. In some embodiments, the designated R group is substituted with a lower substituent group.

Likewise, where L$^1$ and L$^2$ are independently selected from a substituted alkylene or substituted heteroalkylene, L$^1$ and/or L$^2$ may substituted with a substituent group, size-limited substituent group, or lower substituent group. Where A is selected from substituted cycloalkyl, substituted heterocycloalkyl, substituted aryl, and substituted heteroaryl, A may substituted with a substituent group, size-limited substituent group, or lower substituent group.

II. Exemplary Syntheses

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. Although some compounds in Schemes I-XVI may indicate relative stereochemistry, the compounds may exist as a racemic mixture or as either enantiomer. Compounds containing the double bond in the azadecalin core are designated Series A. Ring-saturated compounds are designated Series B.

Scheme I

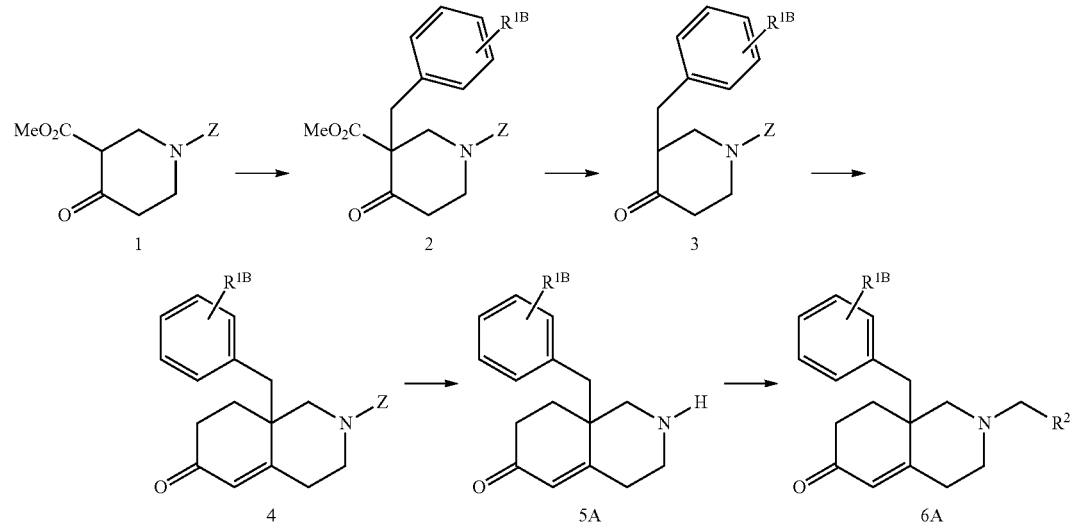

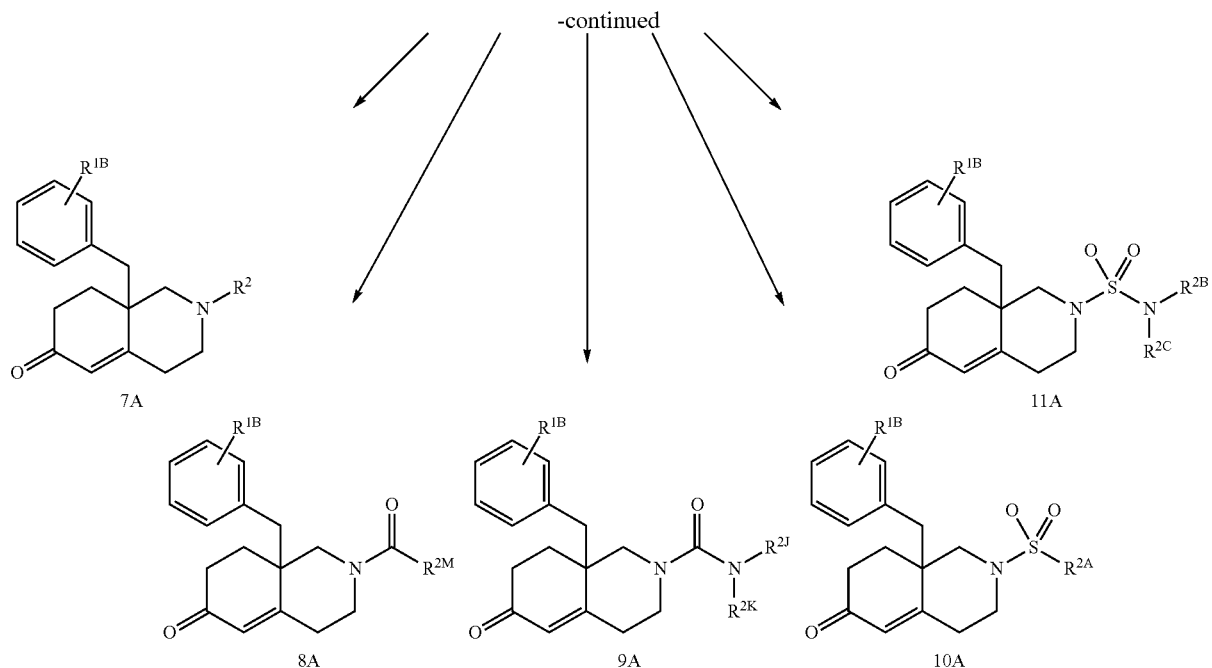

In Scheme I, $R^{1B}$, $R^2$, $R^{2A}$, $R^{2B}$, and $R^{2C}$ are as defined above in the discussion of the compounds of the present invention. $R^{2M}$, $R^{2J}$, and $R^{2K}$ are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

Compounds 6A-11A are prepared as illustrated in Scheme I. A suitably N-protected piperidone-2-carboxylic acid ester 1 is treated with a base such as sodium hydride, sodium ethoxide or potassium tert-butoxide in a polar solvent (e.g. N,N-dimethylformamide, ethanol, tert-butanol, dimethylsulfoxide, N-methyl-2-pyrrolidone and the like) followed by an alkylating agent to afford the alkylated keto ester 2. Suitable N-protecting groups (Z) include benzyl and carbamate groups such as tert-butoxycarbonyl (Boc) and the like. Typical alkylating agents are primary, secondary or arylalkyl halides and are preferably benzyl halides in which the aromatic ring can be substituted with a $R^{1B}$ group.

Keto ester 2 is hydrolyzed and decarboxylated by heating in a suitable solvent such as aqueous methanol or ethanol in the presence of a strong acid (e.g. hydrochloric acid or sulfuric acid) to afford ketone 3. The reaction is typically carried out at the reflux temperature of the solvent mixture.

Ketone 3 is converted to enone 4 by a Robinson annelation reaction involving treatment of 3 with a base (e.g. potassium or sodium alkoxides) in an alcohol solvent (e.g. methanol, ethanol, or tert-butanol) followed by addition of methylvinyl ketone (MVK). The reaction is typically carried out at 0-25° C. This reaction can also be carried out with a nitrogen-containing base such as pyrrolidine, piperidine or morpholine in an aprotic solvent (e.g. benzene, toluene or dioxane) at reflux temperature followed by cooling and addition of MVK.

Enone 4 is prepared in optically active form when the nitrogen-containing base is an optical isomer of α-methyl-benzylamine as described in *J. Med. Chem.* 39: 2302 (1996). Alternatively, the Robinson annelation can be carried out in an asymmetric manner with catalysis by an amino acid such as l-proline.

Removal of the N-protecting group Z from compound 4 is accomplished under standard conditions, such as treatment with a chloroformate and subsequent hydrolysis when Z is benzyl, to afford amine 5A. Suitable chloroformates include methyl chloroformate, ethyl chloroformate and α-chloroethyl chloroformate. When Z is a group such as Boc, deprotection is accomplished by treatment with a strong acid such as HCl in a protic solvent (e.g., ethanol) or with trifluoroacetic acid.

Compound 6A may be prepared by alkylation of 5A with a primary or secondary alkyl, cycloalkyl, heterocycloalkyl, arylalkyl, or heteroarylalkyl halide. Alternatively, 6A may be prepared by reductive alkylation of 5A with the requisite aldehyde in the presence of a reducing agent such as sodium borohydride or sodium cyanoborohydride in an inert solvent (e.g. 1,2-dichloroethane).

Compound 7A where $R^2$ is aryl or heteroaryl may be prepared by treatment of 5A with an aryl, heteroaryl halide, or boronic acid in the presence of a copper or palladium catalyst (e.g., copper (II) acetate, palladium (II) chloride) and a base such as triethylamine.

Compound 8A may be prepared by acylation of 5A with a primary, secondary or tertiary alkyl, cycloalkyl, heterocycloalkyl, arylalkyl, or heteroarylalkyl carbonyl halide in a suitable protic or aprotic solvent in the presence of a base such as sodium hydroxide, triethylamine and the like. Alternatively, 8A may be prepared by coupling of amine 5A with the requisite carboxylic acid in the presence of a suitable coupling agent such as N,N-dicyclohexylcarbodiimide.

Compound 9A where $R^{2K}$ is hydrogen may be prepared by treatment of 5A with a primary, secondary or tertiary alkyl, cycloalkyl, heterocycloalkyl, arylalkyl, or heteroarylalkyl isocyanate in an inert solvent (e.g. toluene, dichloromethane, 1,2-dichloroethane or dioxane). When $R^{2K}$ is a group other than hydrogen, compound 9A may be prepared by treatment of 5A with the carbamoyl halide $R^{2J}R^{2K}NC(O)X$ (where X is Cl, Br, F) in an inert solvent (e.g. toluene, dichloromethane, 1,2-dichloroethane or dioxane) in the presence of a base such as triethylamine.

Compound 10A is prepared by treatment of 5A with a primary, secondary or tertiary alkyl, cycloalkyl, heterocycloalkyl, arylalkyl, or heteroarylalkyl sulfonyl halide in an inert solvent (e.g. toluene, dichloromethane, 1,2-dichloroethane or dioxane) in the presence of a base such as triethylamine.

Compound 11A is prepared by treatment of 5A with the sulfamoyl halide $R^{2B}R^{2C}NSO_2X$ (where X is Cl, Br, or F) in an inert solvent (e.g. toluene, dichloromethane, 1,2-dichloroethane or dioxane) in the presence of a base such as triethylamine.

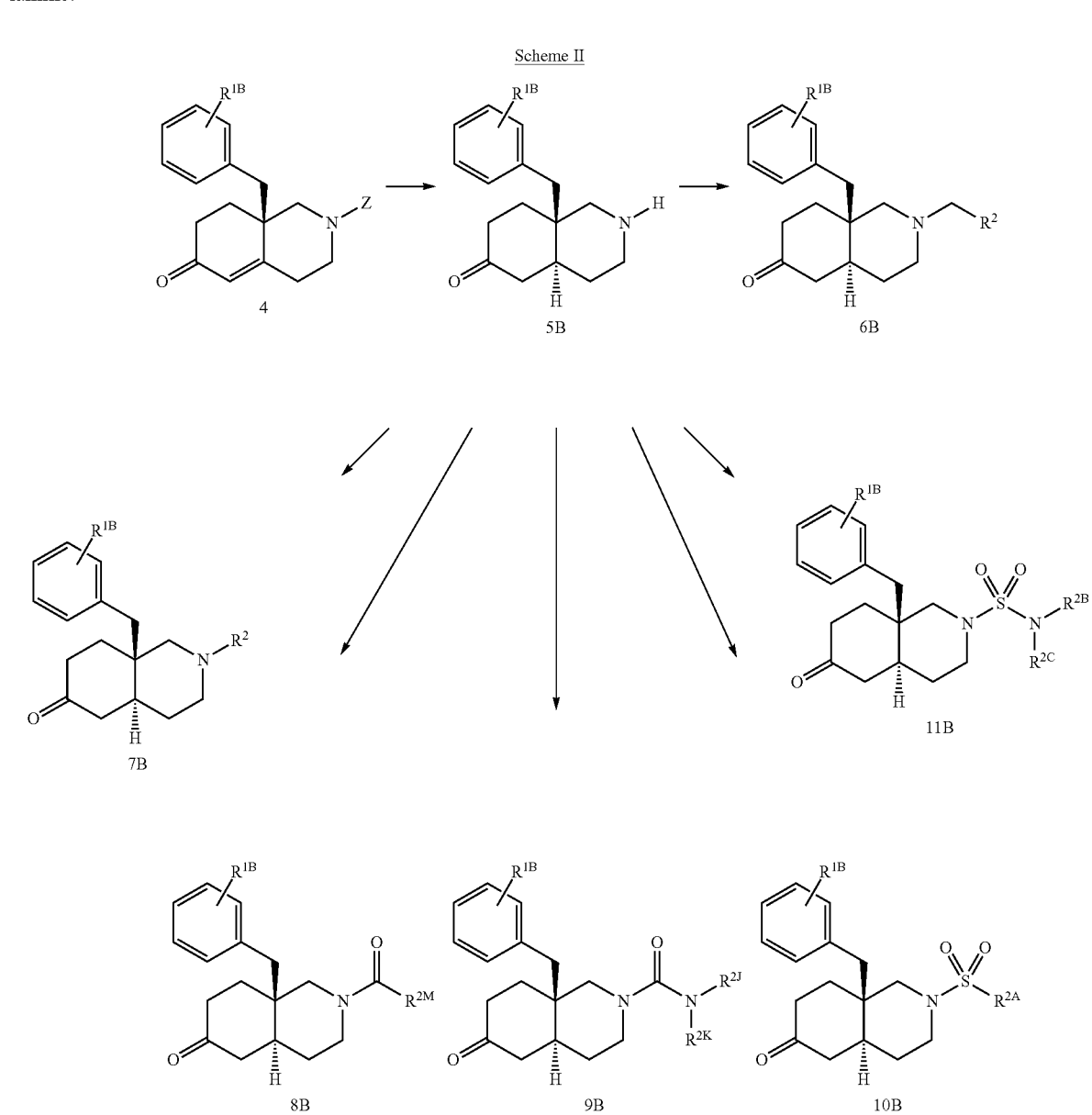

Scheme II

In Scheme II, $R^{1B}$, $R^2$, $R^{2A}$, $R^{2B}$, $R^{2C}$, $R^{2M}$, $R^{2J}$, and $R^{2K}$ are as defined above in Scheme I.

Compounds 6B-11B are similarly prepared from saturated ketone 5B (Scheme II) according to the reactions previously described in Scheme I. One skilled in the art will immediately recognize that compound 5B can also exist as the cis isomer. Scheme II exemplifies the preparation of the trans isomers of compounds 6B-11B. However, the reaction scheme is equally applicable to the preparation of the corresponding cis isomers.

Reduction of enone 4 to saturated ketone 5B is accomplished by catalytic hydrogenation using a catalyst such as palladium or platinum catalyst in an inert solvent, such as tetrahydrofuran or an alcohol such as ethanol. Alternatively, 5B can be prepared by treatment of 4 with a dissolving metal, such as lithium, in liquid ammonia.

Scheme III

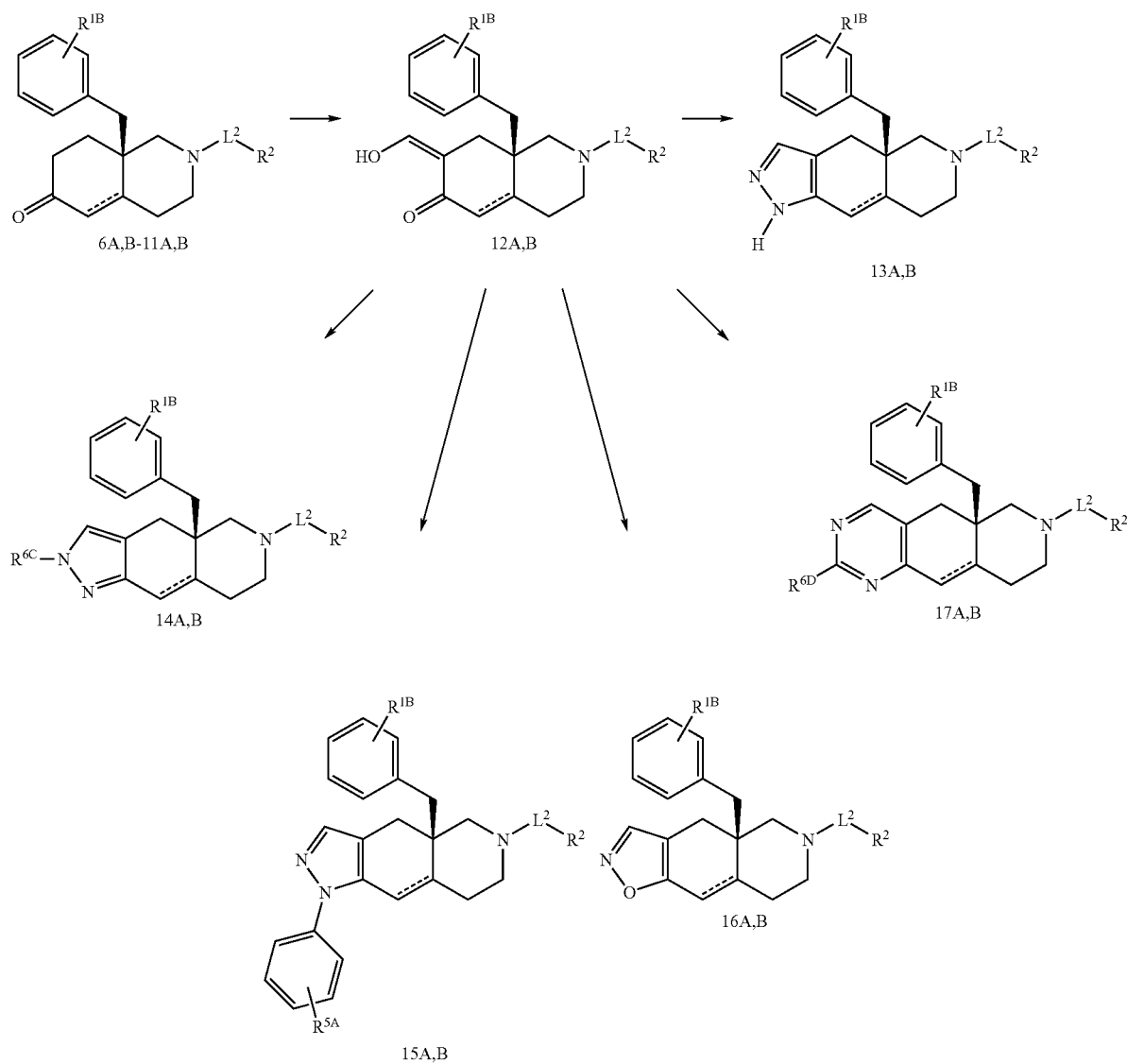

In Scheme III, $R^{1B}$, $R^2$, $R^{5A}$, $R^{6C}$, and $L^2$ are as defined above in the discussion of the compounds of the present invention. $R^{6D}$ is selected from hydrogen, halogen, —OH, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

Compounds 13A,B-17A,B are prepared as described in Scheme III. Treatment of ketones 6A,B-11A,B with a formylating agent such as ethyl formate in the presence of a base such as sodium methoxide or sodium hydride in an aprotic solvent such as toluene affords hydroxymethylene derivatives 12A,B. Treatment of 12A,B with hydrazine in an alcohol solvent with heating to the reflux temperature of the mixture yields pyrazoles 13A,B. Treatment of 12A,B with an alkyl hydrazine under similar conditions affords pyrazoles 14A,B. Treatment of 12A,B with an aryl hydrazine affords the regioisomeric pyrazoles 15A,B. Treatment of 12A,B with hydroxylamine in a solvent such as ethyl acetate in the presence of acetic acid affords isoxazoles 16A,B. Pyrimidines 17A,B are prepared by treatment of 12A,B with guanidine ($R^{6D}$=NH$_2$) or an amidine ($R^{6D}$=alkyl or aryl) in an alcohol solvent in the presence of a base such as sodium ethoxide.

Compounds 19A,B-21A,B are prepared as shown in Scheme IV. Bromination of ketones 6A,B-11A,B by conventional methods such as treatment with cuprous bromide or by treatment of 6A,B-11A,B with a strong base, such as lithium diisopropylamide, and a brominating agent such as N-bromosuccinimide in a solvent such as tetrahydrofuran, affords bromo derivatives 18A,B. Thiazoles 19A,B are prepared by treatment of 18A,B with thiourea ($R^{6A}$=NH$_2$) or a thioamide ($R^{6A}$=alkyl or aryl) in a solvent such as acetonitrile. Imidazoles 22A,B are prepared by treatment of 18A,B with guanidine ($R^{6A}$=NH$_2$) or an amidine ($R^{6A}$=alkyl or aryl) in an alcohol solvent in the presence of a base such as sodium ethoxide. Oxazoles 20A,B are prepared by heating 18A,B with a primary amide in an alcohol solvent such as ethanol. Imidazolones 21A,B are prepared by heating 18A,B with a N,N'-disubstituted urea in an alcohol solvent such as ethanol.

Scheme IV

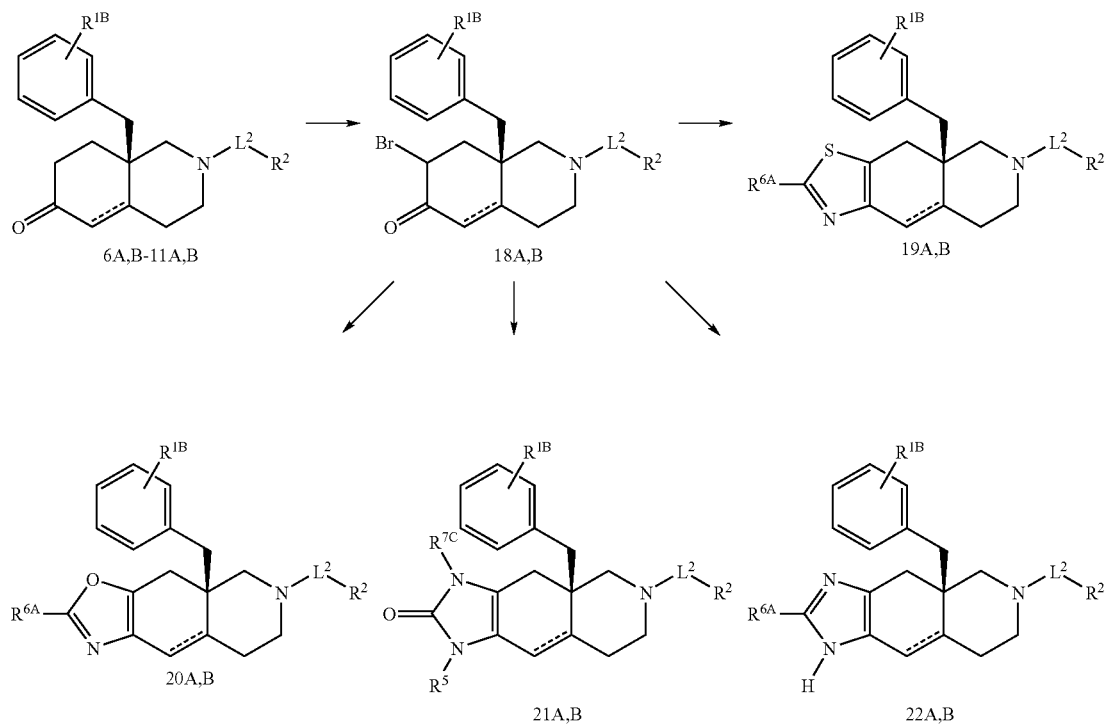

In Scheme IV, $R^{1B}$, $L^2$, $R^2$, $R^5$, $R^{6A}$, and $R^{7C}$ are as defined above in the discussion of the compounds of the present invention.

Scheme V

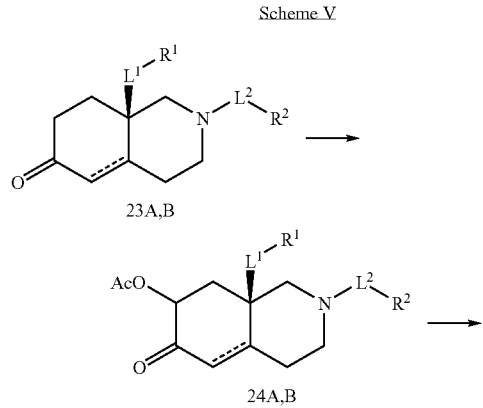

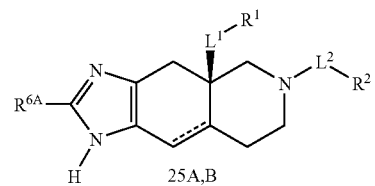

Substituted imidazoles 25A,B can also be prepared as shown in Scheme V. In Scheme V, $L^1$, $L^2$, $R^1$, $R^2$ and $R^{6A}$ are as defined above in the compounds of the present invention. Compounds 24A,B may be prepared from ketones 23A,B by treatment with manganese acetate in a suitable inert solvent such as toluene or THF. Conversion of compounds 24A,B to compounds 25A,B is accomplished by treatment with copper$^{II}$ acetate and ammonia and a suitable aldehyde (for example where $R^{6A}$ is methyl, the ketone is acetaldehyde) in a protic solvent such as methanol or ethanol.

Scheme VI

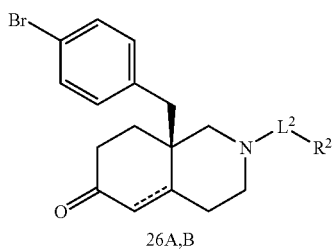

-continued

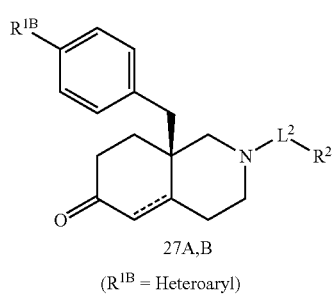

27A,B
(R[1B] = Heteroaryl)

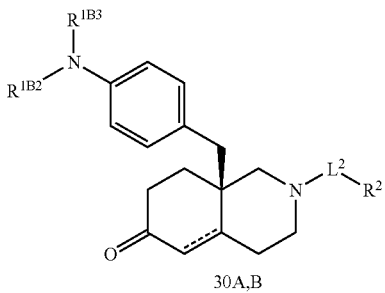

30A,B

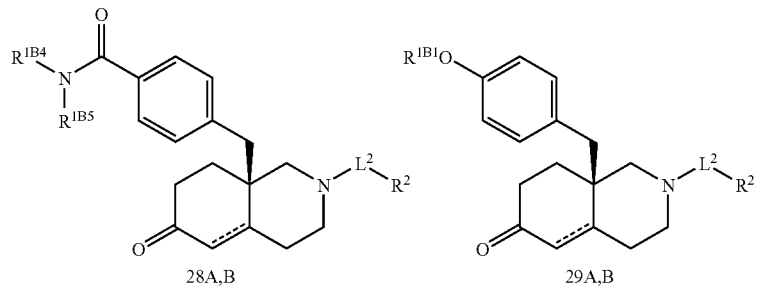

28A,B

29A,B

The group $R^{1B}$ in compounds 27A,B-30A,B can be modified prior to synthesis of the compounds according to Schemes III and IV, as exemplified in Scheme VI. Thus, brominated derivatives, such as 26A,B can be converted to amino derivatives 30A,B by conversion to the (bis-pinacolato)diboron derivative followed by copper-catalyzed amination. Similarly, the bromo derivative may be converted to aryl ethers 29A,B by metal-catalyzed ether formation or to amide derivatives 28A,B by palladium-catalyzed carbonylation/amidation procedures. Derivatives 27A,B in which $R^{1B}$ is heteroaryl can be prepared by treatment of 26A,B with a heteroarylboronic acid in the presence of a palladium catalyst.

In Scheme VI, $R^{1B}$ is heteroaryl and $R^{1B1}$, $R^{1B2}$, $R^{1B3}$, $R^{1B4}$, $R^{1B5}$, $L^2$, and $R^2$ are as defined above in the discussion of the compounds of the present invention.

Scheme VII

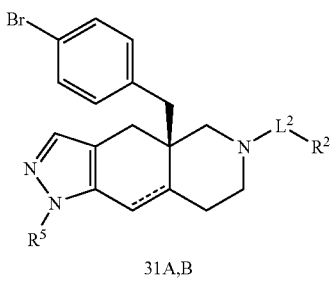

31A,B

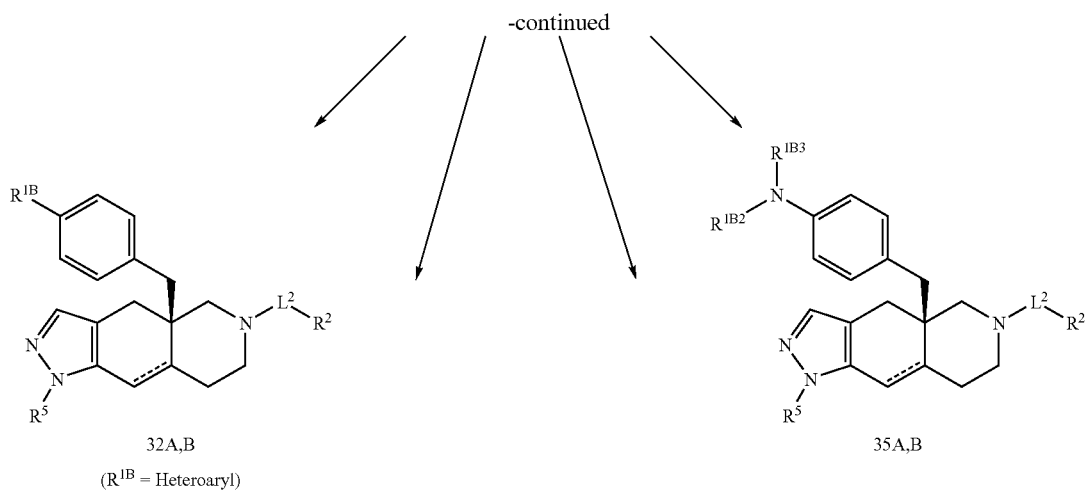

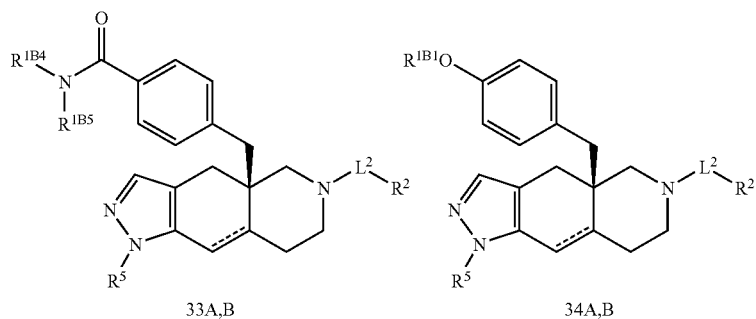

Alternatively, the group $R^{1B}$ in compounds 13A,B-17A,B and 19A,B-22A,B can be modified subsequent to synthesis of the compounds according to Schemes III and IV, as exemplified in Scheme VII for the synthesis of pyrazole derivatives 32A,B-35A,B. Thus, brominated derivatives, such as 31A,B can be converted to amino derivatives 35A,B by conversion to the (bis-pinacolato)diboron derivative followed by copper-catalyzed amination. Similarly, the bromo derivative may be converted to aryl ethers 34A,B by metal-catalyzed ether formation or to amide derivatives by palladium-catalyzed carbonylation/amidation procedures. Derivatives 32A,B in which $R^{1B}$ is heteroaryl can be prepared by treatment of 31A,B with a heteroarylboronic acid in the presence of a palladium catalyst.

In Scheme VII, $R^{1B}$ is heteroaryl and $R^{1B1}$, $R^{1B2}$, $R^{1B3}$, $R^{1B4}$, $R^{1B5}$, $L^2$, and $R^2$ are as defined above in the discussion of the compounds of the present invention.

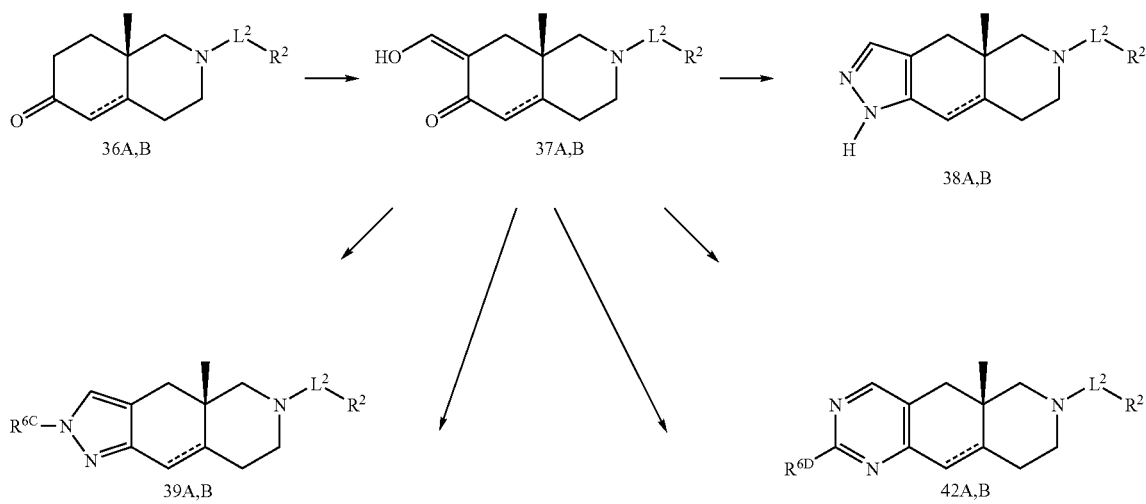

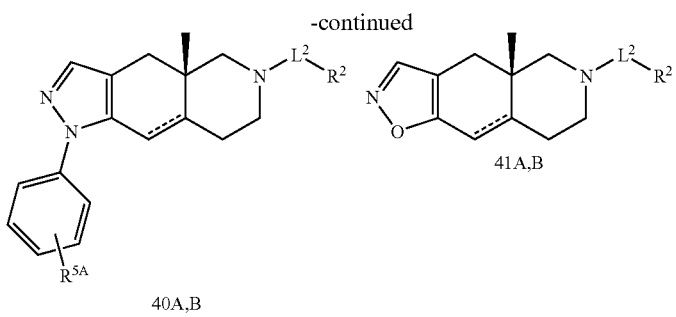

It will be appreciated by one skilled in the art that the routes illustrated in Schemes I-IV and VI, VII wherein $L^1$-$R^1$ represents a substituted benzyl group may also be applied to compounds in which $L^1$-$R^1$ represents an alkyl substituted lower alkyl group, for example a methyl group, as described in Scheme VIII. Either enantiomer of enone 36A, in which $L^2$-$R^2$ represents a benzyl group, can be prepared by Robinson annelation when the nitrogen-containing base is an optical isomer of α-methylbenzylamine as described in *J. Med. Chem.* 39: 2302 (1996). Compounds 38A,B-42A,B are prepared from 37A,B according to the procedures described for the preparation of the compounds in Scheme III.

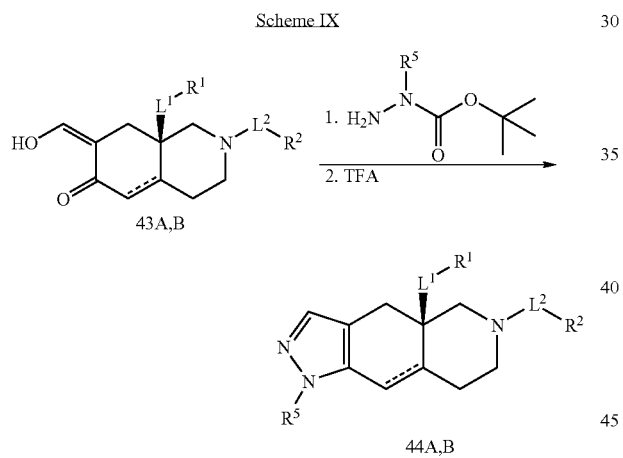

Pyrazoles 44A,B, in which $R^5$ is alkyl, substituted alkyl, cycloalkyl or substituted cycloalkyl can be prepared by an alternative procedure as described in Scheme IX. It will be appreciated by one skilled in the art that these compounds are regioisomeric with pyrazoles exemplified by compounds 14A,B and 39A,B in Scheme VIII. The preparation of 44A,B involves reaction of 43A,B with a Boc-protected hydrazine, followed by treatment with a strong acid, such as trifluoroacetic, hydrochloric acid and the like.

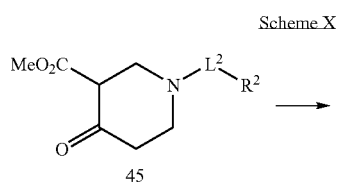

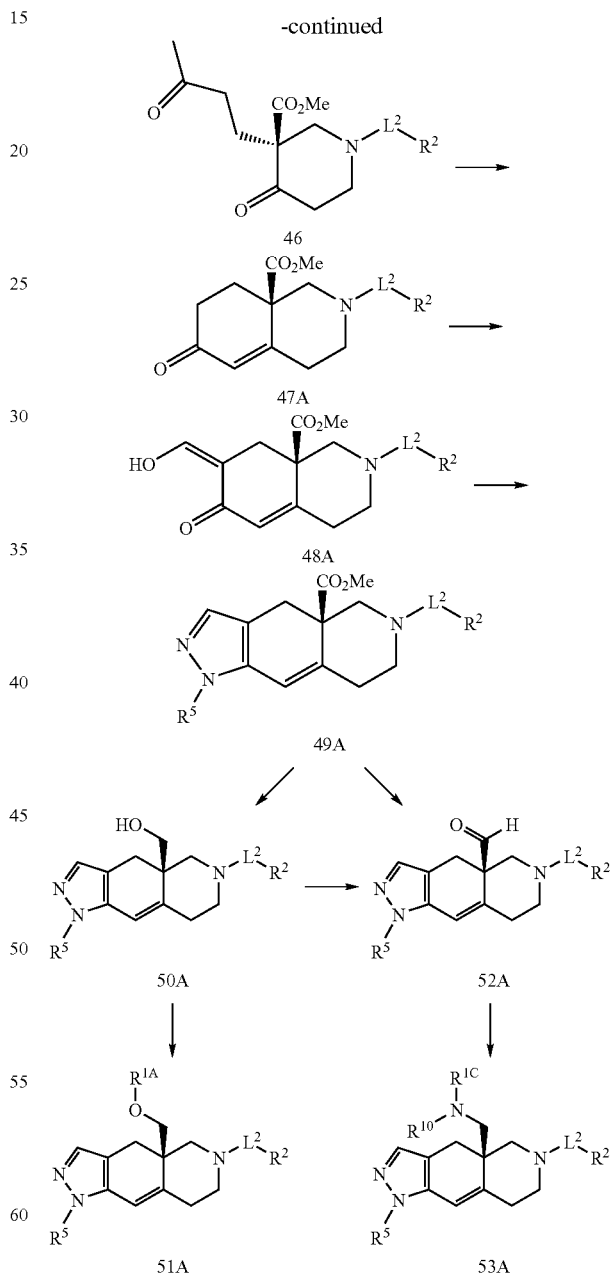

Compounds 49A-53A are prepared as described in Scheme X. In Scheme X, $R^5$, $R^{1A}$, $R^{1C}$, $R^{1D}$, $L^2$ and $R^2$ are as defined above in the compounds of the present invention. In Scheme X, $L^2$-$R^2$ can be replaced by a suitable protecting group, such as BOC or benzyl, to facilitate the synthesis. Keto-ester 45 is converted directly to enone 47A by a Robinson annelation reaction involving treatment of 45 with a base (e.g. potassium or sodium alkoxides) in an alcohol solvent (e.g. methanol, ethanol, or tert-butanol) followed by addition of methylvinyl ketone (MVK). The reaction is typically carried out at 0-25° C.

Alternatively, compounds 47A can be prepared in optically active form. The suitably N-protected piperidone-2-carboxylic acid ester 45 is heated with an optically active nitrogen-containing base (as described in *J. Med. Chem.* 39: 2302 (1996)) such as (R)-(+)-α-methylbenzylamine or (S)-2-amino-N,N-diethyl-3-methyl-butyramide, in a suitable solvent (such as toluene, benzene or dioxane) under dehydrating conditions (concentrated HCl, molecular sieves or Dean-Stark trap). The intermediate enamine is then treated with methylvinyl ketone in an apolar solvent such as acetone in the presence of copper$^{II}$ acetate to afford the optically active methylvinyl ketone adduct 46. Suitable N-protecting groups (Z) include benzyl and carbamate groups such as tert-butoxycarbonyl (Boc) and the like.

Optically active ketone 46 is converted to enone 47A by treatment with a base (e.g. potassium or sodium alkoxides) in an alcohol solvent (e.g. methanol, ethanol, or tert-butanol) or by addition of a nitrogen-containing base such as pyrrolidine, piperidine or morpholine in an aprotic solvent (e.g. benzene, toluene or dioxane).

Treatment of ketones 47A with a formylating agent such as ethyl formate or trifluoroethyl formate, as described for example in Organic Letters, 1 (7), 989, (1999), in the presence of a base such as sodium methoxide, LDA or sodium hydride in an aprotic solvent such as toluene affords hydroxymethylene derivatives 48A. Treatment of 48A with hydrazine, a protected alkyl hydrazine (as in Scheme IX) or an aryl hydrazine in an alcohol solvent or acetic acid with heating to the reflux temperature of the mixture affords pyrazoles 49A.

Alcohols 50A are prepared by treatment of ester 49A with a reducing agent such as DIBAL-H, LiAlH$_4$ or RED-AL in an inert solvent such as THF, benzene or toluene.

Alcohols 50A are converted into ether derivatives 51A by treatment with a base (e.g. sodium hydride) in an aprotic solvent (e.g. tetrahydrofuran, N,N-dimethylformamide) followed by addition of a substituted or unsubstituted alkyl, substituted or unsubstituted heteroalkyl, substituted or unsubstituted aryl, or substituted or unsubstituted heterocylalkyl halide.

Aldehyde intermediate 52A is prepared by reduction of ester 49A with a reducing agent such as DIBAL-H in toluene or dimethoxyethanol or sodium borohydride in ethanol or diglyme. Alternatively, compounds 52A are prepared from alcohols 50A by treatment with an oxidizing agent (e.g. chromium (VI) reagents such as pyridinium chlorochromate and pyridinium dichromate) in an aprotic solvent (e.g. dichloromethane); or using the Swern oxidation method (oxalyl chloride and dimethyl sulfoxide followed by addition of an organic base such as triethylamine).

Compounds 53A are prepared by reductive amination of aldehydes 52A with ammonia, a secondary amine, or a tertiary amine. The reaction is carried out by treatment of 52A with the amino component and a reducing agent (e.g. hydrogen, sodium borohydride or sodium cyanoborohydride) in a solvent such as tetrahydrofuran, ethanol, 1,2-dichloroethane and the like.

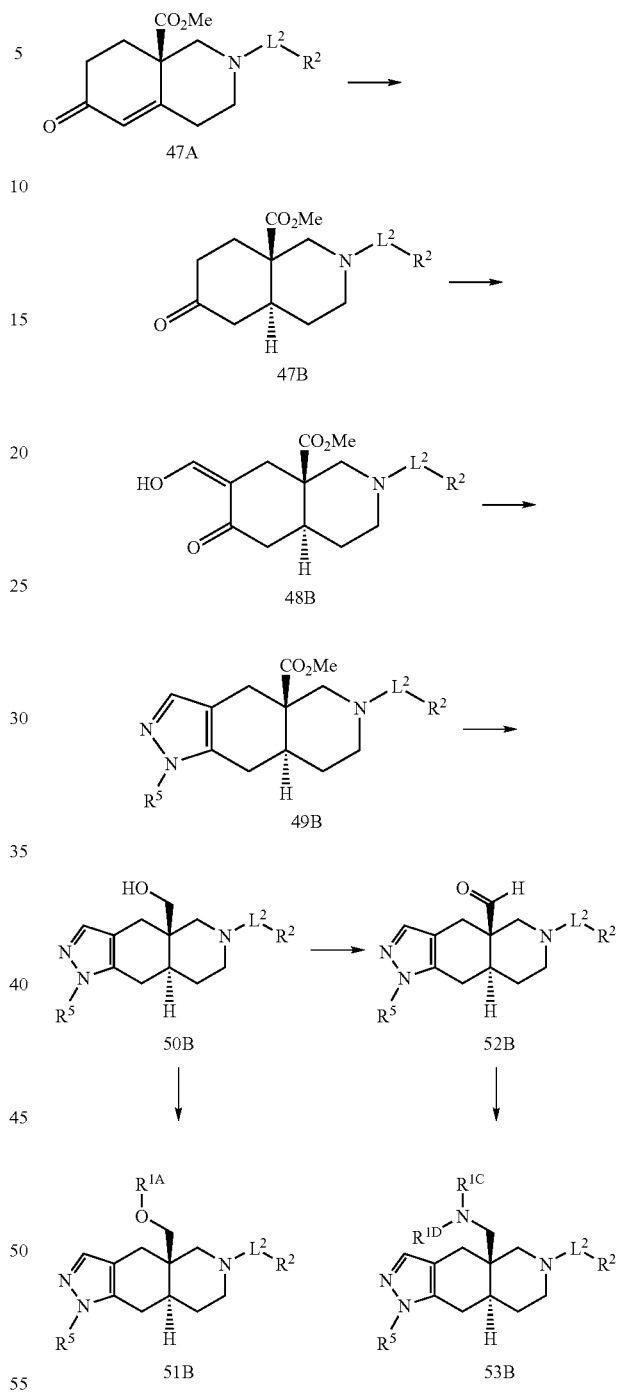

Saturated compounds 49B-53B are prepared as described in Scheme XI. It will be appreciated that Scheme XI exemplifies the synthesis of pyrazole derivatives; however, the synthesis of other heterocyclic examples such as those shown in Schemes III, IV and V can proceed analogously. Reduction of enone 47A to saturated ketone 47B is accomplished by catalytic hydrogenation using a catalyst such as palladium or platinum catalyst in an inert solvent, such as tetrahydrofuran or an alcohol such as ethanol, or using Raney nickel with hydrogen.

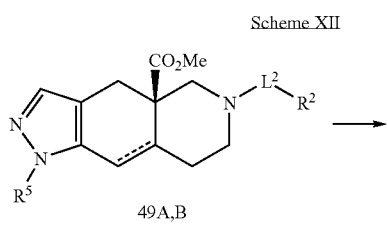

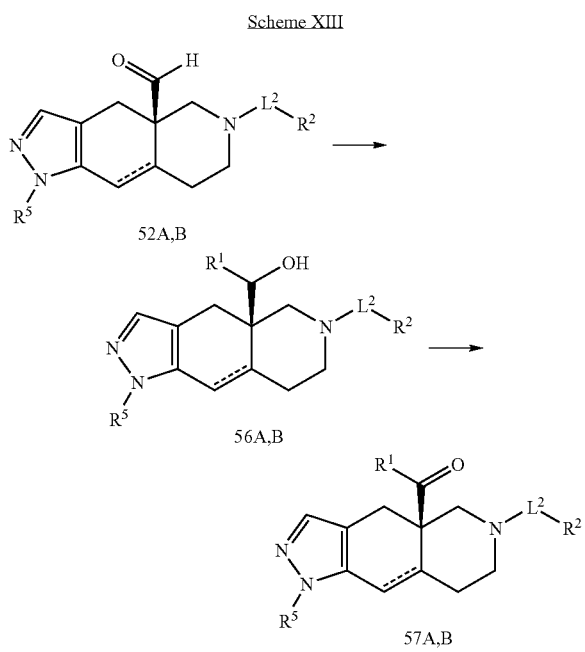

Compounds 56A,B may be prepared from aldehydes 52A,B by treatment with a suitable organometallic species, such as a Grignard reagent, an organocerium reagent or an organozinc reagent, in a solvent such as ether, THF or a similar aprotic solvent. Compounds 57A,B may be prepared from 56A,B using, for example, Swern oxidation conditions or an oxidizing agent such as $MnO_2$ in an inert solvent such as dichloromethane.

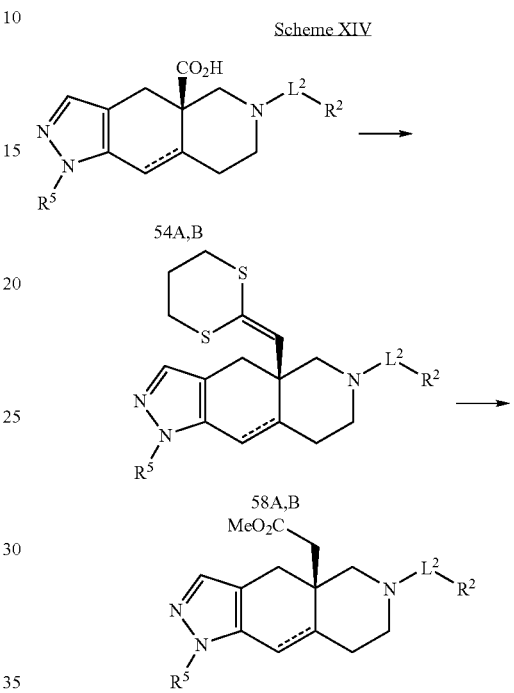

In Scheme XII, $R^5$, $R^{1C}$, $R^{1D}$, $L^2$ and $R^2$ are as defined above in the compounds of the present invention. Compounds 54A,B may be prepared from 49A,B by hydrolysis of the ester using aqueous solutions of lithium hydroxide or sodium hydroxide in alcoholic solvents such as ethanol or methanol. Amides 55A,B may be prepared from 54A,B and an amine using standard methods of amide bond formation, for example, EDC or HATU with an organic base such as diisopropylethylamine or triethylamine in an inert solvent such as dichloromethane.

In Scheme XIII, $R^5$, $L^2$, $R^1$ and $R^2$ are as defined above in the compounds of the present invention.

In Scheme XIV, $R^5$, $L^2$, $R^{1A}$, $R^{1C}$, $R^{1D}$ and $R^2$ are as defined above in the compounds of the present invention.

Thioketene acetals 58A,B may be prepared from acids 54A,B by treatment with 2-trimethylsilyl-1,3-dithiane and n-butyl lithium in an aprotic solvent such as THF. Typically, the chemistry is performed at −78° C. Esters 59A,B are formed by the treatment of 58A,B with mercury$^{II}$ chloride and perchloric acid in methanol.

Reduction of the ester in compounds 59A,B is achieved with a reducing agents such as DIBAL-H, LiAlH$_4$ or RED-AL in an inert solvent such as THF, benzene or toluene to afford alcohols 60A,B. Alcohols 60A,B are converted into ether derivatives 61A,B by treatment with a base (e.g. sodium hydride) in an aprotic solvent (e.g. tetrahydrofuran, N,N-dimethylformamide) followed by addition of a substituted or unsubstituted alkyl, substituted or unsubstituted heteroalkyl, substituted or unsubstituted aryl, or substituted or unsubstituted heterocycylalkyl halide.

Aldehydes 62A,B are prepared by reduction of esters 59A,B with a reducing agent such as DIBAL-H in toluene or dimethoxyethanol or sodium borohydride in ethanol or diglyme. Alternatively, compounds 62A,B are prepared from alcohols 60A,B by oxidation with an oxidizing agent (e.g. chromium (VI) reagents such as pyridinium chlorochromate and pyridinium dichromate) in an aprotic solvent (e.g. dichloromethane); or using the Swern oxidation method (oxalyl chloride and dimethyl sulfoxide followed by addition of an organic base such as triethylamine).

Amines 63A,b are prepared by reductive amination of aldehydes 62A,B with ammonia, a secondary amine, or a tertiary amine. The reaction is carried out by treatment of 62A,B with the amine component and a reducing agent (e.g. hydrogen, sodium borohydride or sodium cyanoborohydride) in a solvent such as tetrahydrofuran, ethanol, 1,2-dichloroethane and the like. Amines 63A,B could also be prepared by conversion of the alcohol group in 60A,B to a leaving group, such as a sulfonate or halide, followed by displacement of the leaving group with an amine.

Scheme XV

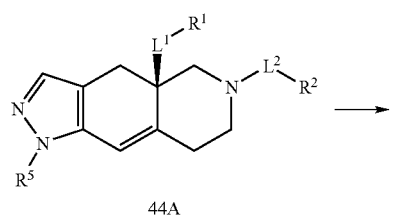

44A

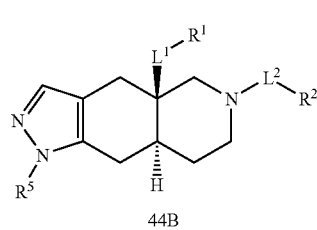

44B

Saturated compounds 44B can also prepared as described in Scheme XV. It will be appreciated that Scheme XV exemplifies the synthesis of pyrazole derivatives; however, the synthesis of other heterocyclic examples such as those shown in Schemes III, IV and V can proceed analogously. Reduction of enone 44A to saturated ketone 44B is accomplished by catalytic hydrogenation using a catalyst such as palladium or platinum catalyst in an inert solvent, such as tetrahydrofuran or an alcohol such as ethanol, or using Raney nickel with hydrogen.

Scheme XVI

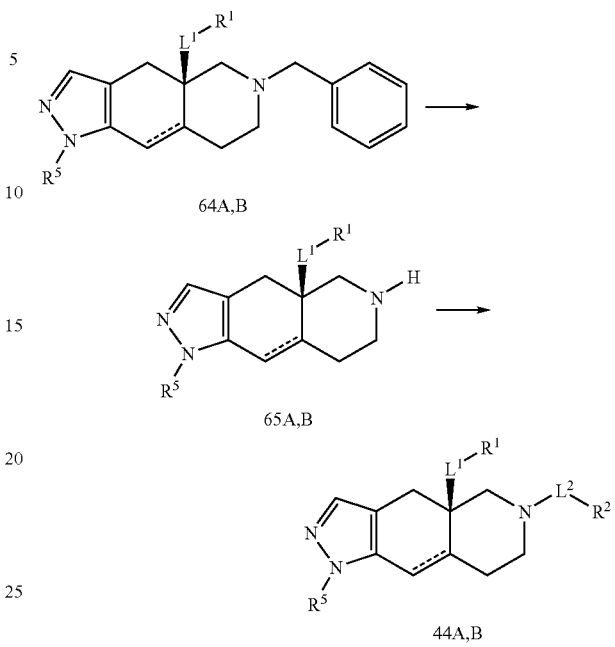

64A,B

65A,B

44A,B

Compounds 44A,B can also be prepared as shown in Scheme XVI by introducing the grouping L$^2$-R$^2$ into intermediates 65A,B which can be prepared from a protected amine of the type 64A,B. The conditions and procedures for these conversions are the same as those described for the preparations in Schemes I and II.

III. Assays and Methods for Modulating Glucocorticoid Receptor Activity

The compounds of the present invention can be tested for their antiglucocorticoid properties. Methods of assaying compounds capable of modulating glucocorticoid receptor activity are presented herein. Typically, compounds of the current invention are capable of modulating glucocorticoid receptor activity by selectively binding to the GR or by preventing GR ligands from binding to the GR. In some embodiments, the compounds exhibit little or no cytotoxic effect. Therefore, exemplary assays disclosed herein may test the ability of compounds to (1) bind to the GR; (2) selectively bind to the GR; (3) prevent GR ligands from binding to the GR; (4) modulate the activity of the GR in a cellular system; and/or (5) exhibit non-cytotoxic effects.

Binding Assays

In some embodiments, GR modulators are identified by screening for molecules that compete with a ligand of GR, such as dexamethasone. Those of skill in the art will recognize that there are a number of ways to perform competitive binding assays. In some embodiments, GR is pre-incubated with a labeled GR ligand and then contacted with a test compound. This type of competitive binding assay may also be referred to herein as a binding displacement assay. Alteration (e.g., a decrease) of the quantity of ligand bound to GR indicates that the molecule is a potential GR modulator. Alternatively, the binding of a test compound to GR can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B.V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a GR ligand and the binding agent can be GR bound to a solid phase. Alternatively, the labeled analyte can be labeled GR and the binding agent can be a solid phase GR ligand. The concentration of labeled analyte bound to the capture agent is inversely proportional to the ability of a test compound to compete in the binding assay.

Alternatively, the competitive binding assay may be conducted in liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the GR may be altered by the binding of the GR to its ligand or test compound. This alteration in the labeled GR results in a decrease or increase in the signal emitted by label, so that measurement of the label at the end of the binding assay allows for detection or quantitation of the GR in the bound state. A wide variety of labels may be used. The component may be labeled by any one of several methods. Useful radioactive labels include those incorporating $^3H$, $^{125}I$, $^{35}S$, $^{14}C$, or $^{32}P$. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art.

For competitive binding assays, the amount of inhibition may be determined using the techniques disclosed herein. The amount of inhibition of ligand binding by a test compound depends on the assay conditions and on the concentrations of ligand, labeled analyte, and test compound that are used. In an exemplary embodiment, a compound is said to be capable of inhibiting the binding of a GR ligand to a GR in a competitive binding assay if the inhibition constant ($K_i$) is less than 5 µM using the assay conditions presented in Example 63. In another exemplary embodiment, a compound is said to be capable of inhibiting the binding of a GR ligand to a GR in a competitive binding assay if the $K_i$ is less than 1 µM using the assay conditions presented in Example 63. In another exemplary embodiment, a compound is said to be capable of inhibiting the binding of a GR ligand to a GR in a competitive binding assay if the $K_i$ is less than 100 nM using the assay conditions presented in Example 63. In another exemplary embodiment, a compound is said to be capable of inhibiting the binding of a GR ligand to a GR in a competitive binding assay if the $K_i$ is less than 10 nM using the assay conditions presented in Example 63. In another exemplary embodiment, a compound is said to be capable of inhibiting the binding of a GR ligand to a GR in a competitive binding assay if the $K_i$ is less than 1 nM using the assay conditions presented in Example 63. In another exemplary embodiment, a compound is said to be capable of inhibiting the binding of a GR ligand to a GR in a competitive binding assay if the $K_i$ is less than 100 pM using the assay conditions presented in Example 63. In another exemplary embodiment, a compound is said to be capable of inhibiting the binding of a GR ligand to a GR in a competitive binding assay if the $K_i$ is less than 10 pM using the assay conditions presented in Example 63.

High-throughput screening methods may be used to assay a large number of potential modulator compounds. Such "compound libraries" are then screened in one or more assays, as described herein, to identify those library members (particular chemical species or subclasses) that display a desired characteristic activity. Preparation and screening of chemical libraries is well known to those of skill in the art. Devices for the preparation of chemical libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

Cell-Based Assays

Cell-based assays involve whole cells or cell fractions containing GR to assay for binding or modulation of activity of GR by a compound of the present invention. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemias, Burkitt's lymphomas, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, GR can be expressed in cells that do not express an endogenous version of GR.

In some cases, fragments of GR, as well as protein fusions, can be used for screening. When molecules that compete for binding with GR ligands are desired, the GR fragments used are fragments capable of binding the ligands (e.g., dexamethasone). Alternatively, any fragment of GR can be used as a target to identify molecules that bind GR. GR fragments can include any fragment of, e.g., at least 20, 30, 40, 50 amino acids up to a protein containing all but one amino acid of GR. Typically, ligand-binding fragments will comprise transmembrane regions and/or most or all of the extracellular domains of GR.

In some embodiments, signaling triggered by GR activation is used to identify GR modulators. Signaling activity of GR can be determined in many ways. For example, downstream molecular events can be monitored to determine signaling activity. Downstream events include those activities or manifestations that occur as a result of stimulation of a GR receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which exhibit glucocorticoid mediated upregulation of PEPCK and glucose-6-phosphate (G-6-Pase)). GRE-mediated gene expression has also been demonstrated in transfected cell lines using well-known GRE-regulated sequences (e.g. the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1beta stimulated IL-6 expression; the downregulation of collagenase, cyclooxygenase-2 and various chemokines (MCP-1, RANTES); or expression of genes regulated by NFkB or AP-1 transcription factors in transfected cell-lines. An example of a cell-based assay measuring gene transcription is presented in Example 65.

Typically, compounds that are tested in whole-cell assays are also tested in a cytotoxicity assay. Cytotoxicity assays are used to determine the extent to which a perceived modulating effect is due to non-GR binding cellular effects. In an exemplary embodiment, the cytotoxicity assay includes contacting a constitutively active cell with the test compound. Any decrease in cellular activity indicates a cytotoxic effect. An exemplary cytotoxicity assay is presented in Example 66.

Specificity

The compounds of the present invention may be subject to a specificity assay (also referred to herein as a selectivity assay). Typically, specificity assays include testing a compound that binds GR in vitro or in a cell-based assay for the degree of binding to non-GR proteins. Selectivity assays may be performed in vitro or in cell based systems, as described above. GR binding may be tested against any appropriate non-GR protein, including antibodies, receptors, enzymes, and the like. In an exemplary embodiment, the non-GR binding protein is a cell-surface receptor or nuclear receptor. In another exemplary embodiment, the non-GR protein is a steroid receptor, such as estrogen receptor, progesterone receptor, androgen receptor, or mineralocorticoid receptor. An exemplary specificity assay is presented in Example 64.

Methods of Modulating GR Activity

In another aspect, the present invention provides methods of modulating glucocorticoid receptor activity using the techniques described above. In an exemplary embodiment, the method includes contacting a GR with an effective amount of a compound of the present invention, such as the compound of Formula (I), and detecting a change in GR activity.

In an exemplary embodiment, the GR modulator is an antagonist of GR activity (also referred to herein as "a glucocorticoid receptor antagonist"). A glucocorticoid receptor antagonist, as used herein, refers to any composition or compound which partially or completely inhibits (antagonizes) the binding of a glucocorticoid receptor (GR) agonist (e.g. cortisol and synthetic or natural cortisol analog) to a GR thereby inhibiting any biological response associated with the binding of a GR to the agonist.

In a related embodiment, the GR modulator is a specific glucocorticoid receptor antagonist. As used herein, a specific glucocorticoid receptor antagonist refers to a composition or compound which inhibits any biological response associated with the binding of a GR to an agonist by preferentially binding to the GR rather than another nuclear receptor (NR). In some embodiments, the specific glucocorticoid receptor antagonist binds preferentially to GR rather than the mineralocorticoid receptor (MR) or progesterone receptor (PR). In an exemplary embodiment, the specific glucocorticoid receptor antagonist binds preferentially to GR rather than the mineralocorticoid receptor (MR). In another exemplary embodiment, the specific glucocorticoid receptor antagonist binds preferentially to GR rather than the progesterone receptor (PR).

In a related embodiment, the specific glucocorticoid receptor antagonist binds to the GR with an association constant ($K_d$) that is at least 10-fold less than the $K_d$ for the NR. In another embodiment, the specific glucocorticoid receptor antagonist binds to the GR with an association constant ($K_d$) that is at least 100-fold less than the $K_d$ for the NR. In another embodiment, the specific glucocorticoid receptor antagonist binds to the GR with an association constant ($K_d$) that is at least 1000-fold less than the $K_d$ for the NR.

In an exemplary embodiment, the present invention provides a method of treating a disorder or condition. The method includes modulating a glucocorticoid receptor by administering to a subject in need of such treatment, an effective amount of a compound of the present invention.

Methods of treating a disorder or condition through antagonizing a glucocorticoid receptor are also provided. The method includes administering to a subject in need of such treatment, an effective amount of a compound of the present invention.

In other embodiments, a method of modulating a glucocorticoid receptor is provided. The method includes the steps of contacting a glucocorticoid receptor with an effective amount of a compound of the present invention and detecting a change in the activity of the glucocorticoid receptor.

IV. Pharmaceutical Compositions of Glucocorticoid Receptor Modulators

In another aspect, the present invention provides pharmaceutical compositions including a pharmaceutically acceptable excipient and a compound of the present invention, such as the compound of Formula (I) provided above.

The compounds of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The GR modulators of this invention can also be administered by in intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and either a compound of Formula (I), or a pharmaceutically acceptable salt of a compound of Formula (I).

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a GR modulator in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The GR modulators of the invention can be delivered by transdermally, by a topical route, formulated as applicator sticks, solutions, suspensions, emulsions, gels, creams, ointments, pastes, jellies, paints, powders, and aerosols.

The GR modulators of the invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The GR modulator pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use In another embodiment, the GR modulator formulations of the invention are useful for parenteral administration, such as intravenous (IV) administration or administration into a body cavity or lumen of an organ. The formulations for administration will commonly comprise a solution of the GR modulator dissolved in a pharmaceutically acceptable carrier. Among the acceptable vehicles and solvents that can be employed are water and Ringer's solution, an isotopic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR modulator in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR modulator formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

V. Methods for Treating Conditions Mediated by Glucocorticoid Receptors

In another aspect, the present invention provides a method for the treatment of a disorder or condition through modulation of a glucocorticoid receptor. In this method, a subject in need of such treatment is administered an effective amount of a compound of the present invention. The amount is effective in modulating the glucocorticoids receptor.

A variety of disease states are capable of being treated with glucocorticoid receptor modulators of the present invention. Exemplary disease states include major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain (e.g. pain associate with gastroesophageal reflux disease), postpartum psychosis, postpartum depression, neurological disorders in premature infants, migraine headaches, obesity, diabetes, cardiovascular disease, hypertension, Syndrome X, depression, anxiety, glaucoma, human immunodeficiency virus (HIV) or acquired immunodeficiency syndrome (AIDS), neurodegeneration (e.g. Alzheimer's disease and Parkinson's disease), cognition enhancement, Cushing's Syndrome, Addison's Disease, osteoporosis, frailty, inflammatory diseases (e.g., osteoarthritis, rheumatoid arthritis, asthma and rhinitis), adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome post-surgical bone fracture, medical catabolism, and muscle frailty. The methods of treatment includes administering to a patient in need of such treatment, a therapeutically effective amount of a compound of the present invention, or a pharmaceutically acceptable salt thereof.

Thus, in an exemplary embodiment, the present invention provides a method of treating a disorder or condition through modulating a GR, the method includes administering to a subject in need of such treatment, an effective amount of a compound of the present invention, such as a compound of Formula (I).

The amount of GR modulator adequate to treat a disease through modulating the GR is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR modulator and disease or condition treated.

Single or multiple administrations of GR modulator formulations can be administered depending on the dosage and frequency as required and tolerated by the patient. The formulations should provide a sufficient quantity of active agent to effectively treat the disease state. Thus, in one embodiment, the pharmaceutical formulations for oral administration of GR modulator is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR modulator formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

After a pharmaceutical composition including a GR modulator of the invention has been formulated in an acceptable carrier, it can be placed in an appropriate container and labeled for treatment of an indicated condition. For administration of GR modulators, such labeling would include, e.g., instructions concerning the amount, frequency and method of administration. In one embodiment, the invention provides for a kit for the treatment of delirium in a human which includes a GR modulator and instructional material teaching the indications, dosage and schedule of administration of the GR modulator.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the GR modulator compounds are equally applicable to the methods of treating disease states and/or the pharmaceutical compositions described herein. All publications, patents, and patent applications cited herein are hereby incorporated by reference in their entirety for all purposes.

EXAMPLES

The following examples are provided solely to illustrate the present invention and are not intended to limit the scope of the invention, as described herein.

High Pressure Liquid Chromatography—Mass Spectrometry (LCMS) experiments to determine retention times (RT) and associated mass ions were performed using one of the following methods. Solvent A is water and solvent B is acetonitrile.

Method A: Experiments performed on a Micromass Platform LC spectrometer with positive and negative ion electrospray and ELS/Diode array detection using a Phenomenex Luna C18(2) 30×4.6 mm column and a 2 mL/minute flow rate. The solvent system was 95% solvent A and 5% solvent B for the first 0.50 minutes followed by a gradient up to 5% solvent A and 95% solvent B over the next 4 minutes. The final solvent system was held constant for a further 0.50 minutes.

Method B: Experiments performed on a Micromass Platform LCT spectrometer with positive ion electrospray and single wavelength UV 254 nm detection using a Higgins Clipeus C18 5 μm 100×3.0 mm column and a 2 mL/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 2 minutes.

Example 1

1,3-Dibenzyl-4-oxo-piperidine-3-carboxylic acid methyl ester (2: $R^{1B}$=H, Z=benzyl)

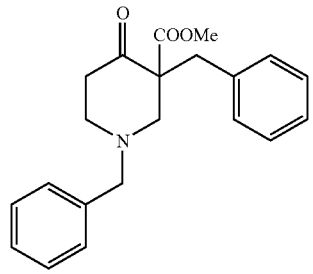

1-Benzyl-4-oxo-piperidine-3-carboxylic acid methyl ester hydrochloride salt (1, Z=benzyl) (15 g, 52.9 mmol) was suspended in DMF (150 mL) and cooled to 0° C. Sodium hydride (4.23 g, 105.8 mmol) was added portionwise over 1 h and the contents were allowed to warm to ambient temperature and stir for a further 1 h. Benzyl bromide (6.3 mL, 53.0 mmol) was added over 15 min and the contents were stirred for a further 68 h at ambient temperature. 10 mL of water were added and the contents were diluted with 400 mL of ethyl acetate, washed with water (200 mL), saturated sodium bicarbonate (200 mL) and brine (200 mL). The organic layer was dried over magnesium sulfate, filtered and concentrated to give 20.5 g yellow oil that was purified by flash column chromatography (3:2 cyclohexane/$CH_2Cl_2$ to 100% $CH_2Cl_2$) to give 17.52 g (98%) of the title compound as a colorless oil. LC-MS: RT=2.80 min. $(M+H)^+$ 338, $(M-OMe)^+$ 306.

Example 2

1,3-Dibenzylpiperidin-4-one (3: $R^{1B}$=H, Z=benzyl)

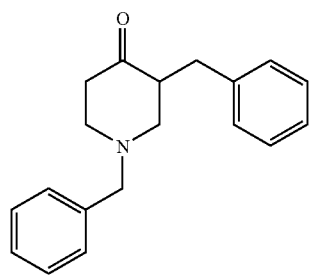

1,3-Dibenzyl-4-oxo-piperidine-3-carboxylic acid methyl ester, (2, $R^{1B}$=H, Z=benzyl) (17.52 g, 51.92 mmol) was suspended in 150 mL of 6N HCl:MeOH (5:1) and the mixture was heated to reflux temperature with stirring for 48 h. After cooling the mixture was basified to pH 10 with 6N NaOH and extracted with 3×200 mL dichloromethane. The combined organics were dried (MgSO$_4$) and concentrated to give 11.60 g of the title compound as a colorless oil, 80%. LC-MS: RT=0.38 min. (M+H)$^+$ 280.

Example 3

2,8a-Dibenzyl-1,3,4,7,8,8a-hexahydro-2H-isoquino-lin-6-one (4: R$^{1B}$=H, Z=benzyl)

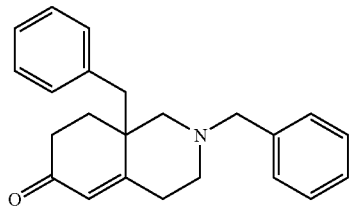

1,3-Dibenzylpiperidin-4-one (3, R$^{1B}$=H, Z=benzyl) (3.98 g, 13.96 mmol) was added to a solution of sodium methoxide (0.83 g, 15.36 mmol) in 80 mL of methanol and stirred at ambient temperature for 45 min. The contents were cooled to 0° C. and methylvinyl ketone (1.74 mL, 20.94 mmol) was added over 30 min. The contents were allowed to warm to ambient temperature and stir for 18 h. Concentrated HCl (1.55 mL) was added, the contents were stirred for a further 5 min and the solvents were evaporated to give a brown oil which was triturated in diethyl ether to give the title compound, 1.90 g. LC-MS: RT=2.26 min. (M+H)$^+$ 332.

Example 4

(R)-8a-Benzyl-6-oxo-3,4,6,7,8,8a-hexahydro-1H-isoquinoline-2-carboxylic acid tert-butyl ester (4: R$^{1B}$=H, Z=t-Butoxycarbonyl)

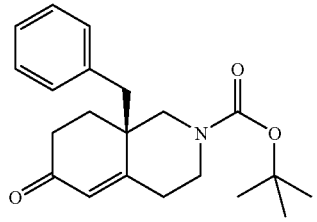

3-Benzyl-4-oxo-piperidine-1-carboxylic acid tert-butyl ester (1, Z=t-butoxycarbonyl) (11.50 g, 39.79 mmol) was dissolved in toluene (30 mL) and (R)-(+)-α-methylbenzylamine (6.15 mL, 47.75 mmol) was added. The contents were heated to reflux for 20 h (with a Dean-Stark trap) and then cooled to room temperature. The mixture was concentrated in vacuo and the resultant colorless oil (16.5 g, 39.79 mmol) was dissolved in toluene and cooled to 0° C. and methylvinyl ketone (4.0 mL, 47.45 mmol) was added dropwise. After 30 min the temperature was raised to 45° C. After 6 days at 45° C., acetic acid (20 mL) and water (20 mL) were added and the contents were stirred at ambient temperature for 1 h. The organics were extracted with CH$_2$Cl$_2$ (50 mL), washed with water, dried with MgSO$_4$, concentrated and purified by flash chromatography (CH$_2$Cl$_2$ 100% to 5% EtOAc in CH$_2$Cl$_2$) to afford 8.6 g of the intermediate diketone 3-benzyl-5-(1-hydroxy-1-methyl-propyl)-3-methyl-4-oxo-piperidine-1-carboxylic acid tert-butyl ester as a colorless oil. The intermediate diketone (900 mg, 2.50 mmol) was dissolved in methanol (14 mL) and sodium methoxide (20 mg, 1.30 mmol) was added and the contents were heated at 75° C. for 3 h. The contents were cooled to 0° C. and acetic acid (135 μL) was added. The volatiles were removed and the residue was partitioned between EtOAc (10 mL) and saturated NaHCO$_3$ solution. The organic phase was washed with brine and dried (MgSO$_4$). Purification by flash chromatography (CH$_2$Cl$_2$ 100% to 15% EtOAc in CH$_2$Cl$_2$) afforded 1.10 g of the title compound as a colorless oil. LC-MS (Method A): RT=3.84 min, (M+H)$^+$ no molecular ion seen.

Example 5

8a-Benzyl-1,3,4,7,8,8a-hexahydro-2H-isoquinolin-6-one (5A: R$^{1B}$=H)

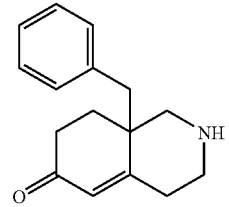

Compound 4 (R$^{1B}$=H, Z=benzyl) (3.0 g (9.05 mmol) and α-chloroethyl chloroformate (1.22 mL, 11.3 mmol) in dichloroethane (50 mL) were heated to reflux under nitrogen for 18 h. After cooling, the mixture was concentrated in vacuo. Methanol (50 mL) was added and the contents heated to reflux for 6 h. The solvents were removed by evaporation and the residue was purified by flash column chromatography (100% CH$_2$Cl$_2$ to CH$_2$Cl$_2$/MeOH 9:1) to give the title compound as a pale brown solid, 1.51 g. LC-MS: RT=1.67 min. (M+H)$^+$ 242

The following compounds were prepared according to the procedures described in Examples 1 to 4

8a-(3-Methoxybenzyl)-1,3,4,7,8,8a-hexahydro-2H-isoquinolin-6-one

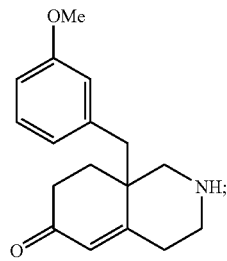

8a-(4-Methoxybenzyl)-1,3,4,7,8,8a-hexahydro-2H-isoquinolin-6-one

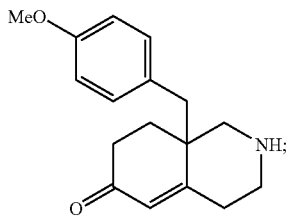

8a-(4-Bromobenzyl)-1,3,4,7,8,8a-hexahydro-2H-isoquinolin-6-one

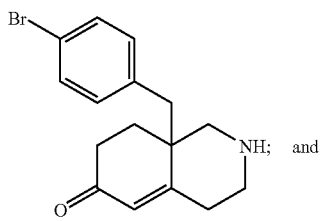

and 8a-(4-Nitrobenzyl)-1,3,4,7,8,8a-hexahydro-2H-isoquinolin-6-one

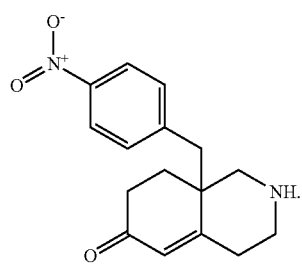

Example 6

2-Benzenesulfonyl-8a-benzyl-1,3,4,7,8,8a-hexahydro-2H-isoquinolin-6-one (10A: $R^{1B}$=H, $R^{2A}$=Ph)

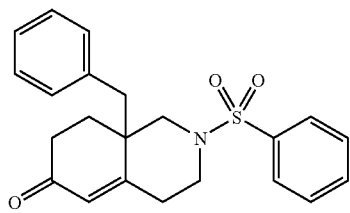

Benzenesulfonyl chloride (90.0 μmol) was added to a stirred solution of compound 5 ($R^{1B}$=H) (25.0 mg, 90.0 μmol), triethylamine (25.0 μL, 180 μmol) in 1,2-dichloroethane (3 mL). The resulting mixture was then stirred at room temperature for 18 h. PS-Trisamine resin (33.0 mg, loading=4.11 mmol/g) was added and the mixture was agitated at room temperature for a further 24 h. The mixture was filtered and the filtrate was purified by flash chromatography ($CH_2Cl_2$ 100% to 5% EtOAc in $CH_2Cl_2$) to afford the title compound 1 as a yellow oil, which solidified on standing. LC-MS: RT=3.68 min (M+H)+ 382.

Example 7

(R)-8a-Benzyl-2-(4-tert-butyl-benzenesulfonyl)-1,3,4,7,8,8a-hexahydro-2H-isoquinolin-6-one (10A: $R^{1B}$=H, $R^{2A}$=(4-t-Butyl)phenyl)

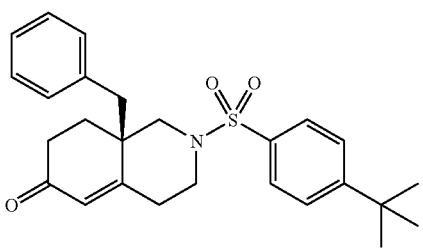

To compound (R)-5A ($R^{1B}$=H, Z=t-butoxycarbonyl) (598 mg, 1.75 mmol) was added a 20% solution of TFA in $CH_2Cl_2$ and the contents were stirred at ambient temperature for 2.5 h. The solvents were then removed in vacuo. The residue was dissolved in $CH_2Cl_2$ (5 mL) and diisopropylethylamine (670 μL, 3.86 mmol) and 4-t-butylphenylsulfonyl chloride (526 mg, 1.93 mmol) were added and the contents were stirred for 18 h. Water (10 mL) was added and the organics were extracted with EtOAc (15 mL), washed with brine and dried ($MgSO_4$). Purification by flash chromatography ($CH_2Cl_2$ 100% to 5% EtOAc in $CH_2Cl_2$) afforded 600 mg of the title compound as an orange oil. LC-MS (Method A): RT=4.06 min, (M+H)+ 438.

Example 8

2,8aβ-Dibenzyl-1,3,4,4aα,5,7,8,8a-octahydro-2H-isoquinolin-6-one (6B: $R^{1B}$=H, $R^2$=Phenyl)

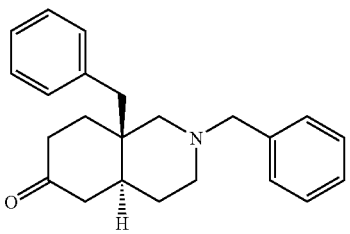

Lithium metal (150 mg) was added to a flask charged with 75 mL of liquid ammonia. 2,8a-Dibenzyl-1,3,4,7,8,8a-hexahydro-2H-isoquinolin-6-one (4, $R^{1B}$=H, Z=benzyl) (2.0 g) was added and the contents were stirred at −78° C. for 20 min. A further 150 mg of lithium metal was added and stirring continued for a further 15 min. Solid ammonium chloride was added until the blue color was discharged. The contents were warmed to ambient temperature and extracted with dichloromethane. The organic phase was washed with saturated. ammonium chloride, dried and concentrated to give a residue that was purified by flash column chromatography (10% EtOAc in $CH_2Cl_2$) to give 0.60 g of the title compound. LC-MS: RT=2.15 min. (M+H)+ 334.

Example 9

8aβ-Benzyl-1,3,4,4aα,5,7,8,8a-octahydro-2H-isoquinolin-6-one (5B: $R^{1B}$=H)

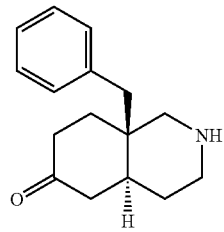

Compound 6B ($R^{1B}$=H, $R^2$=Ph) (1.14 g, 3.42 mmol) and palladium hydroxide (0.35 g, 0.342 mmol) were suspended in 40 mL of acetic acid and hydrogenated at atmospheric pressure for 21 h. The reaction mixture was filtered, concentrated and dissolved in $CH_2Cl_2$ and treated with 1M HCl in diethyl ether to give the title compound as its hydrochloride salt, a beige solid, 0.96 g. LC-MS RT=1.67 min. $(M+H)^+$ 244.

Example 10

2-Benzenesulfonyl-8aβ-benzyl-1,3,4,4a,α,5,7,8,8a-octahydro-2H-isoquinolin-6-one (10B: $R^{1B}$=H, $R^{2A}$=Phenyl)

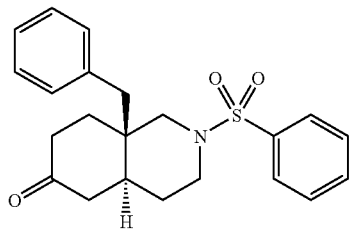

8aβ-Benzyl-1,3,4,4aα,5,7,8,8a-octahydroisoquinolin-6-one (5B: $R^{1B}$=H) (84 mg, 0.348 mmol) and benzenesulfonyl chloride (49 μL, 0.383 mmol) were stirred in $CH_2Cl_2$ and diisopropylethylamine (73 μL) was added. The contents were stirred for 18 h, diluted with $CH_2Cl_2$, washed with water, brine, dried, concentrated and purified by flash column chromatography (10% EtOAc in $CH_2Cl_2$) to give the title compound as a waxy pale yellow solid (83 mg). LC-MS: RT=3.24 min. $(M+H)^+$ 384.

The following compound was similarly prepared:

8aβ-Benzyl-2-(4-tert-butylbenzenesulfonyl)-1,3,4,4aα,5,7,8,8a-octahydro-2H-isoquinolin-6-one

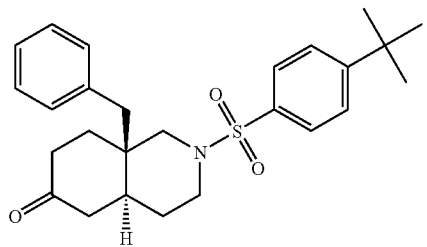

Example 11

2,8a-Dibenzyl-7-[1-hydroxy-meth-(Z)-ylidene]-1,3,4,7,8,8a-hexahydro-2H-isoquinolin-6-one (12A: $R^{1B}$=H, $L^2$-$R^2$=Benzyl)

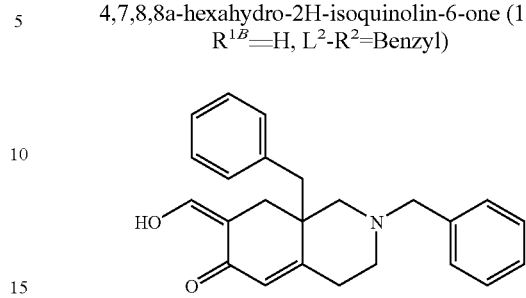

Compound 6A ($R^{1B}$=H, $L^2$-$R^2$=benzyl) (0.31 g, 0.94 mmol) was dissolved in toluene (2.5 mL). Ethyl formate (152 μL, 1.88 mmol) was added followed by sodium methoxide (102 mg, 1.88 mmol). The contents were heated to reflux for 90 min, then cooled, poured into water and extracted with $CH_2Cl_2$. The organic phase was washed with brine and dried ($MgSO_4$). Removal of solvent gave 334 mg of the title compound as an orange oil which was used in subsequent examples without further purification. LC-MS (Method A): RT=2.33 min, $(M+H)^+$ 360.

Example 12

8a-Benzyl-2-(4-tert-butylbenzenesulfonyl-7-hydroxymethylene-1,3,4,7,8,8a-hexahydro-2H-isoquinolin-6-one (12A: $R^{1B}$=H, $L^2$-$R^2$=$SO_2$(4-t-Butyl)phenyl)

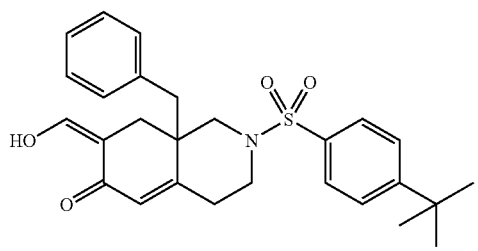

Compound 10A ($R^{1B}$=H; $R^{2A}$=(4-t-butyl)phenyl) (100 mg, 0.229 mmol) was dissolved in toluene (1 mL). Ethyl formate (37 μL, 0.46 mmol) was added followed by sodium methoxide (25 mg, 0.46 mmol). The contents were heated to reflux for 35 min, then cooled, poured into water and extracted with $CH_2Cl_2$. The organic phase was washed with brine and dried ($MgSO_4$). Removal of solvent gave 113 mg of the title compound as an orange glass which was used in subsequent examples without further purification. LC-MS: RT=4.36 min. $(M+H)^+$ 466, $(M-H)^-$ 464.

Example 13

(S)-8a-Benzyl-2-(4-tert-butyl-benzenesulfonyl)-7-[1-hydroxy-meth-(Z)-ylidene]-1,3,4,7,8,8a-hexahydro-2H-isoquinolin-6-one (12A: $R^{1B}$=H, $L^2$-$R^2$=SO$_2$(4-t-Butyl)phenyl)

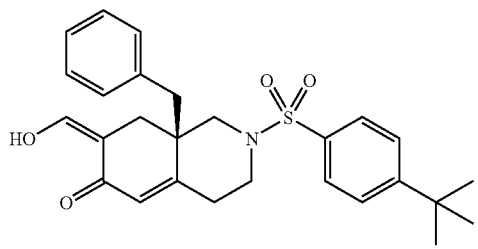

Compound (R)-10A ($R^{1B}$=H, $R^{2A}$=(4-t-butyl)phenyl) (665 mg, 1.52 mmol) was dissolved in methanol (5 mL) and sodium methoxide (234 mg, 4.35 mmol) and ethyl formate (450 μL, 7.60 mmol) were added. After 1 h, water (5 mL) was added and the organics were extracted with EtOAc, washed with brine and dried (MgSO$_4$). Removal of solvent gave 532 mg of the title compound as an orange foam which was used in subsequent examples without further purification. LC-MS (Method A): RT=4.40 min, (M+H)$^+$ 466.

Example 14

8a-Benzyl-2-(4-tert-butylbenzenesulfonyl)-7-hydroxymethylene-octahydroisoquinolin-6-one. (12B: $R^{1B}$=H, $L^2$-$R^2$=SO$_2$(4-t-Butyl)phenyl)

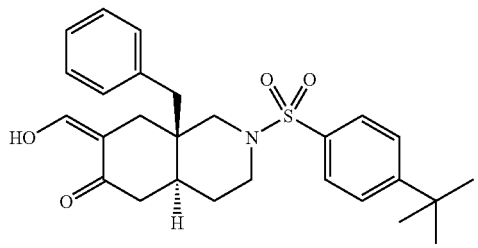

Compound 10B ($R^{1B}$=H; $R^{2A}$=(4-t-butylphenyl)) (100 mg, 0.228 mmol) was dissolved in toluene (1 mL) and ethyl formate (25 mg, 0.46 mmol) was added followed by sodium methoxide (25 mg, 0.46 mmol). The contents were heated to reflux for 35 min, then cooled, poured into water and extracted with CH$_2$Cl$_2$. The organics were washed with brine, dried (MgSO$_4$) and concentrated to give the title compound together with the 5-hydroxymethylene regioisomer which were used directly in the following Examples without further purification. LC-MS: RT=4.46 min. (M+H)$^+$ 468.

Example 15

4a-Benzyl-6-(4-tert-butylbenzenesulfonyl)-4,4a,5,6,7,8-hexahydro-1H-1,2,6-triazacyclopenta[b]naphthalene. (13A: $R^{1B}$=H, $L^2$-$R^2$=SO$_2$(4-t-Butyl)phenyl)

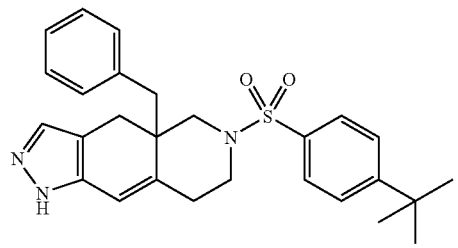

Compound 12A ($R^{1B}$=H, $L^2$-$R^2$=SO$_2$(4-t-butyl)Ph) (23 mg, 49.5 μmol) was suspended in ethanol (1 mL) and hydrazine hydrate (10 μL, 0.32 mmol) was added and the contents were heated to reflux for 1.5 h. The volatiles were removed under vacuum to give 40 mg of an orange glass that was purified by preparative HPLC to yield the title compound as a colorless glass, 10 mg. LC-MS: RT=4.12 min. (M+H)$^+$ 462.

The following compounds were similarly prepared:

4a-Benzyl-6-(4-morpholin-4-yl-benzenesulfonyl)-4,4a,5,6,7,8-hexahydro-1H-1,2,6-triaza-cyclopenta[b]naphthalene

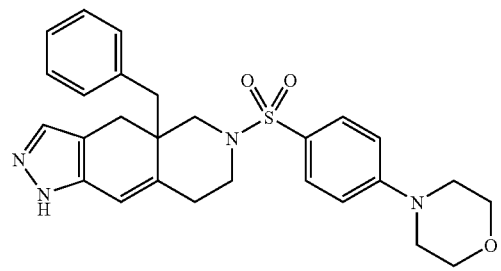

LC-MS (Method A): RT=3.15 min, (M+H)$^+$ 491.

4a-Benzyl-6-(4-methyl-3,4-dihydro-2H-benzo[1,4]oxazine-7-sulfonyl)-4,4a,5,6,7,8-hexahydro-1H-1,2,6-triaza-cyclopenta[b]naphthalene

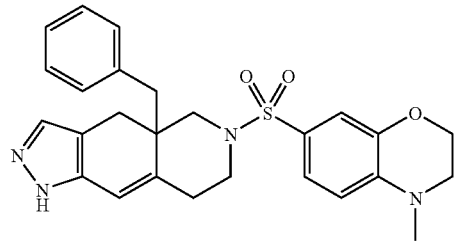

LC-MS (Method A): RT=3.51 min, (M+H)$^+$ 477.

Example 16

4a-Benzyl-6-(4-tert-butylbenzenesulfonyl)-2-methyl-4,4a,5,6,7,8-hexahydro-2H-1,2,6-triazacyclopenta[b]naphthalene. (14A: $R^{1B}$=H, $L^2$-$R^2$=$SO_2$(4-t-Butyl)phenyl, $R^{6C}$=Me)

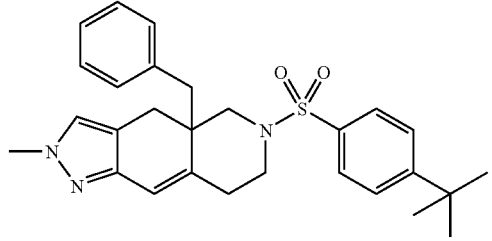

Compound 12A ($R^{1B}$=H, $L^2$-$R^2$=$SO_2$(4-t-butyl)phenyl) (20 mg, 43 µmol) was suspended in ethanol (1 mL) and methyl hydrazine (15 µL, 0.28 mmol) was added. The contents were heated to 90° C. for 1.5 h, then cooled and evaporated to give 22 mg of an orange glass. Purification by preparative HPLC yielded the title compound: 3.5 mg as a yellow glass. LC-MS: RT=4.39 min. (M+H)⁺ 476.

Example 17

4a-Benzyl-6-(4-tert-butylbenzenesulfonyl)-1-(4-fluorophenyl)-4,4a,5,6,7,8-hexahydro-1H-1,2,6-triazacyclopenta[b]naphthalene. (15A: $R^{1B}$=H, $L^2$-$R^2$=$SO_2$(4-t-Butyl)phenyl)

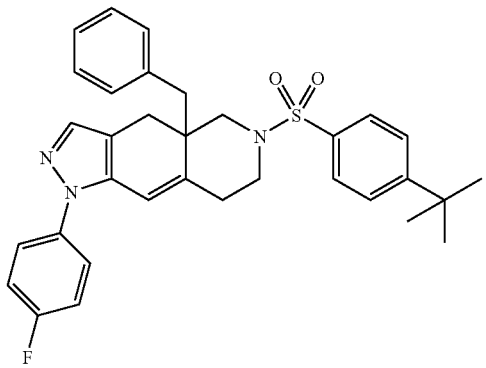

Compound 12A ($R^{1B}$=H, $L^2$-$R^2$=$SO_2$(4-t-butyl)phenyl) (28 mg, 60.2 µmol), 4-fluorophenylhydrazine hydrochloride (10.8 mg, 66.2 µmol) and sodium acetate (5.4 mg, 66.2 µmol) were dissolved in acetic acid (0.8 mL) and heated to 90° C. for 18 h. The contents were cooled, poured into water, extracted with $CH_2Cl_2$, dried ($MgSO_4$) and concentrated to give 41 mg of red-brown oil that was purified by preparative HPLC to give the title compound as an orange-brown glass, 8 mg. LC-MS: RT=4.85 min. (M+H)⁺ 556.

The following compounds were similarly prepared:

(S)-4a-Benzyl-6-(4-tert-butyl-benzenesulfonyl)-1-(4-fluoro-phenyl)-4,4a,5,6,7,8-hexahydro-1H-1,2,6-triaza-cyclopenta[b]naphthalene

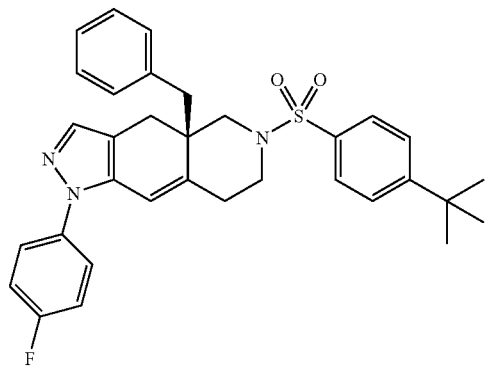

(S)-4a-Benzyl-6-(4-tert-butyl-benzenesulfonyl)-1-(4-methoxy-phenyl)-4,4a,5,6,7,8-hexahydro-1H-1,2,6-triaza-cyclopenta[b]naphthalene

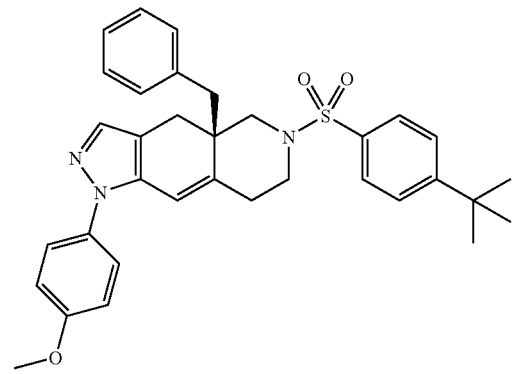

LC-MS (Method A): RT=4.78 min, (M+H)⁺ 568.

(S)-4a-Benzyl-6-(4-tert-butyl-benzenesulfonyl)-1-p-tolyl-4,4a,5,6,7,8-hexahydro-1H-1,2,6-triaza-cyclopenta[b]naphthalene

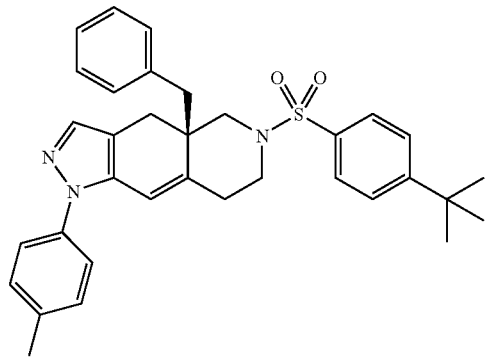

LC-MS (Method A): RT=4.96 min, (M+H)⁺ 552.

63

1,4a-Dibenzyl-6-(4-tert-butyl-benzenesulfonyl)-4,4a,5,6,7,8-hexahydro-1H-1,2,6-triaza-cyclopenta[b]naphthalene

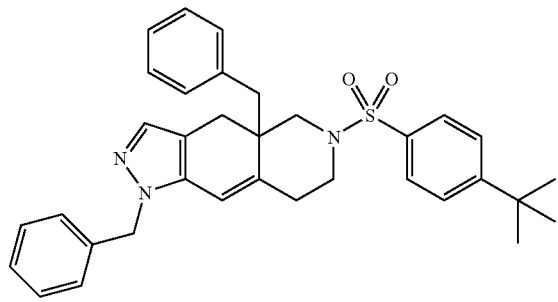

LC-MS (Method A): RT=4.73 min, (M+H)⁺ 552.

4a-Benzyl-6-(4-tert-butyl-benzenesulfonyl)-1-(4-trifluoromethyl-phenyl)-4,4a,5,6,7,8-hexahydro-1H-1,2,6-triaza-cyclopenta[b]naphthalene

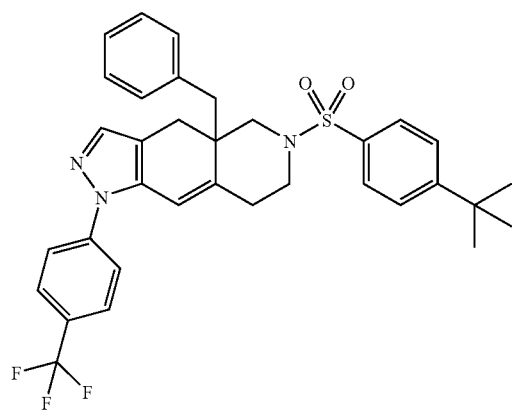

LC-MS (Method A): RT=5.03 min, (M+H)⁺ 606.

4-[4a-Benzyl-6-(4-tert-butyl-benzenesulfonyl)-4,4a,5,6,7,8-hexahydro-1,2,6-triaza-cyclopenta[b]naphthalen-1-yl]-benzonitrile

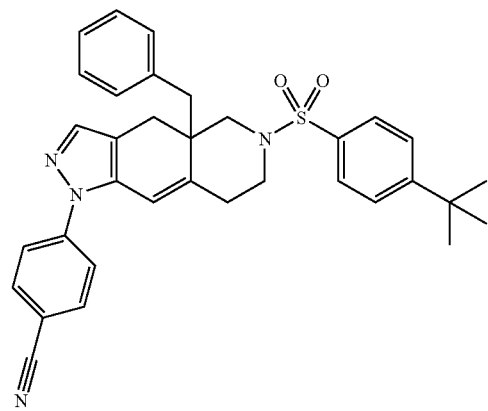

LC-MS (Method A): RT=4.74 min, (M+H)⁺ 563.

64

4-[4a-Benzyl-6-(4-tert-butyl-benzenesulfonyl)-4,4a,5,6,7,8-hexahydro-1,2,6-triaza-cyclopenta[b]naphthalen-1-yl]-benzenesulfonamide

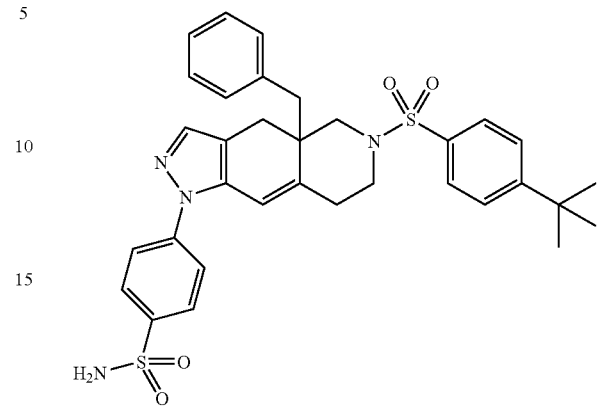

LC-MS (Method A): RT=4.25 min, (M+H)⁺ 617.

3-[4a-Benzyl-6-(4-tert-butyl-benzenesulfonyl)-4,4a,5,6,7,8-hexahydro-1,2,6-triaza-cyclopenta[b]naphthalen-1-ylmethyl]-phenol

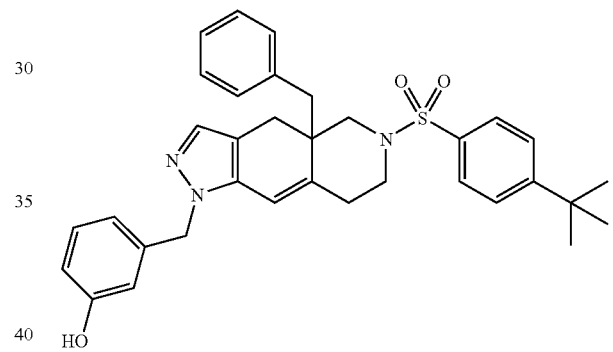

LC-MS (Method A): RT=4.33 min, (M+H)⁺ 568.

Example 18

4a,6-Dibenzyl-1-(4-fluoro-phenyl)-4,4a,5,6,7,8-hexahydro-1H-1,2,6-triaza-cyclopenta[b]naphthalene (15A: R$^{1B}$=H, L$^{2}$-R$^{2}$=benzyl)

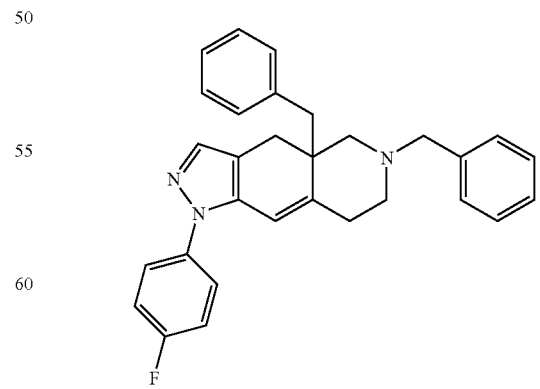

Compound 12A (R$^{1B}$=H, L$^{2}$-R$^{2}$=benzyl) (167 mg, 0.47 mmol) and 4-fluorophenylhydrazine hydrochloride (163 mg, 2.79 mmol) were dissolved in acetic acid (2.5 mL) and heated to 90° C. for 2 hours. The contents were cooled, poured into water, extracted with $CH_2Cl_2$, dried ($MgSO_4$) and concentrated. Purification by flash chromatography ($CH_2Cl_2$ 100% to 15% EtOAc in $CH_2Cl_2$) afforded 41 mg of the title compound as an orange oil. LC-MS (Method A): RT=2.75 min, $(M+H)^+$ 450.

The following compounds were similarly prepared:

6-Benzyl-4a-(4-fluoro-benzyl)-1-(4-fluoro-phenyl)-4,4a,5,6,7,8-hexahydro-1H-1,2,6-triaza-cyclopenta[b]naphthalene

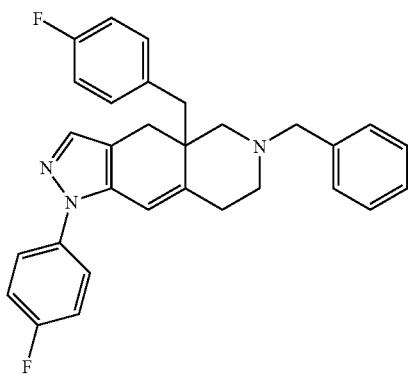

LC-MS (Method A): RT=2.80 min, $(M+H)^+$ 468.

6-Benzyl-1-(4-fluoro-phenyl)-4a-(4-methoxy-benzyl)-4,4a,5,6,7,8-hexahydro-1H-1,2,6-triaza-cyclopenta[b]naphthalene

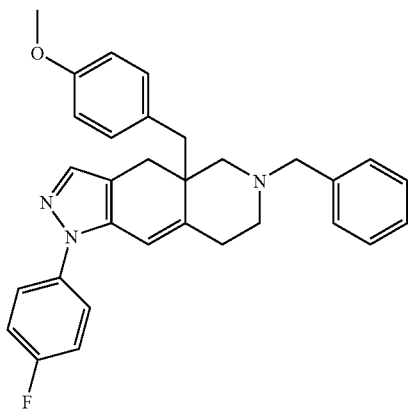

LC-MS (Method A): RT=2.69 min, $(M+H)^+$ 480.

Example 19

4a-Benzyl-6-(4-tert-butylbenzenesulfonyl)-4,4a,5,6,7,8-hexahydro-1-oxa-2,6-diazacyclopenta[b]naphthalene. (16A: $R^{1B}$=H, $L^2$-$R^2$=$SO_2$(4-t-Butyl)phenyl)

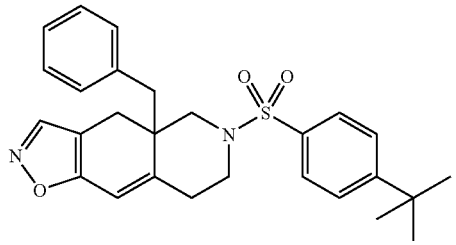

Compound 12A ($R^{1B}$=H, $L^2$-$R^2$=$SO_2$(4-t-butyl)phenyl) (21 mg, 45 µmol) and hydroxylamine sulfate (4 mg, 22.5 µmol) were dissolved in ethyl acetate (1 mL), acetic acid (0.2 mL) and water (0.1 mL) and heated to 90° C. for 19 h. The contents were evaporated to dryness and purified by preparative HPLC to yield the title compound, 0.9 mg. LC-MS: RT=4.49 min. $(M+H)^+$ 463.

Example 20

10a-Benzyl-6-(4-tert-butyl-benzenesulfonyl)-2-methyl-5,6,7,8,10,10a-hexahydro-1,3,6-triaza-anthracene (17A: $R^{6D}$=Methyl; $R^{1B}$=H; $L^2$-$R^2$=$SO_2$(4-t butylphenyl)

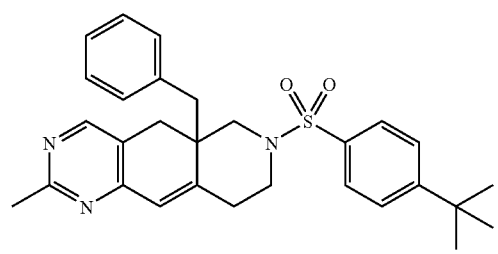

Compound 12A ($R^{1B}$=H; $L^2$-$R^2$=$SO_2$(4-t-butylphenyl) (50 mg, 0.11 mmol) was heated with acetamidine hydrochloride (61 mg, 0.65 mmol) in DMF (0.5 mL) at 180° C. using microwave irradiation for 10 min. Water (5 mL) was added and the organics were extracted with $CH_2Cl_2$ (3×5 mL) and washed with brine and dried ($MgSO_4$). Purification by preparative HPLC afforded 6 mg of the title compound as a yellow oil. LC-MS (Method A): RT=4.01 min, $(M+H)^+$ 488.

Example 21

4a-Benzyl-6-(4-tert-butylbenzenesulfonyl)-4,4a,5,6,7,8,8a,9-octahydro-2H-1,2,6-triazacyclopenta[b]naphthalene. (13B: $R^{1B}$=H, $L^2$-$R^2$=SO$_2$(4-t-Butyl)phenyl)

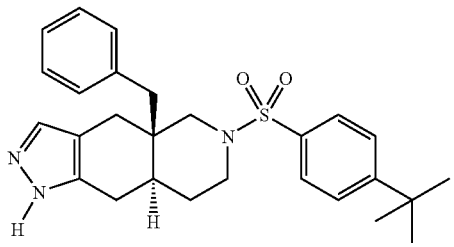

The mixture of compound 12B ($R^{1B}$=H, $L^2$-$R^2$=SO$_2$(4-t-butyl)phenyl) and its regioisomer (29 mg, 42.8 μmol), hydrazine hydrate (9 μL, 0.278 mmol) and ethanol (1 mL) were heated at 90° C. for 1.5 h. The volatiles were removed under vacuum to give 21 mg of a glass that was purified by preparative HPLC to give the title compound as an off-white solid, 16 mg. LC-MS: RT=4.03 min. ((M+H)$^+$ 464.

Example 22

4a-Benzyl-6-(4-tert-butylbenzenesulfonyl)-1-(4-fluorophenyl)-4,4a,5,6,7,8,8a,9-octahydro-1H-1,2,6-triazacyclopenta[b]naphthalene. (15B: $R^{1B}$=H, $L^2$-$R^2$=SO$_2$(4-t-Butyl)phenyl)

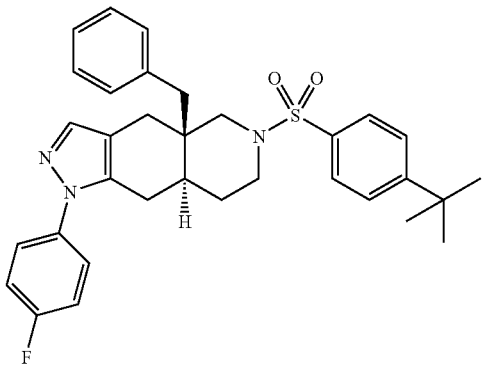

The mixture of compound 12B ($R^{1B}$=H, $L^2$-$R^2$=SO$_2$(4-t-butyl)phenyl) and its regioisomer (20 mg, 42.8 μmol) and 4-fluorophenylhydrazine hydrochloride (7.6 mg, 47.1 μmol)) were dissolved in acetic acid and sodium acetate (4 mg, 47.1 μmol) added. The contents were heated to 90° C. for 16 h, then cooled and poured into water and extracted with CH$_2$Cl$_2$. The organics were washed with brine, dried (MgSO4) and concentrated to give 22 mg crude product which was purified by preparative HPLC to yield the title compound as a brown glass, 11 mg. LC-MS: RT=4.93 mins. (M+H)$^+$ 558.

Example 23

4a-Benzyl-6-(4-tert-butylbenzenesulfonyl)-4,4a,5,6,7,8,8a,9-octahydro-1-oxa-2,6-diazacyclopenta[b]naphthalene. (16B: $R^{1B}$=H, $L^2$-$R^2$=SO$_2$(4-t-Butyl)phenyl)

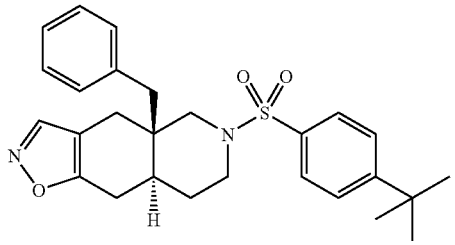

The mixture of compound 12B ($R^{1B}$=H, $L^2$-$R^2$=SO$_2$(4-t-butyl)phenyl) and its regioisomer (20 mg, 42.8 μmol) were dissolved in ethanol (0.6 mL) and acetic acid (0.2 mL) and water (0.1 mL) were added, followed by hydroxylamine hydrochloride (3.8 mg, 54.6 μmol). The contents were heated to 90° C. for 19 h, the volatiles were removed and the residue was purified by preparative HPLC to yield the title compound as an off-white solid, 7 mg. LC-MS: RT=4.47 min. (M+H)+ 465

Example 24

(R)-7-Acetoxy-2-(4-tert-butyl-benzenesulfonyl)-6-oxo-2,3,4,6,7,8-hexahydro-1H-isoquinoline-8a-carboxylic acid methyl ester (24A: $L^1$-$R^1$=CO$_2$Me, $L^2$-$R^2$=SO$_2$(4-t-Butyl)phenyl)

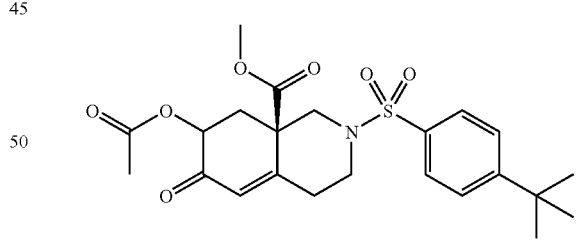

To a solution of compound (R)-23A ($L^1$-$R^1$=CO$_2$Me; $L^2$-$R^2$=SO$_2$(4-t-butyl)phenyl)) (1.00 g, 2.47 mmol) in toluene (50 mL) was added manganese acetate dihydrate (3.69 g, 13.79 mmol). The contents were heated for 18 h at reflux under a Dean-Stark trap. The solvents were removed and the residue was purified by flash chromatography (CH$_2$Cl$_2$ 100% to 5% EtOAc in CH$_2$Cl$_2$) to afford 775 mg of the title compound as an off white solid. LC-MS (Method A): RT=3.82 min, (M+H)$^+$ 464.

Example 25

(R)-6-(4-tert-Butyl-benzenesulfonyl)-2-methyl-1,4,5,6,7,8-hexahydro-1,3,6-triaza-cyclopenta[b]naphthalene-4a-carboxylic acid methyl ester (25A: L¹-R¹=CO₂Me; L²-R²=SO₂(4-t-Butyl)phenyl)

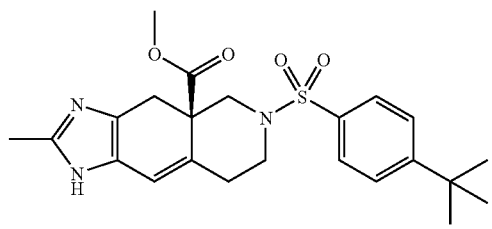

To a solution of compound 24A (L¹-R¹=CO₂Me; L²-R²=SO₂(4-t-butyl)phenyl)) (600 mg, 1.29 mmol) in ethanol (4 mL) was added copper^II acetate (470 mg, 2.59 mmol), aqueous ammonia (3 mL) and acetaldehyde (5 mL) and the contents were heated for 5 h at reflux. The solvents were removed, NaHCO₃ (20 mL) was added, and the organics were extracted with CH₂Cl₂ (20 mL), washed with brine and dried (MgSO₄). Purification by flash chromatography (CH₂Cl₂ 100% to 5% EtOAc in CH₂Cl₂) afforded 432 mg of the title compound as an off white solid. LC-MS (Method A): RT=2.53 min, (M+H)⁺ 444.

Example 26

(S)-8a-Methyl-6-oxo-3,4,6,7,8,8a-hexahydro-1H-isoquinoline-2-carboxylic acid tert-butyl ester (36A: L²-R²=CO₂-t-Butyl)

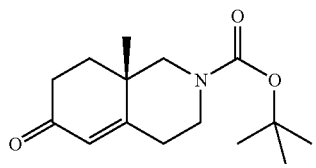

1-Benzyl-3-methyl-piperidin-4-one (15.0 g, 73.89 mmol) was dissolved in toluene (150 mL) and (R)-(+)-α-methylbenzylamine (11.4 mL, 88.67 mmol) was added. The contents were heated to reflux for 20 h (Dean-Stark trap) and then cooled to room temperature. The resultant colorless oil was dissolved in THF and methylvinylketone (7.40 mL, 88.67 mmol) and hydroquinone (150 mg, catalytic) were added and the contents were stirred in the dark. After 2 days 1N HCl (90 mL) was added and the contents stirred at ambient temperature for 30 min, the organics were extracted with diethyl ether (100 mL), washed with water, dried with MgSO₄, concentrated and purified by flash chromatography (CH₂Cl₂ 100% to 20% EtOAc in CH₂Cl₂) to afford 6.51 g of ((R)-1-benzyl-3-methyl-3-(3-oxo-butyl)-piperidin-4-one as a colorless oil. LC-MS (Method A): RT=0.32 min, (M+H)⁺ 274.

This material (6.5 g, 23.80 mmol) was dissolved in ethanol (100 mL) and 20% palladium hydroxide on carbon (500 mg) and di-tert-butyl dicarbonate (7.8 g, 35.71 mmol) were added. The contents were stirred under a hydrogen atmosphere for 18 h. The catalyst was removed by filtration and filtrate evaporated to dryness. Purification by flash chromatography (20% tert-butyl methylether in cyclohexanone) afforded 6.16 g of (R)-3-methyl-4-oxo-3-(3-oxo-butyl)-piperidine-1-carboxylic acid tert-butyl ester as a colorless oil. LC-MS (Method A): RT=3.03 min, (M+H)⁺=284. To a solution of this material (6.10 g, 21.55 mmol) in methanol (100 mL) was added sodium methoxide (3.84 g, 43.10 mmol) and the contents heated at 50° C. for 18 hours. The volatiles were removed and the residue partitioned between EtOAc (50 mL) and water then the organic phase washed with brine and dried (MgSO₄). Purification by flash chromatography (CH₂Cl₂ 100% to 10% EtOAc in CH₂Cl₂) afforded 3.33 g of the title compound as a colorless oil. LC-MS (Method A): RT=3.15 min, (M+H)⁺ 266.

Example 27

(S)-7-[1-Hydroxy-meth-(Z)-ylidene]-8a-methyl-6-oxo-3,4,6,7,8,8a-hexahydro-1H-isoquinoline-2-carboxylic acid tert-butyl ester (37A: R⁵=4-F-Phenyl, L²-R²=CO₂-t-Butyl)

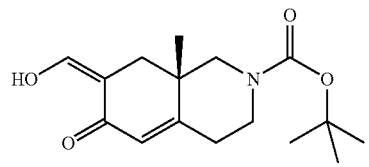

To a solution of diisopropylamine (3.05 mL, 21.79 mmol) in diethyl ether (50 mL) at −78° C. was added n-butyl lithium (12.45 mL, 1.6 M solution, 19.92 mmol). Compound (S)-36A (L²-R²=CO₂-t-butyl) (665 mg, 1.52 mmol) in diethyl ether (10 mL) was then added followed by the addition of trifluoroethyl orthoformate (6.00 g, 46.81 mmol) after 20 min. After a further 90 min, 2N HCl (30 mL) was added and the contents were warmed to ambient temperature. Water (15 mL) and EtOAc (50 mL) were added and the organic phase was separated, washed with brine and dried (MgSO₄). Removal of solvent gave 1.45 g of the title compound as a yellow powder that was used in subsequent examples without further purification. LC-MS (Method A): RT=3.56 min, (M+H)⁺ no molecular ion seen.

Example 28

(S)-1-(4-Fluoro-phenyl)-4a-methyl-1,4,4a,5,7,8-hexahydro-1,2,6-triaza-cyclopenta[b]naphthalene-6-carboxylic acid tert-butyl ester (40A: R⁵=4-F-Phenyl, L²-R²=CO₂-t-Butyl)

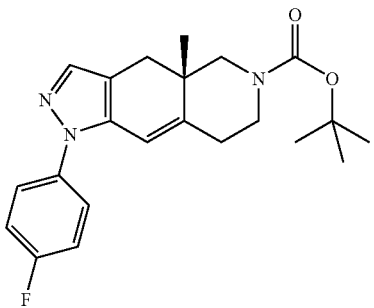

Compound 37A (L²-R²=CO₂-t-butyl) (2.50 g, 8.53 mmol) was suspended in acetic acid (25 mL) and sodium acetate (1.05 g, 12.80 mmol) and 4-fluorophenylhydrazine hydrochloride (2.08 g, 12.80 mmol) were added. After 2 h water (40 mL) was added and the organics were extracted with EtOAc (40 mL), washed with brine and dried (MgSO₄).

Purification by flash chromatography (CH$_2$Cl$_2$ 100% to 5% EtOAc in CH$_2$Cl$_2$) to afford 2.21 g of the title compound as a cream colored solid. LC-MS (Method A): RT=3.52, (M+H)$^+$= 384.

Example 29

(S)-6-(4-tert-Butyl-benzenesulfonyl)-1-(4-fluoro-phenyl)-4a-methyl-4,4a,5,6,7,8-hexahydro-1H-1,2,6-triaza-cyclopenta[b]naphthalene (40A: L2-R2=SO2(4-t-Butyl)phenyl)

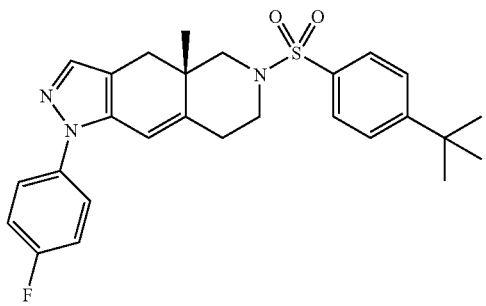

To compound 37A (L$^2$-R$^2$=CO$_2$-t-butyl) (290 mg, 0.78 mmol) was added a 20% solution of TFA in CH$_2$Cl$_2$ (3 mL) and the contents were stirred at ambient temperature for 2.5 h. The solvents were then removed. The residue was dissolved in CH$_2$Cl$_2$ (2 mL) and diisopropylethyl amine (540 μL, 3.88 mmol) and 4-tert-butylphenylsulfonyl chloride (199 mg, 0.85 mmol) were added and the contents were stirred for 18 h. Water (10 mL) was added and the organics were extracted with EtOAc (15 mL), washed with brine and dried (MgSO$_4$). Purification by flash chromatography (CH$_2$Cl$_2$ 100% to 5% EtOAc in CH$_2$Cl$_2$) afforded 600 mg of the title compound as white solid. LC-MS (Method A): RT=4.57 min, (M+H)$^+$ 480.

The following compounds were similarly prepared:

(S)-6-Benzenesulfonyl-1-(4-fluoro-phenyl)-4a-methyl-4,4a,5,6,7,8-hexahydro-1H-1,2,6-triaza-cyclo-penta[b]naphthalene

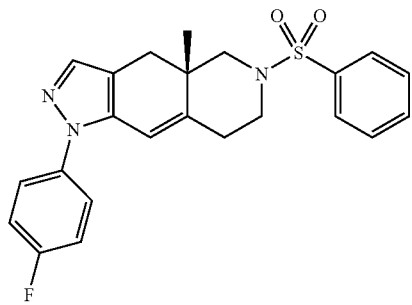

LC-MS (Method A): RT=3.93 min, (M+H)$^+$ 424.

(S)-1-(4-Fluoro-phenyl)-4a-methyl-6-(toluene-4-sulfonyl)-4,4a,5,6,7,8-hexahydro-1H-1,2,6-triaza-cyclopenta[b]naphthalene

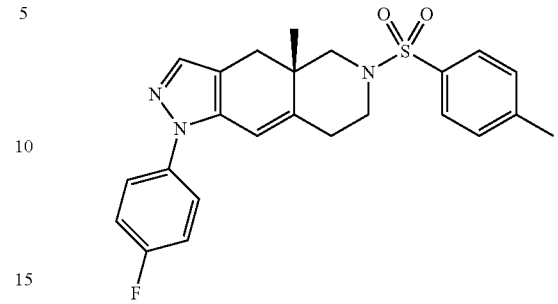

LC-MS (Method A): RT=4.11 min, (M+H)$^+$ 438.

(S)-1-(4-Trifluoromethyl-phenyl)-4a-methyl-6-(toluene-4-sulfonyl)-4,4a,5,6,7,8-hexahydro-1H-1,2,6-triaza-cyclopenta[b]naphthalene

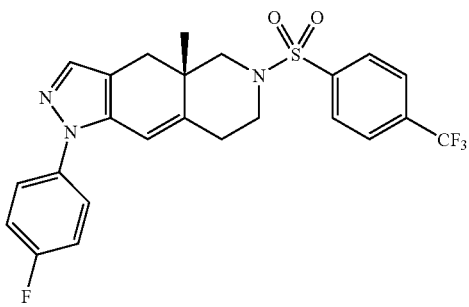

LC-MS (Method A): (M+H)$^+$ 492.

(S)-1-(4-Fluoro-phenyl)-4a-methyl-6-(4-morpholin-4-yl-benzenesulfonyl)-4,4a,5,6,7,8-hexahydro-1H-1,2,6-triaza-cyclopenta[b]naphthalene

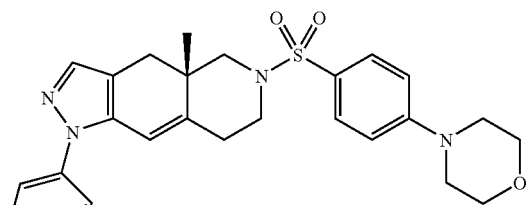

LC-MS (Method A): RT=3.81 min, (M+H)$^+$ 509.

73

(S)-1-(4-Fluoro-phenyl)-4a-methyl-6-(4-methyl-3,4-dihydro-2H-benzo[1,4]oxazine-7-sulfonyl)-4,4a,5,6,7,8-hexahydro-1H-1,2,6-triaza-cyclopenta[b]naphthalene

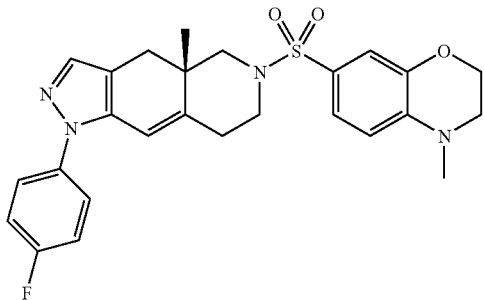

LC-MS (Method A): RT=4.01 min, (M+H)⁺ 495.

4-[(S)-1-(4-Fluoro-phenyl)-4a-methyl-1,4,4a,5,7,8-hexahydro-1,2,6-triaza-cyclopenta[b]naphthalene-6-sulfonyl]-benzonitrile

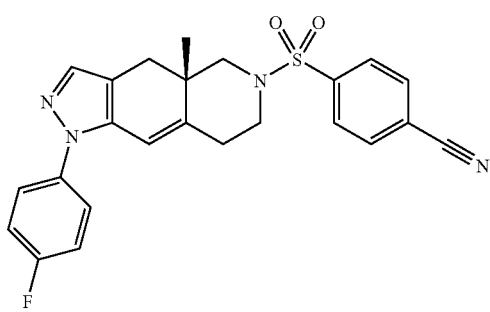

LC-MS (Method A): RT=3.85 min, (M+H)⁺ 449.

(S)-1-(4-Fluoro-phenyl)-6-(4-methoxy-benzenesulfonyl)-4a-methyl-4,4a,5,6,7,8-hexahydro-1H-1,2,6-triaza-cyclopenta[b]naphthalene

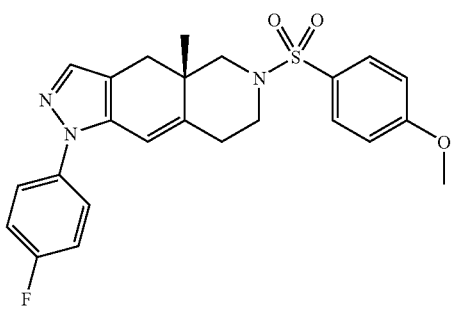

LC-MS (Method A): RT=3.86 min, (M+H)⁺ 454.

74

(S)-6-(4-Fluoro-benzenesulfonyl)-1-(4-fluoro-phenyl)-4a-methyl-4,4a,5,6,7,8-hexahydro-1H-1,2,6-triaza-cyclopenta[b]naphthalene

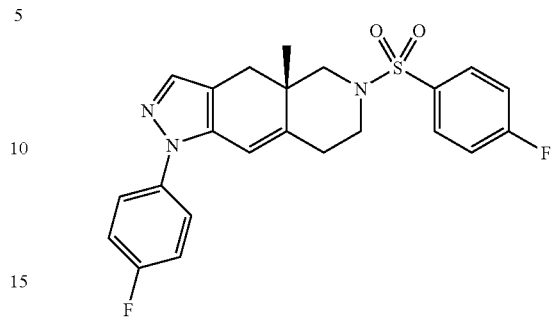

LC-MS (Method A): RT=3.90 min, (M+H)⁺ 442.

(S)-6-(2-Fluoro-benzenesulfonyl)-1-(4-fluoro-phenyl)-4a-methyl-4,4a,5,6,7,8-hexahydro-1H-1,2,6-triaza-cyclopenta[b]naphthalene

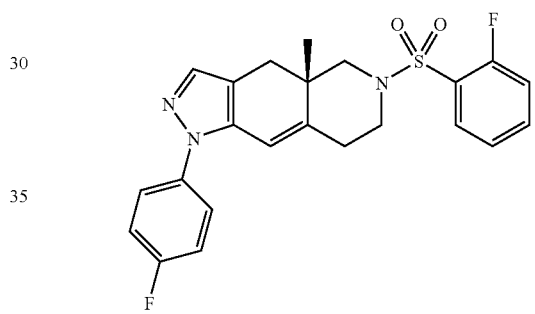

LC-MS (Method A): RT=3.87 min, (M+H)⁺ 442

(S)-1-(4-Fluoro-phenyl)-4a-methyl-6-(toluene-2-sulfonyl)-4,4a,5,6,7,8-hexahydro-1H-1,2,6-triaza-cyclopenta[b]naphthalene

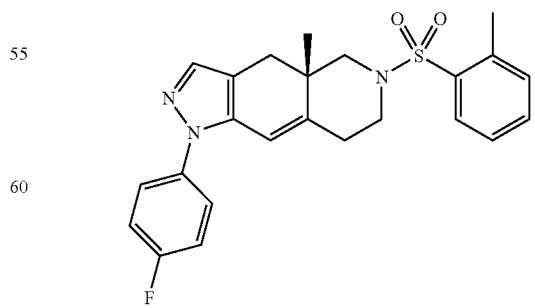

LC-MS (Method A): RT=4.02 min, (M+H)⁺ 438.

75

(S)-6-Benzyl-1-(4-fluoro-phenyl)-4a-methyl-4,4a,5,6,7,8-hexahydro-1H-1,2,6-triaza-cyclopenta[b]naphthalene

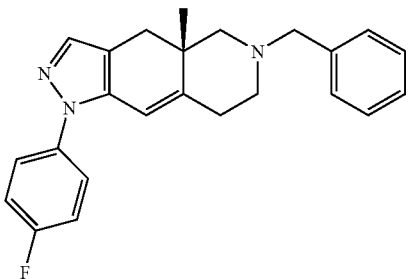

LC-MS (Method A): RT=2.34 min, (M+H)⁺ 374.

(S)-1-(4-Fluoro-phenyl)-4a-methyl-1,4,4a,5,7,8-hexahydro-1,2,6-triaza-cyclopenta[b]naphthalene-6-sulfonic acid phenylamide

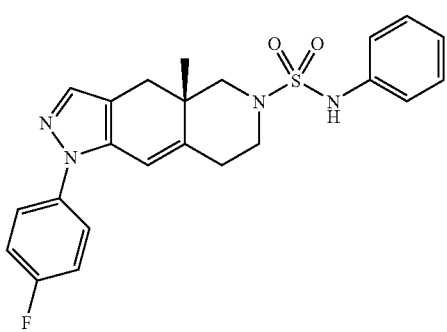

LC-MS (Method A): RT=3.82 min, (M+H)⁺ 439.

(S)-6-(4,4-Dimethyl-piperidine-1-sulfonyl)-1-(4-fluoro-phenyl)-4a-methyl-4,4a,5,6,7,8-hexahydro-1H-1,2,6-triaza-cyclopenta[b]naphthalene

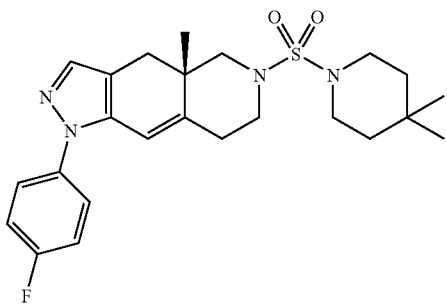

LC-MS (Method A): RT=4.38 min, (M+H)⁺ 459.

76

(S)-1-(4-Fluoro-phenyl)-4a-methyl-6-(piperidine-1-sulfonyl)-4,4a,5,6,7,8-hexahydro-1H-1,2,6-triaza-cyclopenta[b]naphthalene

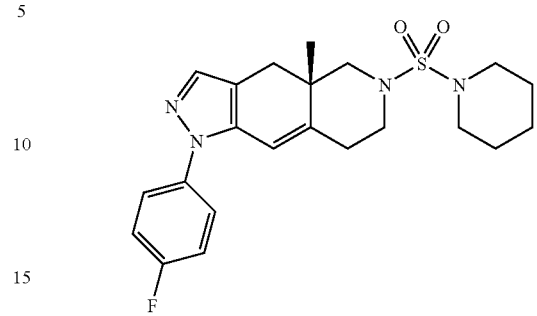

LC-MS (Method A): RT=3.85 min, (M+H)⁺ 431.

(S)-6-(4-tert-Butyl-benzenesulfonyl)-4a-methyl-1-pyridin-4-yl-4,4a,5,6,7,8-hexahydro-1H-1,2,6-triaza-cyclopenta[b]naphthalene

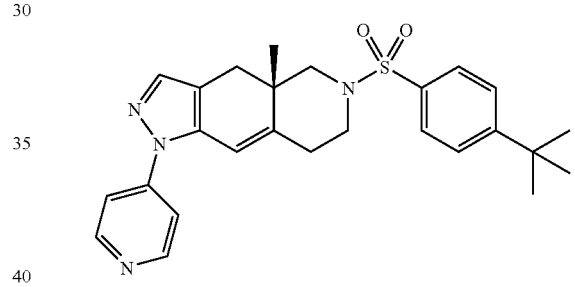

LC-MS (Method A): RT=3.11 min, (M+H)⁺ 463.

(S)-6-(4-tert-Butyl-benzenesulfonyl)-4a-methyl-1-pyridin-2-yl-4,4a,5,6,7,8-hexahydro-1H-1,2,6-triaza-cyclopenta[b]naphthalene

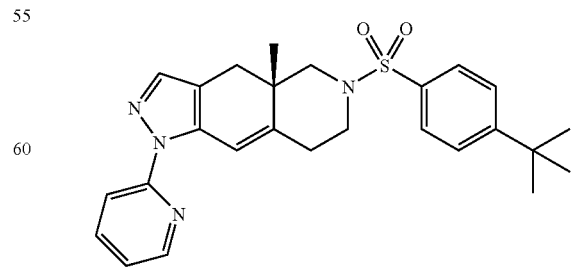

LC-MS (Method A): RT=3.10 min, (M+H)⁺ 463.

4-[(S)-1-(4-Fluoro-phenyl)-4a-methyl-1,4,4a,5,7,8-hexahydro-1,2,6-triaza-cyclopenta[b]naphthalene-6-sulfonyl]-phenylamine

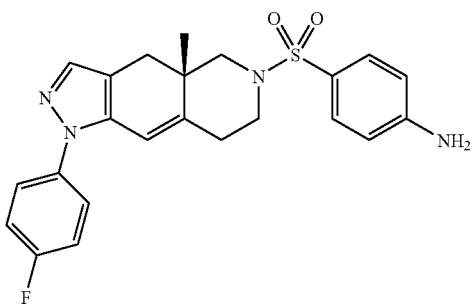

LC-MS (Method A): RT=3.53 min, (M+H)⁺ 439.

(S)-1-(4-Fluoro-phenyl)-4a-methyl-6-trimethylacetyl)-4,4a,5,6,7,8-hexahydro-1H-1,2,6-triaza-cyclopenta[b]naphthalene

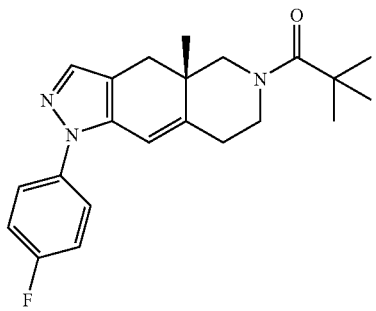

LC-MS (Method A): (M+H)⁺ 368.

Example 30

(S)-4-Oxo-3-(3-oxo-butyl)-piperidine-1,3-dicarboxylic acid 1-tert-butyl ester 3-methyl ester (46: L²-R²=CO₂-t-Butyl)

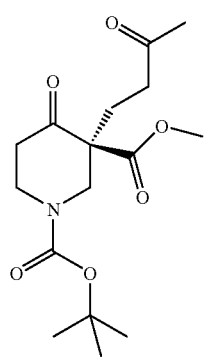

(S)-4-Oxo-3-(3-oxo-butyl)-piperidine-1,3-dicarboxylic acid 1-tert-butyl ester 3-methyl ester (35.0 g, 0.14 mol) was dissolved in toluene (150 mL) and (S)-2-amino-N,N-diethyl-3-methyl-butyramide (27.7 g, 0.16 mol) and concentrated HCl (2 mL) were added. The contents were heated to reflux for 3 h over 4 Å molecular sieves. The resultant colorless oil was dissolved in acetone (300 mL) and copper^II acetate (2.19 g, catalytic) were added and the mixture was heated at reflux for 20 min. Methylvinylketone (27.3 mL, 0.48 mmol) mmol) was added via the condenser and the contents were heated at reflux. After 2 h the mixture was cooled to ambient temperature and 2N HCl (200 mL) was added and the contents were stirred at ambient temperature for 10 min. The organics were extracted with EtOAc (100 mL), washed with water, dried with MgSO₄, concentrated and purified by flash chromatography (CH₂Cl₂ 100% to 5% acetone in CH₂Cl₂) to afford 30.58 g of the title compound as an off-white solid. LC-MS (Method A): RT=3.86 min, (M+H)⁺ 314.

Example 31

(R)-6-Oxo-4,6,7,8-tetrahydro-3H-isoquinoline-2,8a-dicarboxylic acid 2-tert-butyl ester 8a-methyl ester (47A: L²-R²=CO₂-t-Butyl)

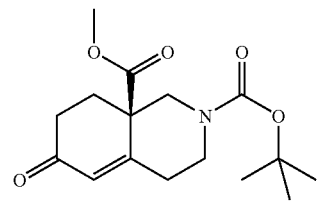

Compound 46 (L²-R²=CO₂-t-butyl) (30.0 g, 91.74 mmol) was dissolved in CH₂Cl₂ (300 mL) and pyrrolidine (6.5 mL, 77.98 mmol) and acetic acid (4.5 mL, 77.98 mmol) were added. The contents were stirred for 18 h at ambient temperature. The solvent was removed and the residue was dissolved in EtOAc, washed with water, 2M HCl, and brine, dried (MgSO₄) and concentrated in vacuo. Trituration with 50% diethyl ether in cyclohexane afforded 19.48 g of the title compound as a cream colored solid. LC-MS (Method A): RT=3.26 min, (M+H)⁺=310.

Example 32

(R)-7-[1-Hydroxymeth-(Z)-ylidene]-6-oxo-4,6,7,8-tetrahydro-3H-isoquinoline-2,8a-dicarboxylic acid 2-tert-butyl ester 8a-methyl ester (48A: L²-R²=CO₂-t-Butyl)

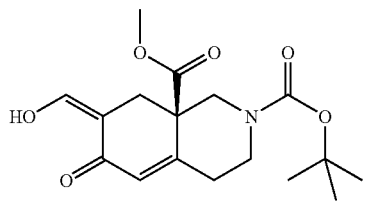

To a solution of diisopropylamine (0.79 mL, 5.66 mmol) in diethyl ether (20 mL) at −78° C. was added n-butyl lithium (3.20 mL, 1.6 M solution, 5.17 mmol). Compound 47A (L²-R²=CO₂-t-butyl) (1.0 g, 3.23 mmol) in diethyl ether (5 mL) was added followed by the addition of trifluoroethyl orthoformate (1.20 mL, 12.92 mmol) after 20 min. After a further 90 min, 2N HCl (10 mL) was added and the contents were allowed to warm to ambient temperature. Water (10 mL) and EtOAc (20 mL) were added and the organic phase was separated, washed with brine and dried (MgSO₄). Removal of solvent gave 0.77 g of the title compound as a yellow powder, which was used in subsequent examples without further purification. LC-MS (Method A): RT=3.65 min, (M+H)+ 338.

Example 33

(R)-1-(4-Fluoro-phenyl)-1,4,7,8-tetrahydro-1,2,6-triaza-cyclopenta[b]naphthalene-4a,6-dicarboxylic acid 6-tert-butyl ester 4a-methyl ester (49A: $R^5$=4-F-Ph; $L^2$-$R^2$=$CO_2$-t-Butyl)

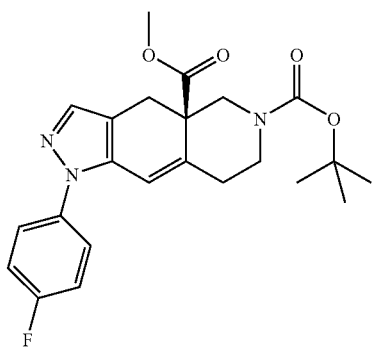

Compound 48A ($L^2$-$R^2$=$CO_2$-t-butyl) (7.90 g, 23.44 mmol) was suspended in acetic acid (75 mL) and sodium acetate (2.90 g, 35.16 mmol) and 4-fluorophenylhydrazine hydrochloride (5.70 g, 35.16 mmol) were added. After 1 h water (60 mL) was added and the organics were extracted with EtOAc (60 mL) and washed with brine and dried ($MgSO_4$). Purification by flash chromatography ($CH_2Cl_2$ 100% to 5% acetone in $CH_2Cl_2$) to afford 3.05 g of the title compound as a cream colored solid. LC-MS (Method A): RT=3.72 min, (M+H)+=428.

Example 34

(R)-6-(4-tert-Butyl-benzenesulfonyl)-1-(4-fluoro-phenyl)-1,4,5,6,7,8-hexahydro-1,2,6-triaza-cyclo-penta[b]naphthalene-4a-carboxylic acid methyl ester (49A: $R^5$=4-F-Ph; $L^2$-$R^2$=$SO_2$(4-t-Butyl)phenyl)

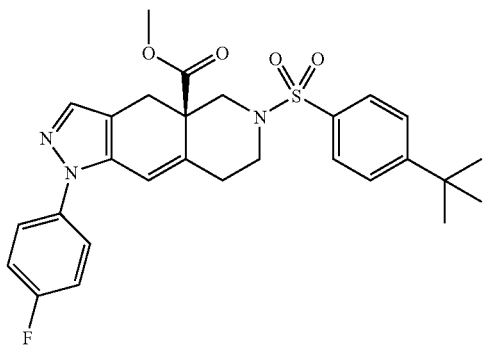

To compound 48A ($R^5$=4-F-Ph; $L^2$-$R^2$=$CO_2$-t-Butyl) (2.0 g, 4.68 mmol) was added a 20% solution of TFA in $CH_2Cl_2$ (15 mL) and the contents were stirred at ambient temperature for 1. The solvents were then removed in vacuo. The residue was dissolved in $CH_2Cl_2$ (2 mL) and diisopropylethyl amine (3.38 mL, 7.03 mmol) and 4-t-butylphenylsulfonyl chloride (2.26 mg, 7.03 mmol) were added and the contents were stirred for 2 h. Water (50 mL) was added and the organics were extracted with EtOAc (50 mL) and washed with brine and dried ($MgSO_4$). Purification by flash chromatography ($CH_2Cl_2$ 100% to 5% EtOAc in $CH_2Cl_2$) afforded 2.05 g of the title compound as white solid. LC-MS (Method A): RT=4.34 min, (M+H)+ 524.

The following compounds were similarly prepared:

(R)-1-Butyl-6-(4-tert-butyl-benzenesulfonyl)-1,4,5,6,7,8-hexahydro-1,2,6-triaza-cyclopenta[b]naphtha-lene-4a-carboxylic acid methyl ester

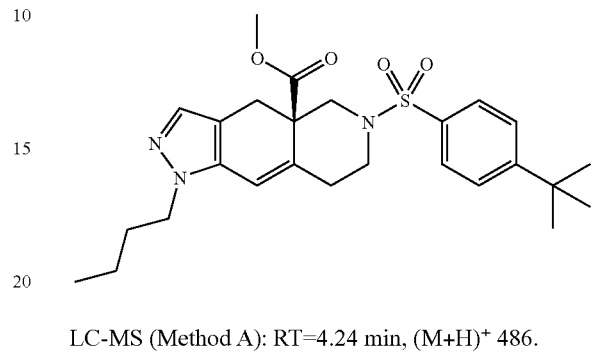

LC-MS (Method A): RT=4.24 min, (M+H)+ 486.

(R)-6-(4-tert-Butyl-benzenesulfonyl)-1-isopropyl-1,4,5,6,7,8-hexahydro-1,2,6-triaza-cyclopenta[b]naph-thalene-4a-carboxylic acid methyl ester

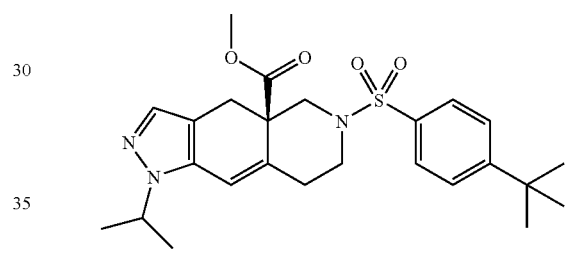

LC-MS (Method A): RT=3.88 min, (M+H)+ 472.

Example 35

[(R)-6-(4-tert-Butyl-benzenesulfonyl)-1-(4-fluoro-phenyl)-1,4,5,6,7,8-hexahydro-1,2,6-triaza-cyclo-penta[b]naphthalen-4a-yl]-methanol (50A: $R^5$=4-F-Ph; $L^2$-$R^2$=$SO_2$(4-t-Butyl)phenyl)

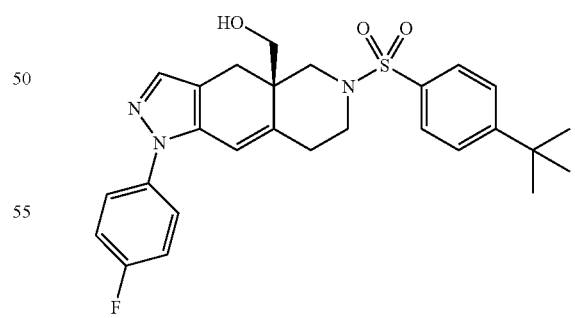

To compound 49A ($R^5$=4-F-Ph; $L^2$-$R^2$=$SO_2$(4-t-butyl)phenyl) (100 mg, 0.19 mmol) in $CH_2Cl_2$ (2 mL) was added DIBAL-H (420 μL, 1.0 M solution, 0.42 mmol) at −78° C. and the contents were stirred for 1 h. The reaction was quenched by the addition of water (1 mL). The organics were extracted with $CH_2Cl_2$ (10 mL), washed with brine and dried ($MgSO_4$). Purification by flash chromatography ($CH_2Cl_2$ 100% to 5%

EtOAc in CH$_2$Cl$_2$) afforded 31 mg of the title compound as white solid. LC-MS (Method A): RT=4.16 min, (M+H)$^+$ 496.

The following compounds were similarly prepared:

[(R)-6-(4-Fluoro-benzenesulfonyl)-1-(4-fluoro-phenyl)-1,4,5,6,7,8-hexahydro-1,2,6-triaza-cyclopenta[b]naphthalen-4a-yl]-methanol

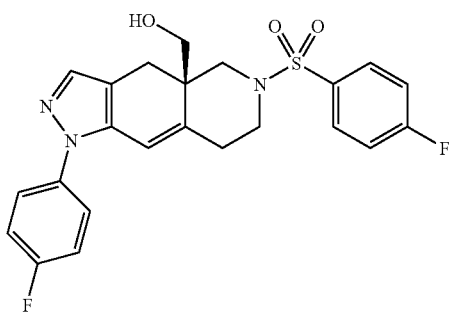

LC-MS (Method A): RT=3.57 min, (M+H)$^+$ 458.

[(R)-1-(4-Fluoro-phenyl)-6-(toluene-4-sulfonyl)-1,4,5,6,7,8-hexahydro-1,2,6-triaza-cyclopenta[b]naphthalen-4a-yl]-methanol

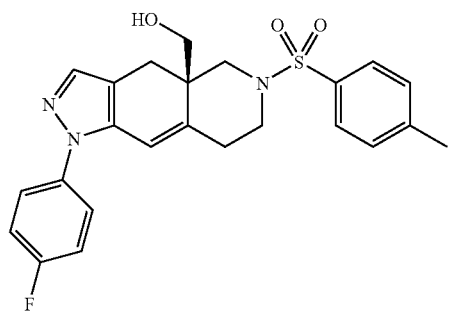

LC-MS (Method A): RT=3.68 min, (M+H)$^+$ 454.

[(R)-6-Benzenesulfonyl-1-(4-fluoro-phenyl)-1,4,5,6,7,8-hexahydro-1,2,6-triaza-cyclopenta[b]naphthalen-4a-yl]-methanol

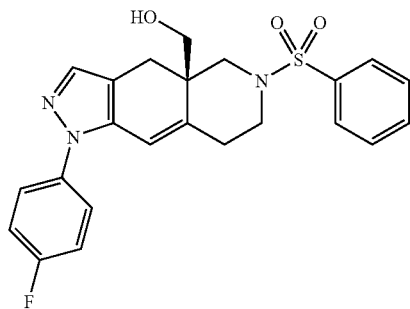

LC-MS (Method B): RT=10.89 min, (M+H)$^+$ 440.

Example 36

(R)-6-(4-tert-Butyl-benzenesulfonyl)-1-(4-fluorophenyl)-4a-methoxymethyl-4,4a,5,6,7,8-hexahydro-1H-1,2,6-triaza-cyclopenta[b]naphthalene (51A: R$^5$=4-F-Ph; R$^{14}$=Me; L$^2$-R$^2$=SO$_2$(4-t-Butylphenyl)

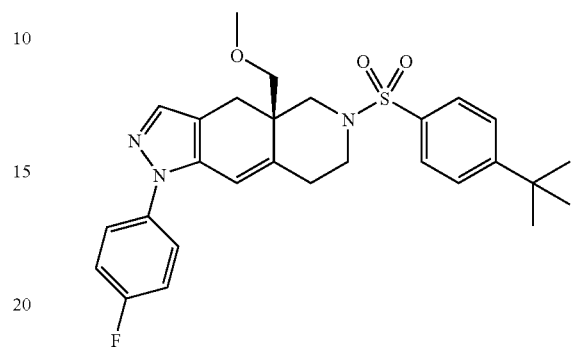

To compound 49A (R$^5$=4-F-Ph; L$^2$-R$^2$=SO$_2$(4-t-butylphenyl) (100 mg, 0.20 mmol) in THF (1 mL) was added sodium hydride (24 mg, 0.60 mmol) and iodomethane (37 μL, 0.60 mmol) and the mixture was stirred at 75° C. for 18 h. The cooled contents were partitioned between EtOAc (10 mL) and water (10 mL) and washed with brine and dried (MgSO$_4$). Purification by flash chromatography (CH$_2$Cl$_2$ 100% to 5% EtOAc in CH$_2$Cl$_2$) afforded 38 mg of the title compound as white solid. LC-MS (Method A): RT=4.51 min, (M+H)$^+$ 510.

The following compounds were similarly prepared:

(R)-6-(4-tert-Butyl-benzenesulfonyl)-1-(4-fluorophenyl)-4a-(2-methoxy-ethoxymethyl)-4,4a,5,6,7,8-hexahydro-1H-1,2,6-triaza-cyclopenta[b]naphthalene

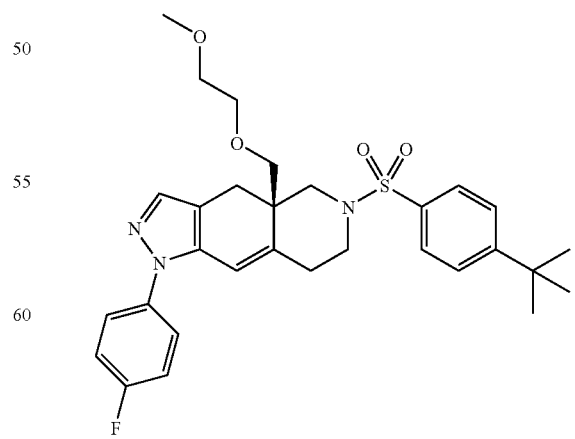

LC-MS (Method A) RT=4.68 min, (M+H)$^+$ 534.

83

(R)-6-(Benzenesulfonyl)-1-(4-fluoro-phenyl)-4a-(2-hydroxy-ethoxymethyl)-4,4a,5,6,7,8-hexahydro-1H-1,2,6-triaza-cyclopenta[b]naphthalene

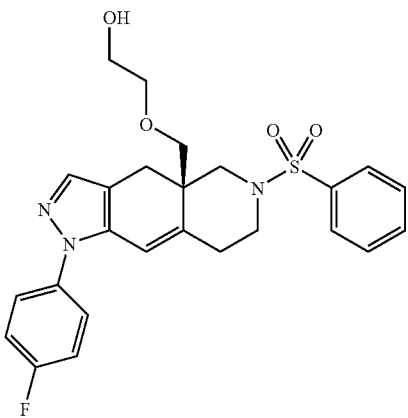

LC-MS (Method A) (M+H)⁺ 484.

(R)-6-(4-tert-Butyl-benzenesulfonyl)-4a-ethoxymethyl-1-(4-fluoro-phenyl)-4,4a,5,6,7,8-hexahydro-1H-1,2,6-triaza-cyclopenta[b]naphthalene

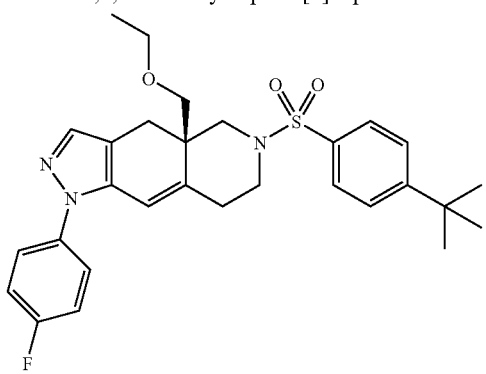

LC-MS (Method A): RT=4.57 min, (M+H)⁺ 524.

(R)-6-(4-tert-Butyl-benzenesulfonyl)-1-(4-fluoro-phenyl)-4a-(3-methoxy-propoxymethyl)-4,4a,5,6,7,8-hexahydro-1H-1,2,6-triaza-cyclopenta[b]naphthalene

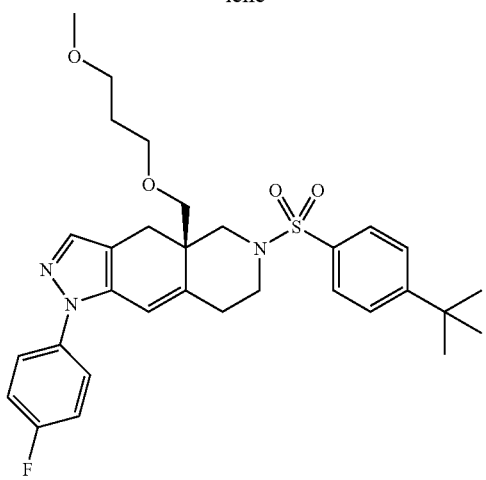

LC-MS (Method A): RT=4.69 min, (M+H)⁺ 568.

84

3-[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethoxy]-propionitrile

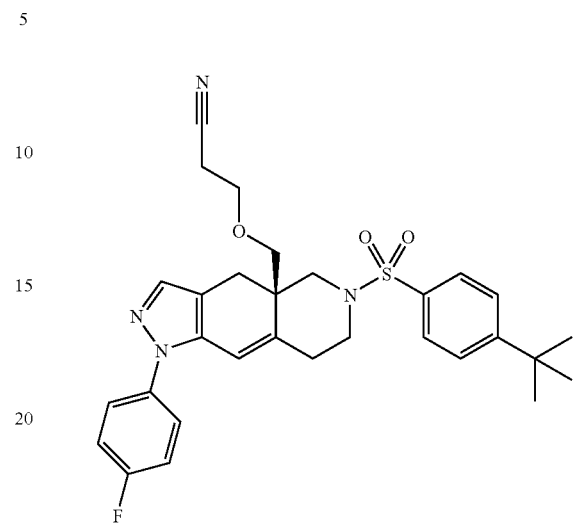

LC-MS (Method A): RT=4.38 min, (M+H)⁺ 549.

(R)-6-(4-tert-Butyl-benzenesulfonyl)-1-(4-fluoro-phenyl)-4a-(2-morpholin-4-yl-ethoxymethyl)-4,4a,5,6,7,8-hexahydro-1H-1,2,6-triaza-cyclopenta[b]naphthalene

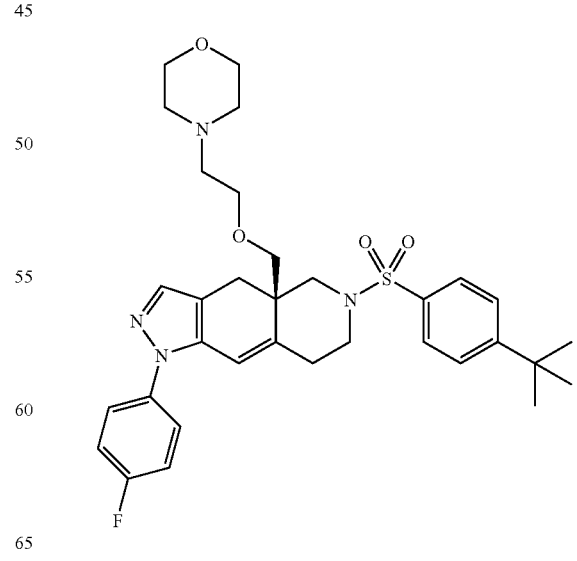

LC-MS (Method A): RT=2.90 min, (M+H)⁺ 609.

85

(R)-6-(4-tert-Butyl-benzenesulfonyl)-1-(4-fluoro-phenyl)-4a-(2-piperidin-1-yl-ethoxymethyl)-4,4a,5,6,7,8-hexahydro-1H-1,2,6-triaza-cyclopenta[b]naphthalene

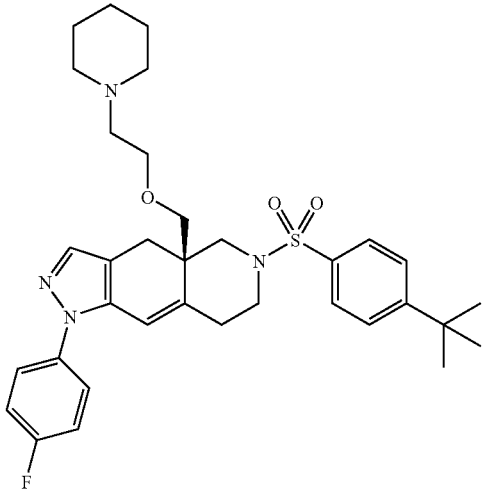

LC-MS (Method A): RT=2.94 min, (M+H)+ 607.

(R)-6-(4-tert-Butyl-benzenesulfonyl)-1-(4-fluoro-phenyl)-4a-(2-pyrrolidin-1-yl-ethoxymethyl)-4,4a,5,6,7,8-hexahydro-1H-1,2,6-triaza-cyclopenta[b]naphthalene

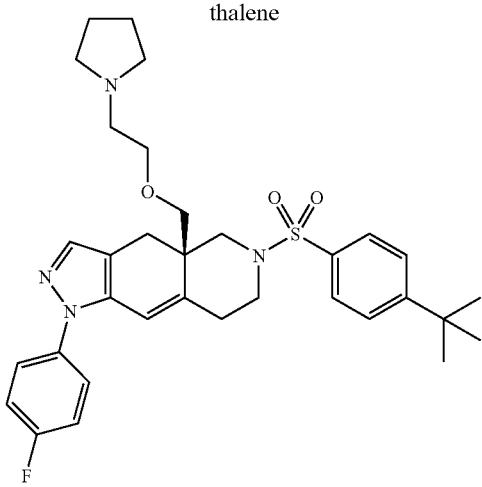

LC-MS (Method A): RT=2.92 min, (M+H)+ 593.

(R)-6-(4-Fluoro-benzenesulfonyl)-1-(4-fluoro-phenyl)-4a-(2-methoxy-ethoxymethyl)-4,4a,5,6,7,8-hexahydro-1H-1,2,6-triaza-cyclopenta[b]naphthalene

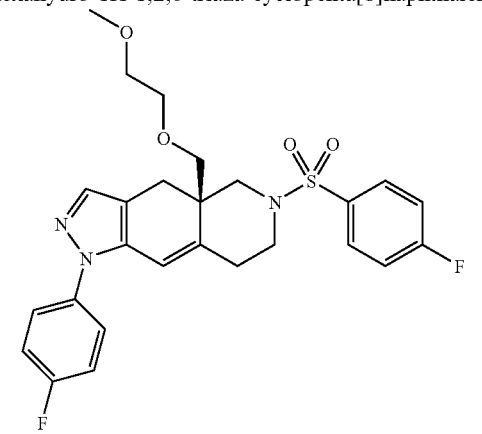

LC-MS (Method B): RT=12.26 min, (M+H)+ 516.

86

(R)-6-(4-Fluoro-benzenesulfonyl)-1-(4-fluoro-phenyl)-4a-methoxymethyl-4,4a,5,6,7,8-hexahydro-1H-1,2,6-triaza-cyclopenta[b]naphthalene

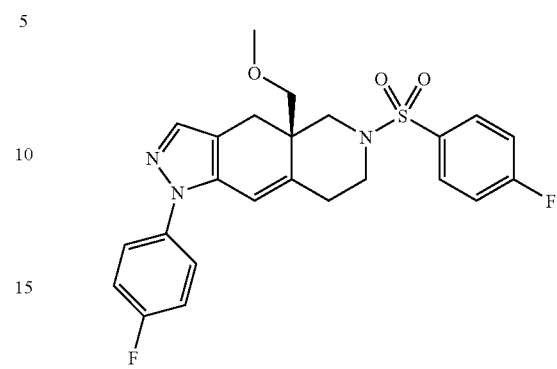

LC-MS (Method B): RT=12.47 min, (M+H)+ 472.

(R)-1-(4-Fluoro-phenyl)-4a-methoxymethyl-6-(toluene-4-sulfonyl)-4,4a,5,6,7,8-hexahydro-1H-1,2,6-triaza-cyclopenta[b]naphthalene

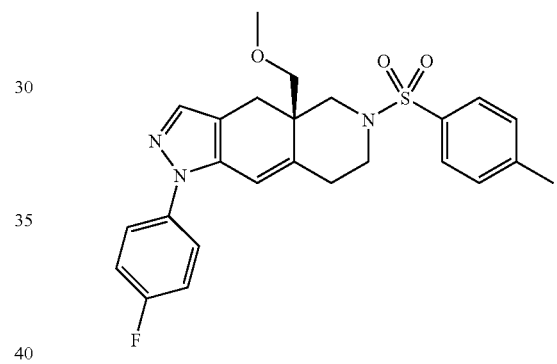

LC-MS (Method B): RT=12.81 min, (M+H)+ 468.

(R)-1-(4-Fluoro-phenyl)-4a-(2-methoxy-ethoxymethyl)-6-(toluene-4-sulfonyl)-4,4a,5,6,7,8-hexahydro-1H-1,2,6-triaza-cyclopenta[b]naphthalene

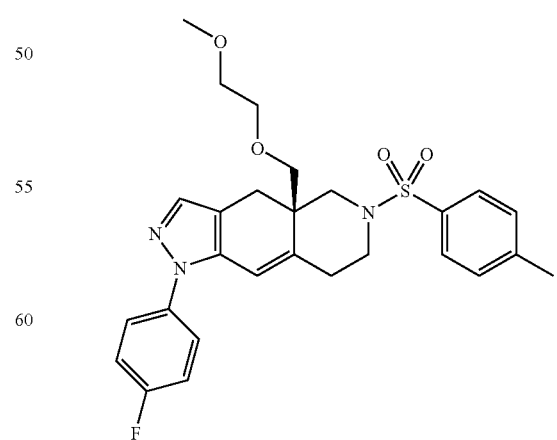

LC-MS (Method B): RT=12.67 min, (M+H)+ 512.

87

(R)-6-Benzenesulfonyl-1-(4-fluoro-phenyl)-4a-(2-methoxy-ethoxymethyl)-4,4a,5,6,7,8-hexahydro-1H-1,2,6-triaza-cyclopenta[b]naphthalene

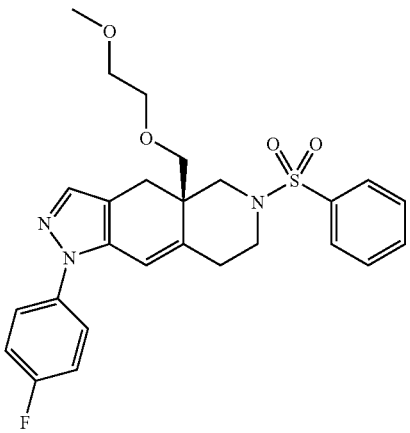

LC-MS (Method A): RT=3.88 min, (M+H)⁺ 498.

(R)-6-Benzenesulfonyl-1-(4-fluoro-phenyl)-4a-methoxymethyl-4,4a,5,6,7,8-hexahydro-1H-1,2,6-triaza-cyclopenta[b]naphthalene

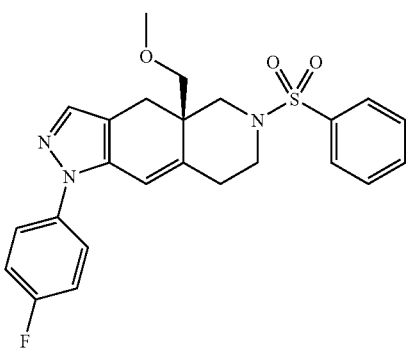

LC-MS (Method A): RT=3.93 min, (M+H)⁺ 454.

(R)-1-(4-Fluoro-phenyl)-4a-(2-methoxy-ethoxymethyl)-1,4,4a,5,7,8-hexahydro-1,2,6-triaza-cyclopenta[b]naphthalene-6-sulfonic acid dimethylamide

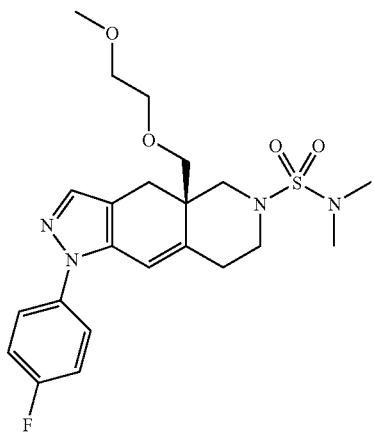

LC-MS (Method A): RT=3.58 min, (M+H)⁺ 465.

88

(R)-1-(4-Fluoro-phenyl)-4a-methoxymethyl-1,4,4a,5,7,8-hexahydro-1,2,6-triaza-cyclopenta[b]naphthalene-6-sulfonic acid dimethylamide

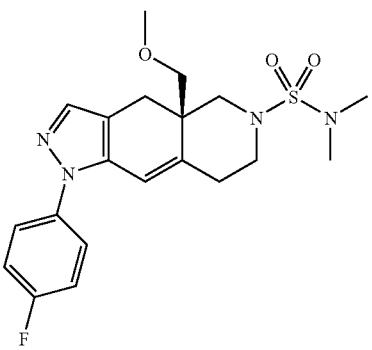

LC-MS (Method A): RT=3.62 min, (M+H)⁺ 421.

(R)-6-(Butane-1-sulfonyl)-1-(4-fluoro-phenyl)-4a-(2-methoxy-ethoxymethyl)-4,4a,5,6,7,8-hexahydro-1H-1,2,6-triaza-cyclopenta[b]naphthalene

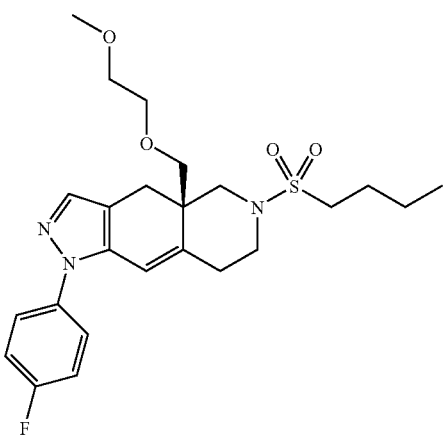

LC-MS (Method A): RT=3.05 min, (M+H)⁺ 478.

(R)-(4-tert-butyl-benzenesulfonyl)-4a-(2-methoxy-ethoxymethyl)-1-methyl-4,4a,5,6,7,8-hexahydro-1H-1,2,6-triaza-cyclopenta[b]naphthalene

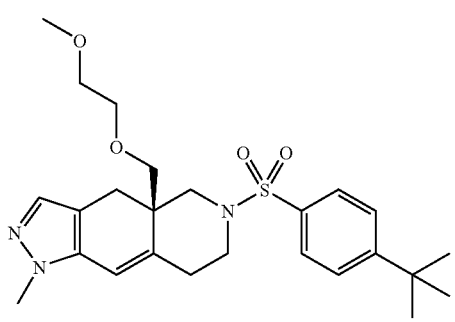

LC-MS (Method A): RT=3.87 min, (M+H)⁺ 474.

89

(R)-1-Butyl-6-(4-tert-butyl-benzenesulfonyl)-4a-(2-methoxy-ethoxymethyl)-4,4a,5,6,7,8-hexahydro-1H-1,2,6-triaza-cyclopenta[b]naphthalene

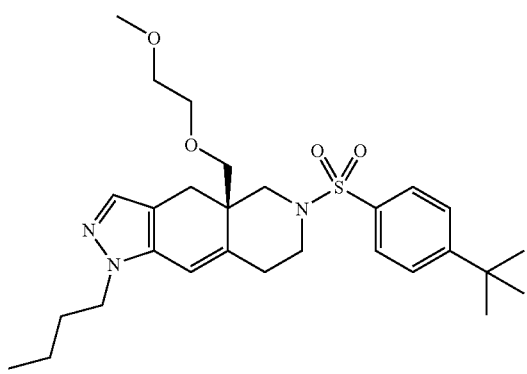

LC-MS (Method A): RT=4.36 min, (M+H)+ 516.

(R)-6-(4-tert-Butyl-benzenesulfonyl)-1-isopropyl-4a-(2-methoxy-ethoxymethyl)-4,4a,5,6,7,8-hexahydro-1H-1,2,6-triaza-cyclopenta[b]naphthalene

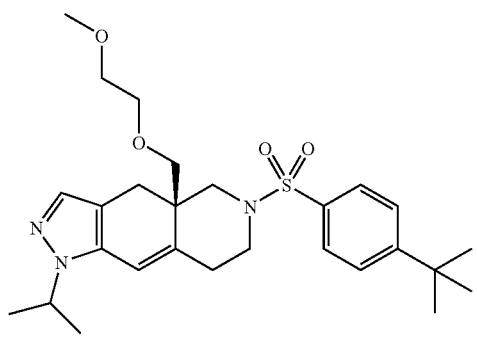

LC-MS (Method A): RT=4.03 min, (M+H)+ 502.

(R)-6-(4-tert-Butyl-benzenesulfonyl)-1-isopropyl-4a-methoxymethyl-4,4a,5,6,7,8-hexahydro-1H-1,2,6-triaza-cyclopenta[b]naphthalene

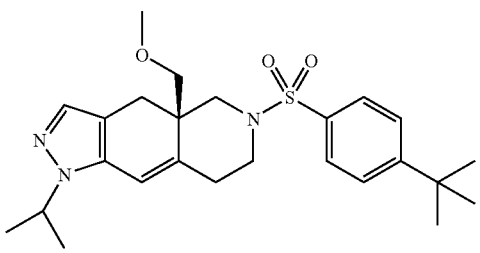

LC-MS (Method A): RT=4.07 min, (M+H)+ 458.

90

(R)-1-Butyl-4a-methoxymethyl-6-(toluene-4-sulfonyl)-4,4a,5,6,7,8-hexahydro-1H-1,2,6-triaza-cyclopenta[b]naphthalene

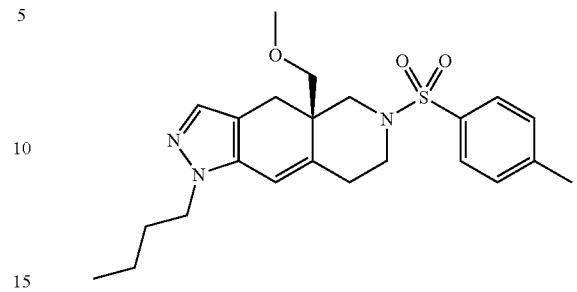

LC-MS (Method A): RT=3.78 min, (M+H)+ 430.

(R)-1-Butyl-4a-(2-methoxy-ethoxymethyl)-6-(toluene-4-sulfonyl)-4,4a,5,6,7,8-hexahydro-1H-1,2,6-triaza-cyclopenta[b]naphthalene

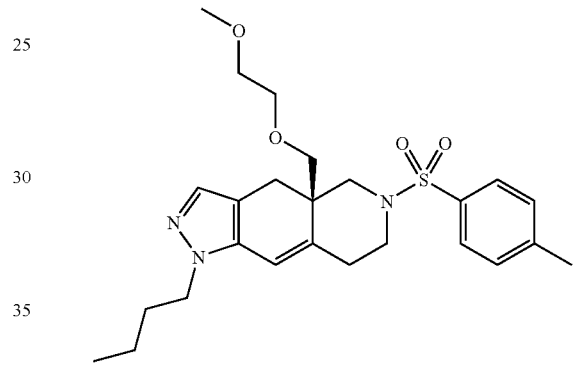

LC-MS (Method A): RT=3.74 min, (M+H)+ 474.

Example 37

(R)-6-(4-tert-Butyl-benzenesulfonyl)-1-(4-fluorophenyl)-1,4,5,6,7,8-hexahydro-1,2,6-triaza-cyclopenta[b]naphthalene-4a-carbaldehyde (52A: R$^5$=4-F-Ph; L$^2$-R$^2$=SO$_2$(4-t-Butylphenyl)

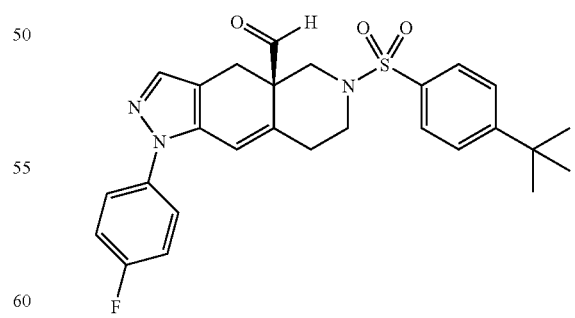

Oxalyl chloride (0.23 mL, 2.57 mmol) in CH$_2$Cl$_2$ (10 mL) was cooled to −78° C. and DMSO (0.4 mL, 5.62 mmol) in CH$_2$Cl$_2$ (4 mL) was added. After 5 min, compound 49A (R$^5$=4-F-Ph; L$^2$-R$^2$=SO$_2$(4-t-butylphenyl) (0.58 g, 1.17 mmol) was added and the contents were stirred for 20 min.

Triethylamine (0.81 mL, 5.85 mmol) was added and the contents were warmed to ambient temperature. The organics were partitioned between EtOAc (10 mL) and water (10 mL), washed with brine and dried (MgSO$_4$). Purification by flash chromatography (CH$_2$Cl$_2$ 100% to 5% EtOAc in CH$_2$Cl$_2$) afforded 42 mg of the title compound as white solid. LC-MS (Method A): RT=4.1 3 min, (M+H)$^+$ 494.

Example 38

[(S)-6-(4-tert-Butyl-benzenesulfonyl)-1-(4-fluoro-phenyl)-1,4,5,6,7,8-hexahydro-1,2,6-triaza-cyclo-penta[b]naphthalen-4a-ylmethyl]-dimethyl-amine (53A: R$^5$=4-F-Ph; L$^2$-R$^2$=SO$_2$(4-t-butylphenyl), R$^{1C}$=R$^{1D}$=Methyl)

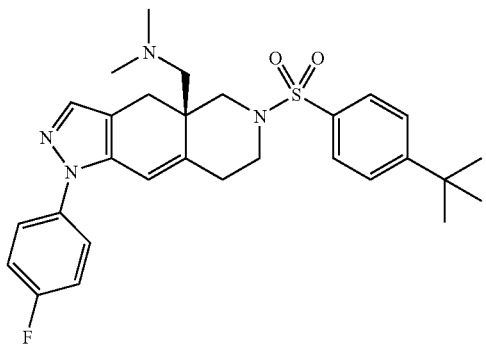

To a solution of compound 52A (R$^5$=4-F-Ph; L$^2$-R$^2$=SO$_2$(4-t-butylphenyl) (50 mg, 0.10 mmol) in dichloroethane (1 mL) was added dimethylamine (0.1 mL, 0.20 mmol) and sodium triacetoxyborohydride (30 mg, 0.14 mmol). The contents were stirred for 18 h at ambient temperature, NaHCO$_3$ (2 mL) was added, and the organics were extracted with CH$_2$Cl$_2$ (10 mL), washed with brine and dried (MgSO$_4$). Purification by flash chromatography (Amino-SPE: CH$_2$Cl$_2$ 100% to 5% EtOAc in CH$_2$Cl$_2$) afforded 61 mg of the title compound as an off white solid. LC-MS (Method A): RT=2.79 min, (M+H)$^+$ 523.

The following compounds were similarly prepared:

(S)-6-(4-tert-Butyl-benzenesulfonyl)-1-(4-fluoro-phenyl)-4a-morpholin-4-ylmethyl-4,4a,5,6,7,8-hexahydro-1H-1,2,6-triaza-cyclopenta[b]naphthalene

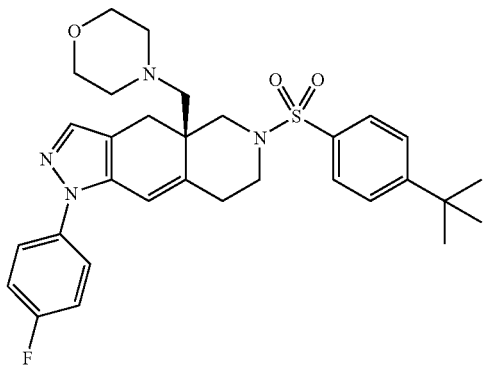

LC-MS (Method A): RT=3.73 min, (M+H)$^+$ 565.

(S)-6-(4-Trifluoromethyl-benzenesulfonyl)-1-(4-fluoro-phenyl)-4a-morpholin-4-ylmethyl-4,4a,5,6,7,8-hexahydro-1H-1,2,6-triaza-cyclopenta[b]naphthalene

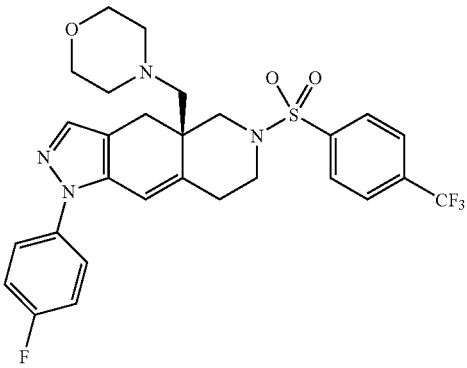

LC-MS (Method A): (M+H)$^+$ 577.

(S)-6-(1-Cyclopropylmethylsulfonyl)-1-(4-fluoro-phenyl)-4a-morpholin-4-ylmethyl-4,4a,5,6,7,8-hexahydro-1H-1,2,6-triaza-cyclopenta[b]naphthalene

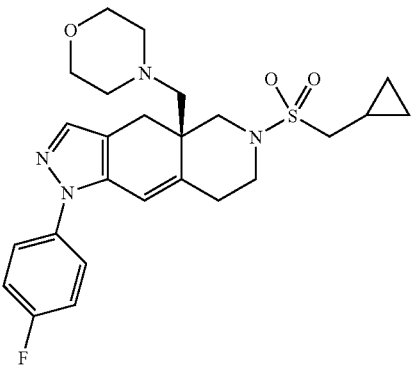

LC-MS (M+H)$^+$ 485.

(S)-6-(4-tert-Butyl-benzenesulfonyl)-1-(4-fluoro-phenyl)-4a-pyrrolidin-1-ylmethyl-4,4a,5,6,7,8-hexahydro-1H-1,2,6-triaza-cyclopenta[b]naphthalene

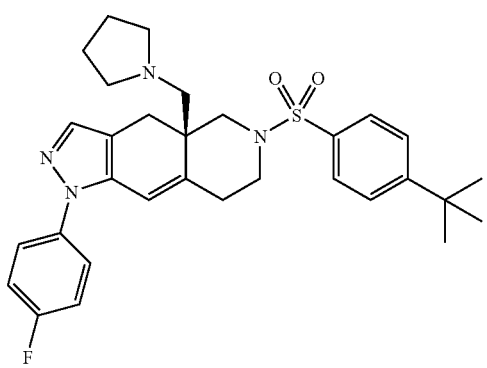

LC-MS (Method A): RT=2.91 min, (M+H)$^+$ 549.

93

([(S)-6-(4-tert-Butyl-benzenesulfonyl)-1-(4-fluoro-phenyl)-1,4,5,6,7,8-hexahydro-1,2,6-triaza-cyclo-penta[b]naphthalen-4a-ylmethyl]-ethyl-amine

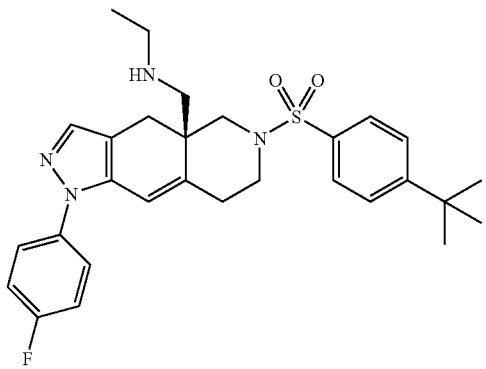

LC-MS (Method A): RT=2.82 min, (M+H)$^+$ 523.

[(S)-6-(4-tert-Butyl-benzenesulfonyl)-1-(4-fluoro-phenyl)-1,4,5,6,7,8-hexahydro-1,2,6-triaza-cyclo-penta[bnaphthalen-4a-ylmethyl]-diethyl-amine

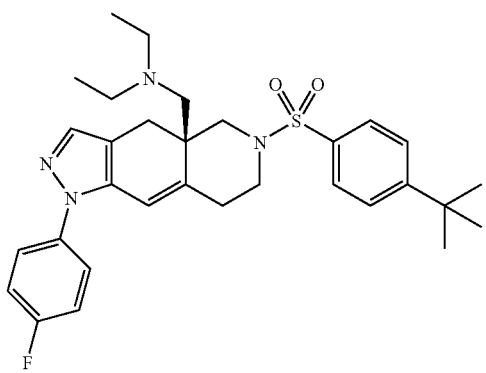

LC-MS (Method A): RT=2.92 min, (M+H)$^+$ 551.

(S)-6-(4-tert-Butyl-benzenesulfonyl)-1-(4-fluoro-phenyl)-4a-piperidin-1-ylmethyl-4,4a,5,6,7,8-hexahydro-1H-1,2,6-triaza-cyclopenta[b]naphthalene

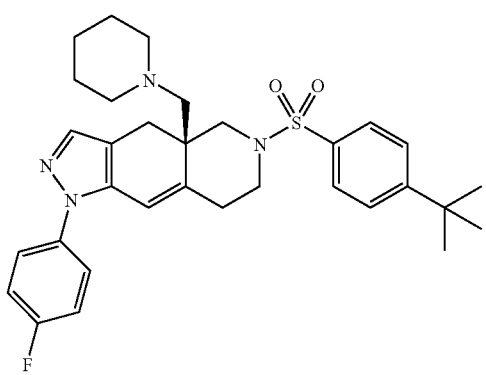

LC-MS (Method A): RT=2.99 min, (M+H)$^+$ 563.

94

[(S)-6-(4-tert-Butyl-benzenesulfonyl)-1-(4-fluoro-phenyl)-1,4,5,6,7,8-hexahydro-1,2,6-triaza-cyclo-penta[b]naphthalen-4a-ylmethyl]-(2-methoxy-ethyl)-amine

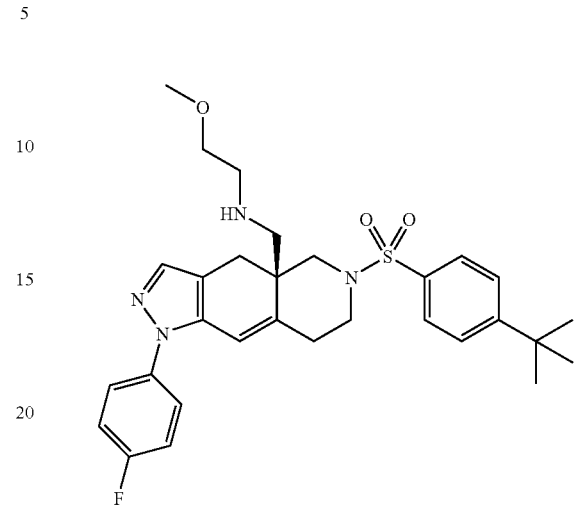

LC-MS (Method A): RT=2.74 min, (M+H)$^+$ 553.

(S)-6-(4-tert-Butyl-benzenesulfonyl)-1-(4-fluoro-phenyl)-4a-(4-methyl-piperazin-1-ylmethyl)-4,4a,5,6,7,8-hexahydro-1H-1,2,6-triaza-cyclopenta[b]naphthalene

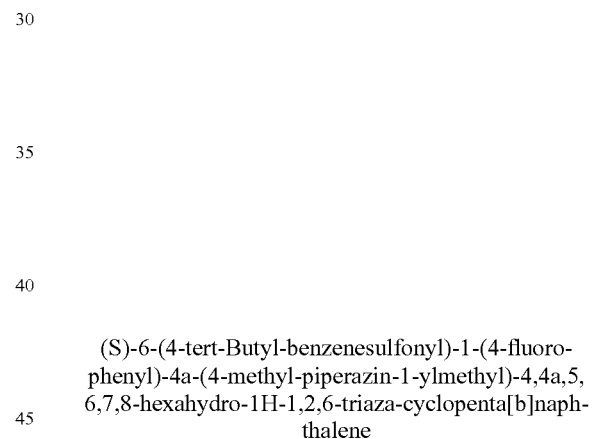

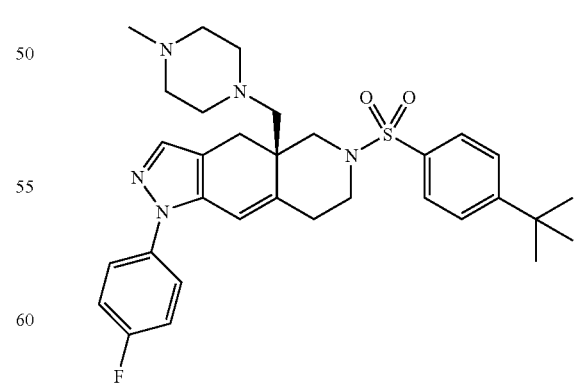

LC-MS (Method A): RT=2.83 min, (M+H)$^+$ 578.

95

N'-[(S)-6-(4-tert-Butyl-benzenesulfonyl)-1-(4-fluoro-phenyl)-1,4,5,6,7,8-hexahydro-1,2,6-triaza-cyclo-penta[b]naphthalen-4a-ylmethyl]-N,N-dimethyl-ethane-1,2-diamine

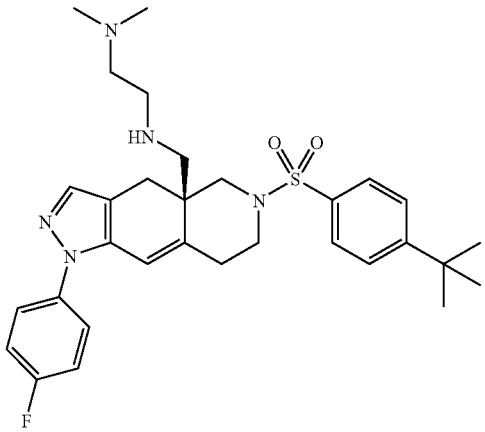

LC-MS (Method A): RT=2.63 min, (M+H)$^+$ 566.

96

N'-[(S)-6-(4-tert-Butyl-benzenesulfonyl)-1-(4-fluoro-phenyl)-1,4,5,6,7,8-hexahydro-1,2,6-triaza-cyclo-penta[b]naphthalen-4a-ylmethyl]-N,N-dimethyl-propane-1,3-diamine

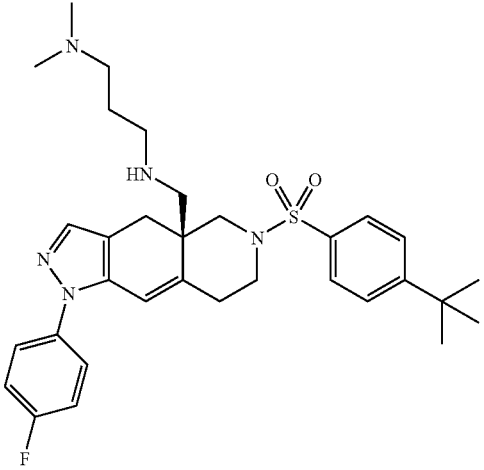

LC-MS (Method A): RT=2.20 min, (M+H)$^+$ 580.

N-[(S)-6-(4-tert-Butyl-benzenesulfonyl)-1-(4-fluoro-phenyl)-1,4,5,6,7,8-hexahydro-1,2,6-triaza-cyclo-penta[b]naphthalen-4a-ylmethyl]-N,N',N'-trimethyl-ethane-1,2-diamine

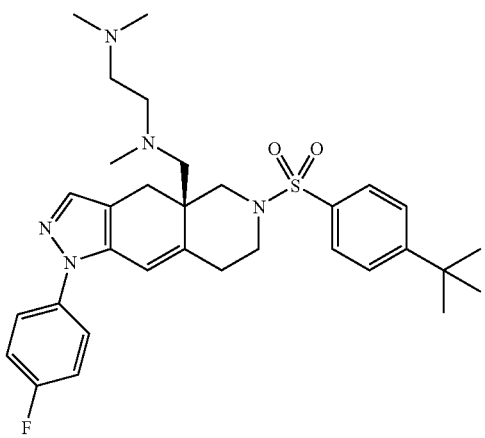

LC-MS (Method A): RT=2.96 min, (M+H)$^+$ 580.

N-[(S)-6-(4-tert-Butyl-benzenesulfonyl)-1-(4-fluoro-phenyl)-1,4,5,6,7,8-hexahydro-1,2,6-triaza-cyclo-penta[b]naphthalen-4a-ylmethyl]-N,N',N'-trimethyl-propane-1,3-diamine

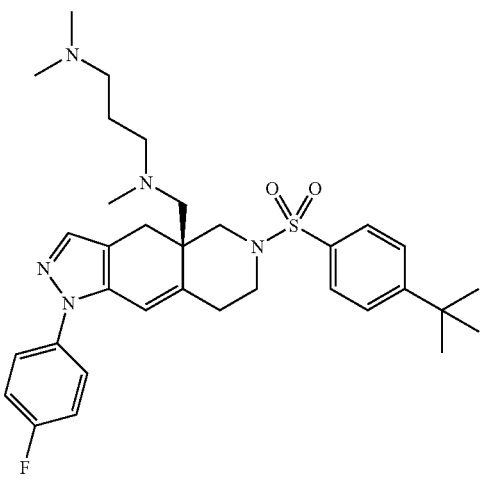

LC-MS (Method A): RT=2.29 min, (M+H)$^+$ 594.

97

[(S)-6-(4-tert-Butyl-benzenesulfonyl)-1-(4-fluoro-phenyl)-1,4,5,6,7,8-hexahydro-1,2,6-triaza-cyclo-penta[b]naphthalen-4a-ylmethyl]-(2-methoxy-ethyl)-methyl-amine

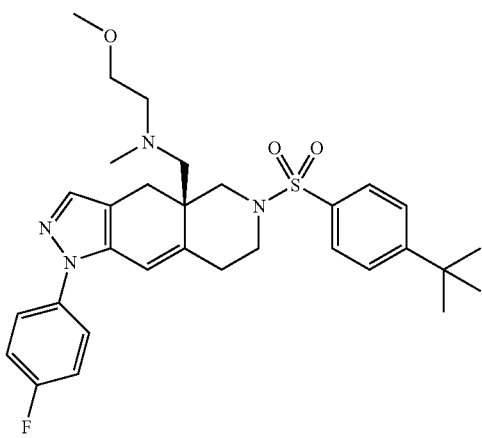

LC-MS (Method A): RT=2.91 min, (M+H)+ 567.

[(S)-6-(4-tert-Butyl-benzenesulfonyl)-1-(4-fluoro-phenyl)-1,4,5,6,7,8-hexahydro-1,2,6-triaza-cyclo-penta[b]naphthalen-4a-ylmethyl]-isopropyl-amine

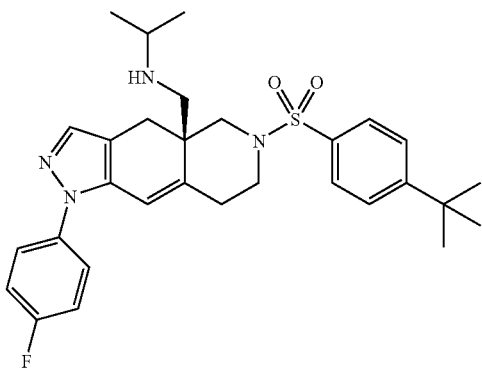

LC-MS (Method A): RT=2.88 min, (M+H)+ 537.

(S)-4a-Azetidin-1-ylmethyl-6-(4-tert-butyl-benzene-sulfonyl)-1-(4-fluoro-phenyl)-4,4a,5,6,7,8-hexahy-dro-1H-1,2,6-triaza-cyclopenta[b]naphthalene

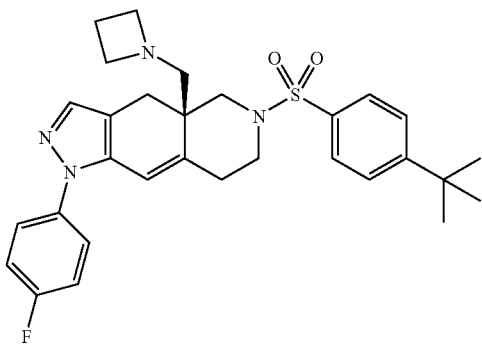

LC-MS (Method A): RT=2.85 min, (M+H)+ 535.

98

Allyl-[(S)-6-(4-tert-butyl-benzenesulfonyl)-1-(4-fluoro-phenyl)-1,4,5,6,7,8-hexahydro-1,2,6-triaza-cyclopenta[b]naphthalen-4a-ylmethyl]-amine

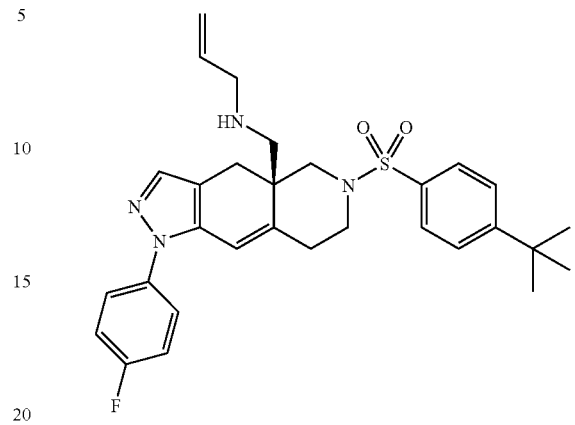

LC-MS (Method A): RT=2.71 min, (M+H)+ 535.

2-{[(S)-6-(4-tert-Butyl-benzenesulfonyl)-1-(4-fluoro-phenyl)-1,4,5,6,7-8-hexahydro-1,2,6-triaza-cyclopenta[b]naphthalen-4a-ylmethyl]-amino}-etha-nol

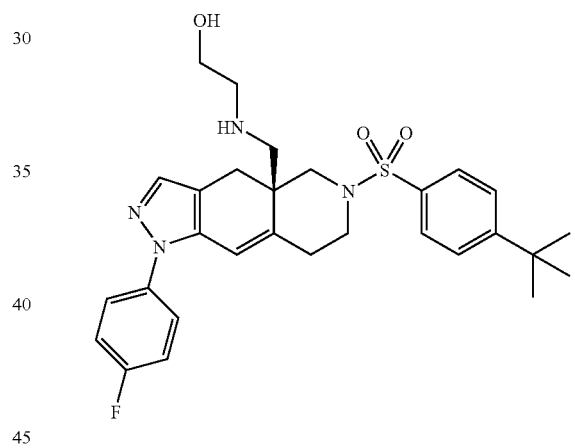

LC-MS (Method A): RT=2.74 min, (M+H)+ 539.

[(S)-1-(4-Fluoro-phenyl)-6-(toluene-4-sulfonyl)-1,4,5,6,7,8-hexahydro-1,2,6-triaza-cyclopenta[b]naph-thalen-4a-ylmethyl]-dimethyl-amine

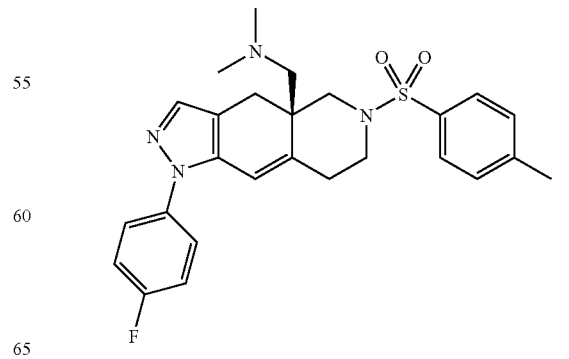

LC-MS (Method A): RT=2.50 min, (M+H)+ 481.

99

(S)-1-(4-Fluoro-phenyl)-4a-pyrrolidin-1-ylmethyl-6-(toluene-4-sulfonyl)-4,4a,5,6,7,8-hexahydro-1H-1,2,6-triaza-cyclopenta[b]naphthalene

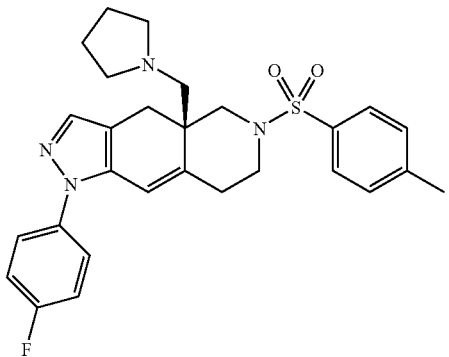

LC-MS (Method A): RT=2.55 min, (M+H)+ 507.

[(S)-6-(4-Fluoro-benzenesulfonyl)-1-(4-fluoro-phenyl)-1,4,5,6,7,8-hexahydro-1,2,6-triaza-cyclopenta[b]naphthalen-4a-ylmethyl]-dimethyl-amine

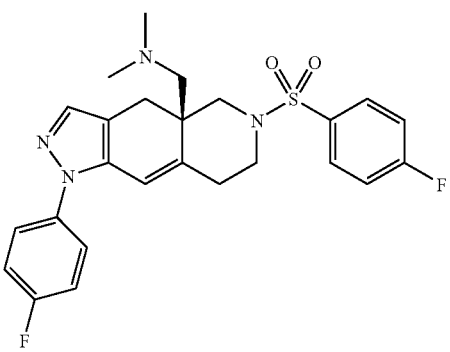

LC-MS (Method A): RT=2.45 min, (M+H)+ 485.

(S)-6-(4-Fluoro-benzenesulfonyl)-1-(4-fluoro-phenyl)-4a-pyrrolidin-1-ylmethyl-4,4a,5,6,7,8-hexahydro-1H-1,2,6-triaza-cyclopenta[b]naphthalene

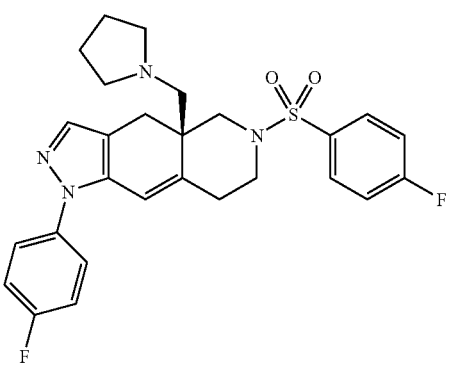

LC-MS (Method A): RT=2.51 min, (M+H)+ 511.

100

(S)-6-Benzenesulfonyl-1-(4-fluoro-phenyl)-4a-pyrrolidin-1-ylmethyl-4,4a,5,6,7,8-hexahydro-1H-1,2,6-triaza-cyclopenta[b]naphthalene

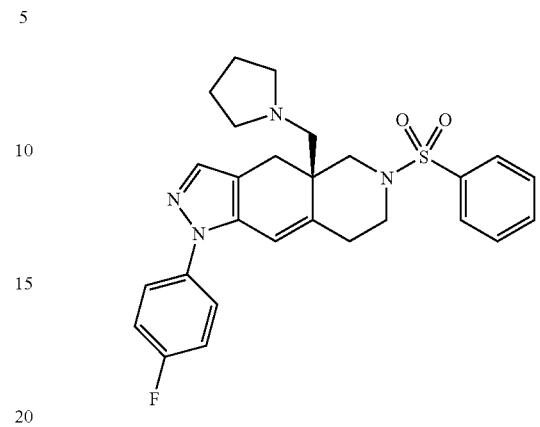

LC-MS (Method A): RT=2.49 min, (M+H)+ 492.

(S)-6-Benzenesulfonyl-1-(4-fluoro-phenyl)-1,4,5,6,7,8-hexahydro-1,2,6-triaza-cyclopenta[b]naphthalen-4a-ylmethyl]-dimethyl-amine

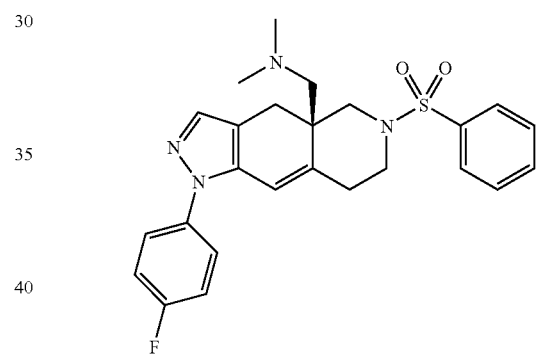

LC-MS (Method A): RT=2.41 min, (M+H)+ 467.

(S)-6-Benzenesulfonyl-1-(4-fluoro-phenyl)-4a-morpholin-4-ylmethyl-4,4a,5,6,7,8-hexahydro-1H-1,2,6-triaza-cyclopenta[b]naphthalene

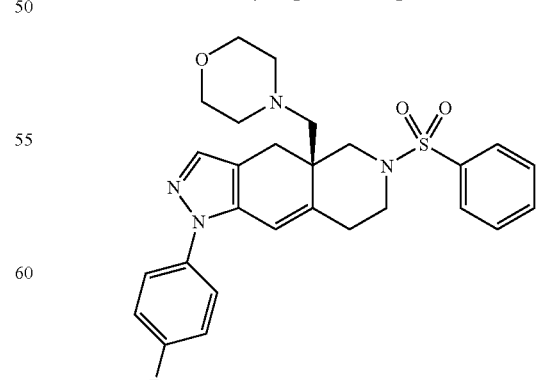

LC-MS (Method B): RT=9.11 min, (M+H)+ 509.

101

2-{[(S)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethyl]-methyl-amino}-ethanol

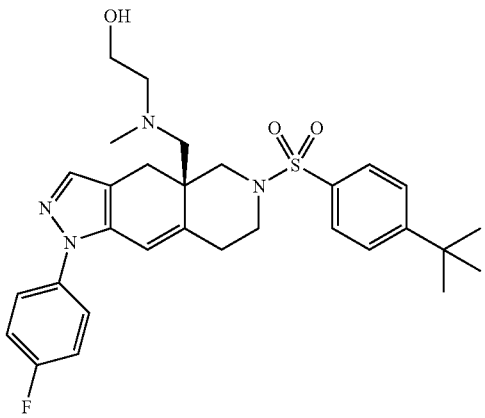

LC-MS (Method B): RT=8.90 min, (M+H)+ 553.

(S)-6-(Butane-1-sulfonyl)-1-(4-fluoro-phenyl)-4a-morpholin-4-ylmethyl-4,4a,5,6,7,8-hexahydro-1H-1,2,6-triaza-cyclopenta[b]naphthalene

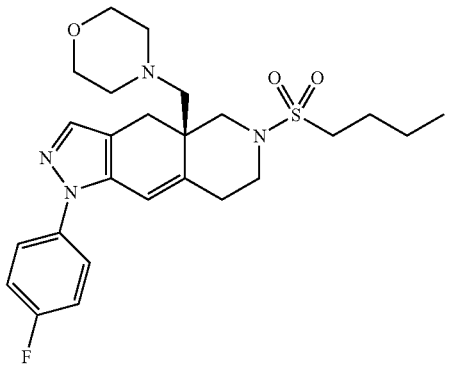

LC-MS (Method A): RT=2.74 min, (M+H)+ 489.

4-[(S)-1-(4-Fluoro-phenyl)-4a-morpholin-4-ylmethyl-1,4,4a,5,7,8-hexahydro-1,2,6-triaza-cyclopenta[b]naphthalene-6-sulfonyl]-benzonitrile

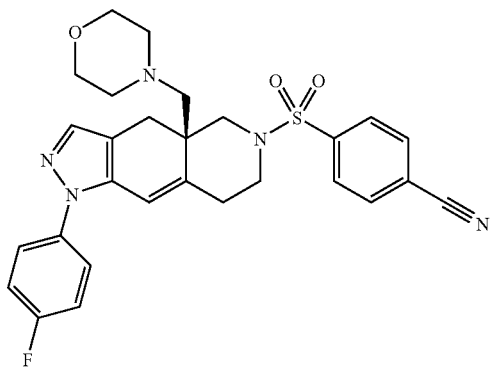

LC-MS (Method A): RT=2.97 min, (M+H)+ 534.

102

[(S)-6-Benzenesulfonyl-1-(4-fluoro-phenyl)-1,4,5,6,7,8-hexahydro-1,2,6-triaza-cyclopenta[b]naphthalen-4a-ylmethyl]-diethyl-amine

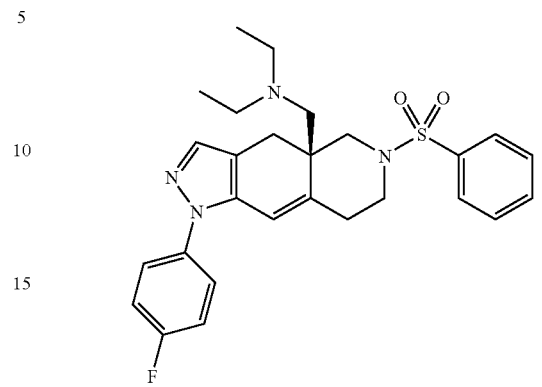

LC-MS (Method A): RT=2.50 min, (M+H)+ 495.

Diethyl-[(S)-1-(4-fluoro-phenyl)-6-(4-methoxy-benzenesulfonyl)-1,4,5,6,7,8-hexahydro-1,2,6-triaza-cyclopenta[b]naphthalen-4a-ylmethyl]-amine

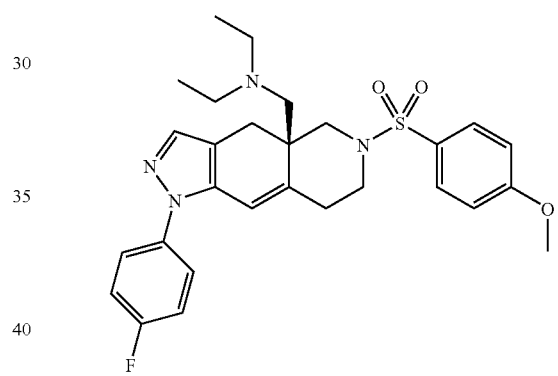

LC-MS (Method A): RT=2.56 min, (M+H)+ 525.

(S)-6-Benzenesulfonyl-1-(4-fluoro-phenyl)-4a-piperidin-1-ylmethyl-4,4a,5,6,7,8-hexahydro-1H-1,2,6-triaza-cyclopenta[b]naphthalene

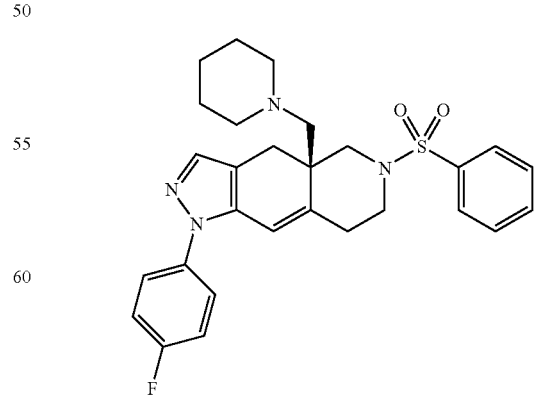

LC-MS (Method A): RT=2.52 min, (M+H)+ 507.

103

(S)-1-(4-Fluoro-phenyl)-6-(4-methoxy-benzene-
sulfonyl)-4a-piperidin-1-ylmethyl-4,4a,5,6,7,8-
hexahydro-1H-1,2,6-triaza-cyclopenta[b]naphthalene

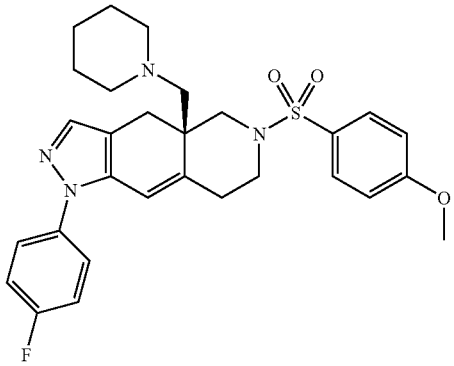

LC-MS (Method A): RT=2.57 min, (M+H)+ 537.

(S)-1-Butyl-4a-piperidin-1-ylmethyl-6-(toluene-4-
sulfonyl)-4,4a,5,6,7,8-hexahydro-1H-1,2,6-triaza-
cyclopenta[b]naphthalene

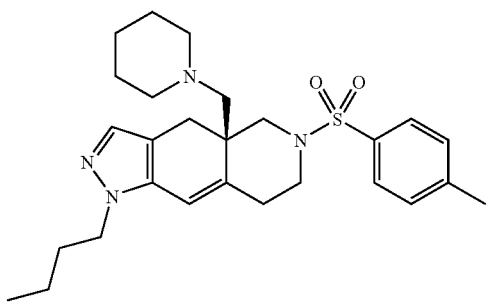

LC-MS (Method A): RT=2.54 min, (M+H)+ 483.

(S)-6-(4-tert-Butyl-benzenesulfonyl)-4a-pyrrolidin-
1-ylmethyl-1-(2,2,2-trifluoroethyl)-4,4a,5,6,7,8-
hexahydro-1H-1,2,6-triaza-cyclopenta[b]naphthalene

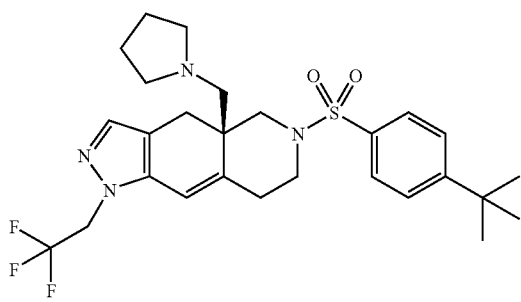

LC-MS (Method A): RT=2.74 min, (M+H)+ 537.

104

[(S)-1-Butyl-6-(4-tert-butyl-benzenesulfonyl)-1,4,5,
6,7,8-hexahydro-1,2,6-triaza-cyclopenta[b]naphtha-
len-4a-ylmethyl]-dimethyl-amine

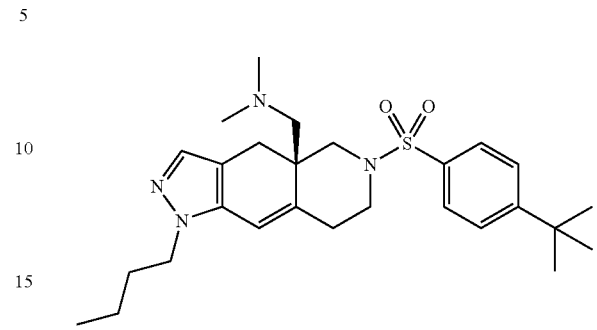

LC-MS (Method A): RT=2.76 min, (M+H)+ 485.

(S)-1-Butyl-6-(4-tert-butyl-benzenesulfonyl)-4a-
piperidin-1-ylmethyl-4,4a,5,6,7,8-hexahydro-1H-1,2,
6-triaza-cyclopenta[b]naphthalene

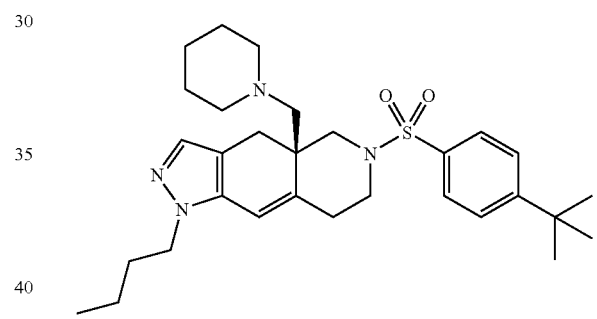

LC-MS (Method A): RT=2.85 min, (M+H)+ 525.

[(S)-6-(4-tert-Butyl-benzenesulfonyl)-1-isopropyl-1,
4,5,6,7,8-hexahydro-1,2,6-triaza-cyclopenta[b]naph-
thalen-4a-ylmethyl]-dimethyl-amine

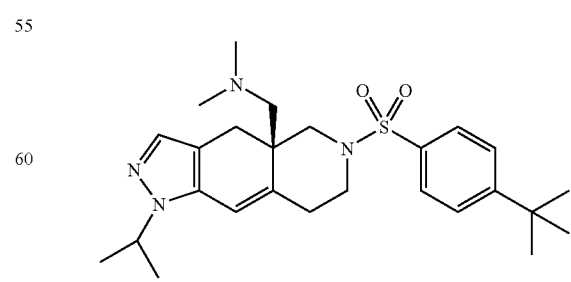

LC-MS (Method A): RT=2.47 min, (M+H)+ 471.

105

(S)-6-(4-tert-Butyl-benzenesulfonyl)-1-isopropyl-4a-piperidin-1-ylmethyl-4,4a,5,6,7,8-hexahydro-1H-1,2,6-triaza-cyclopenta[b]naphthalene

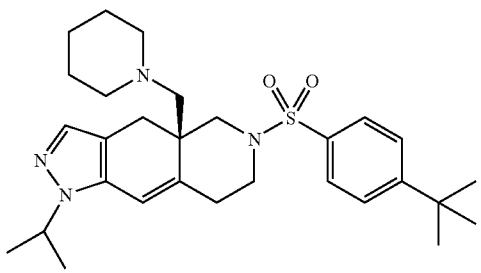

LC-MS (Method A): RT=2.58 min, (M+H)$^+$ 511.

(S)-1-(4-Fluoro-phenyl)-4a-morpholin-4-ylmethyl-6-(toluene-2-sulfonyl)-4,4a,5,6,7,8-hexahydro-1H-1,2,6-triaza-cyclopenta[b]naphthalene

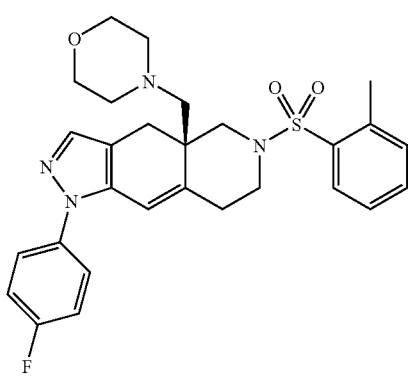

LC-MS (Method B): RT=9.18 min, (M+H)$^+$ 523.

(S)-6-(2-Fluoro-benzenesulfonyl)-1-(4-fluoro-phenyl)-4a-morpholin-4-ylmethyl-4,4a,5,6,7,8-hexahydro-1H-1,2,6-triaza-cyclopenta[b]naphthalene

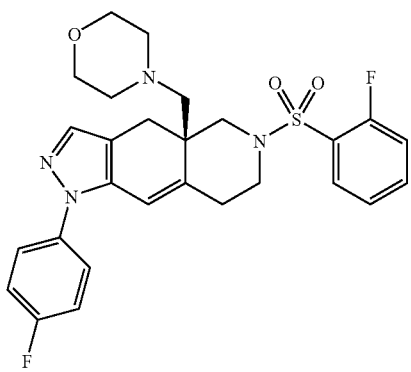

LC-MS (Method B): RT=8.67 min, (M+H)$^+$ 527.

106

(S)-1-(4-Fluoro-phenyl)-4a-morpholin-4-ylmethyl-6-(pyridine-2-sulfonyl)-4,4a,5,6,7,8-hexahydro-1H-1,2,6-triaza-cyclopenta[b]naphthalene

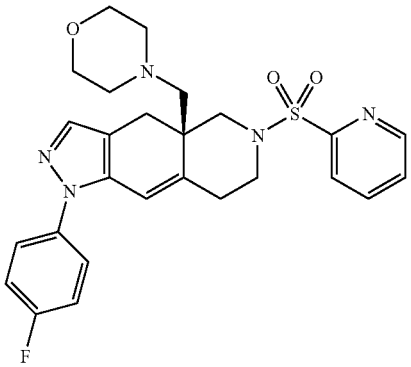

LC-MS (Method B): RT=7.27 min, (M+H)$^+$ 510.

Example 39

(4aR,8aS)-1-(4-Fluoro-phenyl)-1,4,7,8,8a,9-hexahydro-1,2,6-triaza-cyclopenta[b]naphthalene-4a,6-dicarboxylic acid 6-tert-butyl ester 4a-methyl ester (49B: R$^5$=4-F-Ph; L$^2$-R$^2$=CO$_2$-t-Butyl)

A solution of compound 49A (R$^5$=4-F-Ph; L$^2$-R$^2$=CO$_2$-t-butyl) (400 mg, 0.94 mmol) in methanol (10 mL) was treated with platinum oxide (32 mg, 0.14 mmol) and stirred under a hydrogen atmosphere for 2 h. The solution was filtered and the filtrate was evaporated to dryness to afford 412 mg of the title compound as a colorless oil which was used in subsequent examples without further purification. LC-MS (Method A): RT=3.74 min, (M+H)$^+$ 430.

Example 40

(4aR,8aS)-6-(4-tert-Butyl-benzenesulfonyl)-1-(4-fluoro-phenyl)-1,4,5,6,7,8,8a,9-octahydro-1,2,6-triaza-cyclopenta[b]naphthalene-4a-carboxylic acid methyl ester (49B: $R^5$=4-F-Ph; $L^2$-$R^2$=$SO_2$(4-t-Butylphenyl)

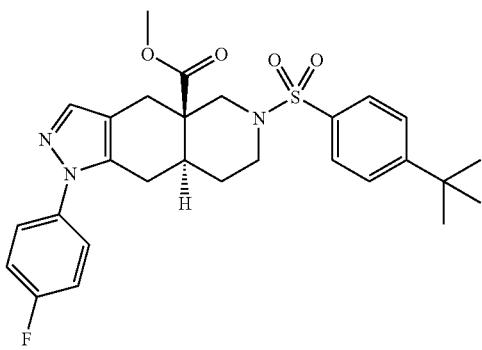

To compound 49B ($R^5$=4-F-Ph; $L^2$-$R^2$=$CO_2$-t-butyl) (404 mg, 0.94 mmol) was added a 20% solution of TFA in $CH_2Cl_2$ (4 mL) and the contents were stirred at ambient temperature for 1 h. The solvents were then removed. The residue was dissolved in $CH_2Cl_2$ (4 mL) and diisopropylethyl amine (485 µL, 2.79 mmol) and 4-tert-butylphenylsulfonyl chloride (540 mg, 2.32 mmol) were added and the contents were stirred for 3 h. Water (10 mL) was added and the organics were extracted with EtOAc (15 mL), washed with brine and dried ($MgSO_4$). Purification by flash chromatography ($CH_2Cl_2$ 100% to 40% EtOAc in $CH_2Cl_2$) to afforded 352 mg of the title compound as a yellow foam. LC-MS (Method A): RT=4.36 min, (M+H)$^+$ 526.

Example 41

[(4aR,8aS)-6-(4-tert-Butyl-benzenesulfonyl)-1-(4-fluoro-phenyl)-1,4,5,6,7,8,8a,9-octahydro-1,2,6-triaza-cyclopenta[b]naphthalen-4a-yl]-methanol (50B: $R^5$=4-F-Ph; $L^2$-$R^2$=$SO_2$(4-t-butylphenyl)

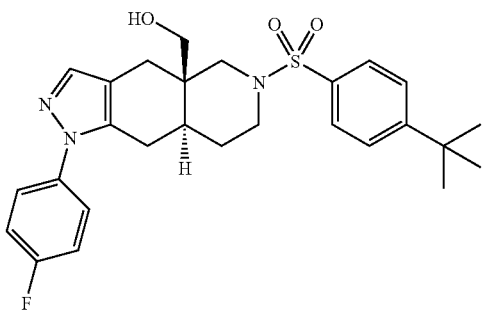

To compound 49B ($R^5$=4-F-Ph; $L^2$-$R^2$=$SO_2$(4-t-butylphenyl) (500 mg, 0.95 mmol) in $CH_2Cl_2$ (10 mL) was added DIBAL-H (3.8 mL, 1.0 M solution, 3.80 mmol) at −78° C. and the contents were stirred for 1 h. The reaction was quenched by the addition of water (10 mL). The organics were extracted with $CH_2Cl_2$ (50 mL) and washed with brine and dried ($MgSO_4$). Purification by flash chromatography ($CH_2Cl_2$ 100% to 5% EtOAc in $CH_2Cl_2$) afforded 286 mg of the title compound as white solid. LC-MS (Method A): RT=4.14 min, (M+H)$^+$ 496.

Example 42

(4aR,8aS)-6-(4-tert-Butyl-benzenesulfonyl)-1-(4-fluoro-phenyl)-4a-methoxymethyl-4,4a,5,6,7,8,8a,9-octahydro-1H-1,2,6-triaza-cyclopenta[b]naphthalene (51B: $R^{14}$=Me; $R^5$=4-F-Ph; $L^2$-$R^2$=$SO_2$(4-t-butylphenyl)

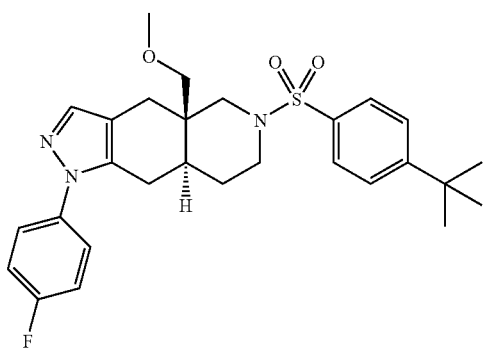

To compound 50B ($R^5$=4-F-Ph; $L^2$-$R^2$=$SO_2$(4-t-butylphenyl) (40 mg, 0.08 mmol) in THF (1 mL) was added a sodium hydride (10 mg, 0.24 mmol) and iodomethane (15 µL, 0.24 mmol) and the contents were stirred at 70° C. for 18 h. The cooled contents were partitioned between EtOAc (10 mL) and water (10 mL) and washed with brine and dried ($MgSO_4$). Purification by flash chromatography ($CH_2Cl_2$ 100% to 5% EtOAc in $CH_2Cl_2$) afforded 21 mg of the title compound as white solid. LC-MS (Method B): RT=14.12 min, (M+H)$^+$ 512.

The following compounds were similarly prepared:

(4aR,8aS)-6-(4-tert-Butyl-benzenesulfonyl)-1-(4-fluoro-phenyl)-4a-(2-methoxy-ethoxymethyl)-4,4a,5,6,7,8,8a,9-octahydro-1H-1,2,6-triaza-cyclopenta[b]naphthalene

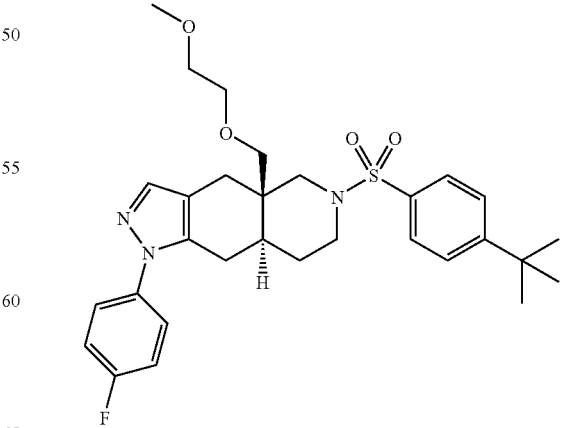

LC-MS (Method B): RT=14.04 min, (M+H)$^+$ 556.

(4aR,8aS)-6-Benzenesulfonyl-1-(4-fluoro-phenyl)-
4a-(2-methoxy-ethoxymethyl)-4,4a,5,6,7,8,8a,9-
octahydro-1H-1,2,6-triaza-cyclopenta[b]naphthalene

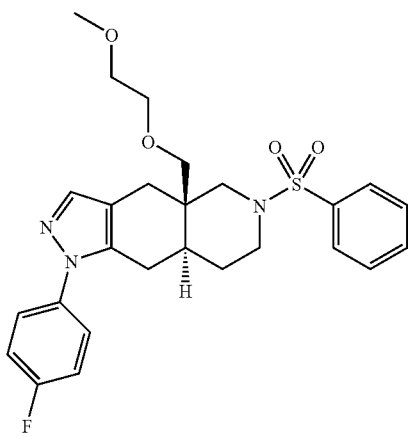

LC-MS (Method B): RT=11.92 min, (M+H)+ 500.

(4aR,8aS)-6-Benzenesulfonyl-1-(4-fluoro-phenyl)-
4a-methoxymethyl 4,4a,5,6,7,8,8a,9-octahydro-1H-
1,2,6-triaza-cyclopenta[b]naphthalene

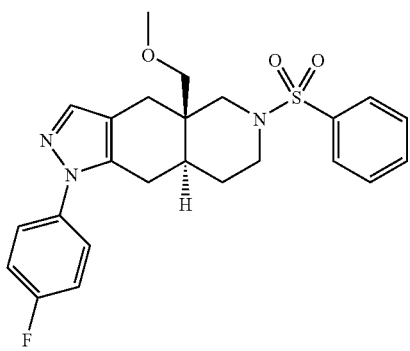

LC-MS (Method B): RT=12.06 min, (M+H)+ 456.

Example 43

(R)-6-(4-tert-Butyl-benzenesulfonyl)-1-(4-fluoro-
phenyl)-1,4,5,6,7,8-hexahydro-1,2,6-triaza-cyclo-
penta[b]naphthalene-4a-carboxylic acid (54A: $R^5$=4-
F-Ph; $L^2$-$R^2$=SO$_2$(4-t-butylphenyl)

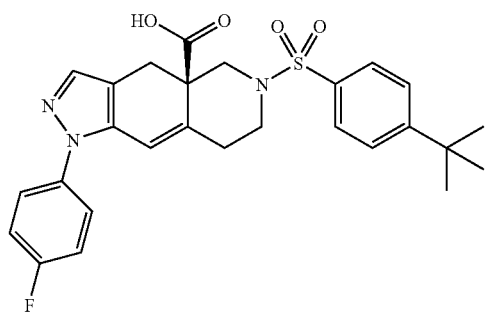

A solution of compound 49A ($R^5$=4-F-Ph; $L^2$-$R^2$=SO$_2$(4-t-butylphenyl) (545 mg, 1.04 mmol) in methanol (10 mL) was treated with 1M LiOH (3.1 mL, 3.12 mmol) and the contents were stirred at ambient temperature for 18 h. The solvents were removed and the residue was dissolved in CH$_2$Cl$_2$, washed with 1 M citric acid and dried (MgSO$_4$). Removal of solvent gave 504 mg of the title compound as a yellow solid, which was used in subsequent examples without further purification. LC-MS (Method A): RT=4.06 min, (M+H)+ 510.

Example 44

(R)-6-(4-tert-Butyl-benzenesulfonyl)-1-(4-fluoro-
phenyl)-1,4,5,6,7,8-hexahydro-1,2,6-triaza-cyclo-
penta[b]naphthalene-4a-carboxylic acid benzylamide
(55A: $R^{1C}$=H; $R^{1D}$=Benzyl; $R^5$=4-F-Ph;
$L^2$-$R^2$=SO$_2$(4-t-butylphenyl)

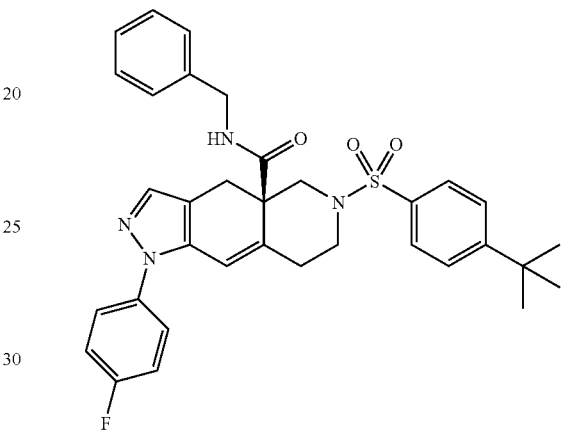

To a solution of compound 54A ($R^5$=4-F-Ph; $L^2$-$R^2$=SO$_2$(4-t-butylphenyl) (50 mg, 0.09 mmol) in DMF (1 mL) was added benzylamine (16 mL, 0.15 mmol), diisopropylethylamine (51 mL, 0.29 mmol) and HATU (45 mg, 0.19 mmol) and the contents were stirred at ambient temperature for 18 h. Water (5 mL) was added and the organics were extracted with EtOAc (5 mL), washed with brine and dried (MgSO$_4$). Purification by flash chromatography (CH$_2$Cl$_2$ 100% to 5% EtOAc in CH$_2$Cl$_2$) afforded 89 mg of the title compound as a white solid. LC-MS (Method A): RT=4.33 min, (M+H)+ 599.

The following compounds were similarly prepared:

[(R)-6-(4-tert-Butyl-benzenesulfonyl)-1-(4-fluoro-
phenyl)-1,4,5,6,7,8-hexahydro-1,2,6-triaza-cyclo-
penta[b]naphthalen-4a-yl]-morpholin-4-yl-metha-
none

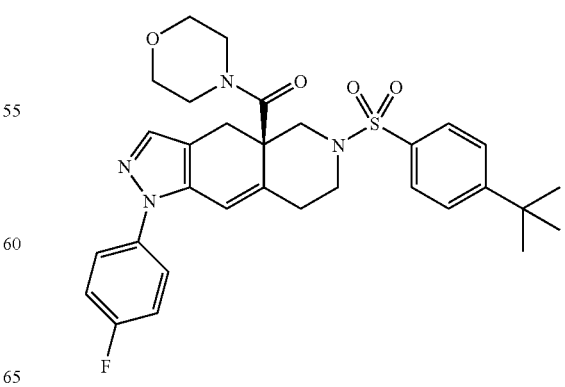

LC-MS (Method A): RT=3.86 min, (M+H)+ 579.

111

[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-piperidin-1-yl-methanone

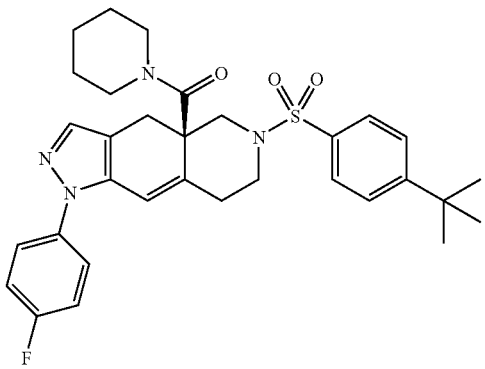

LC-MS (Method A): RT=4.33 min, (M+H)+ 577.

[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-pyrrolidin-1-yl-methanone

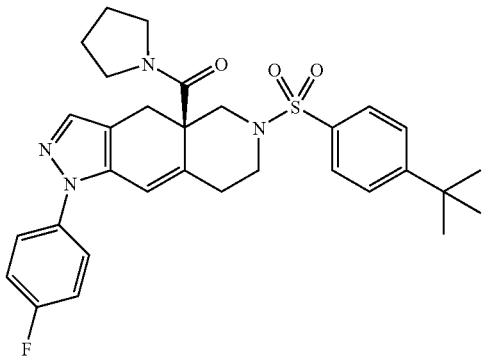

LC-MS (Method A): RT=4.14 min, (M+H)+ 563.

(R)-6-(4-tert-Butyl-benzenesulfonyl)-1-(4-fluoro-phenyl)-1,4,5,6,7,8-hexahydro-1,2,6-triaza-cyclopenta[b]naphthalene-4a-carboxylic acid ethylamide

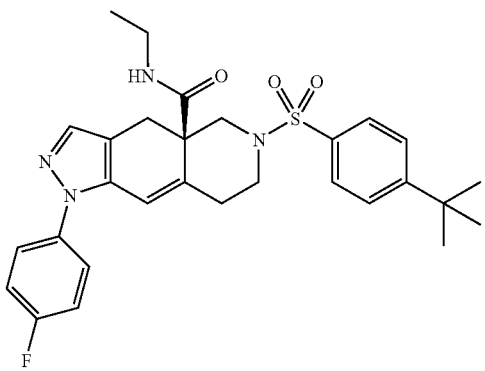

LC-MS (Method A): RT=4.08 min, (M+H)+ 537.

112

(R)-6-(4-tert-Butyl-benzenesulfonyl)-1-(4-fluoro-phenyl)-1,4,5,6,7,8-hexahydro-1,2,6-triaza-cyclopenta[b]naphthalene-4a-carboxylic acid dimethylamide

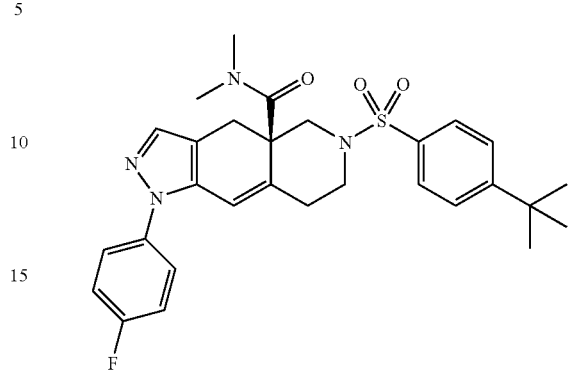

LC-MS (Method A): RT=4.03 min, (M+H)+ 537.

Example 45

1-[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-ethanol (56A: $R^1$=Me; $R^5$=4-F-Phenyl; $L^2$-$R^2$=$SO_2$(4-t-butylphenyl)

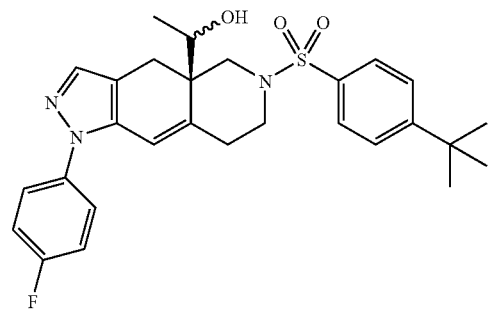

A 3M solution of methylmagnesium bromide (294 μL, 0.88 mmol) was added to a solution of compound 52A ($R^5$=4-F-phenyl; $L^2$-$R^2$=$SO_2$(4-t-butylphenyl) (44 mg, 0.09 mmol) in THF (3 mL) and the contents were stirred at ambient temperature for 4 h. A saturated solution of $NH_4Cl$ was added and the contents were partitioned between diethyl ether (10 mL) and water (5 mL). The organics were extracted with EtOAc (5 mL), washed with brine and dried ($MgSO_4$). Purification by flash chromatography ($CH_2Cl_2$ 100% to 5% EtOAc in $CH_2Cl_2$) afforded 10 mg of the title compound as a white solid. LC-MS (Method A): RT=4.25 min, (M+H)+ 510.
The following compounds were similarly prepared:

1-[(R)-6-(4-tert-Butyl-benzenesulfonyl)-1-(4-fluoro-phenyl)-1,4,5,6,7,8-hexahydro-1,2,6-triaza-cyclo-penta[b]naphthalen-4a-yl]-propan-1-ol

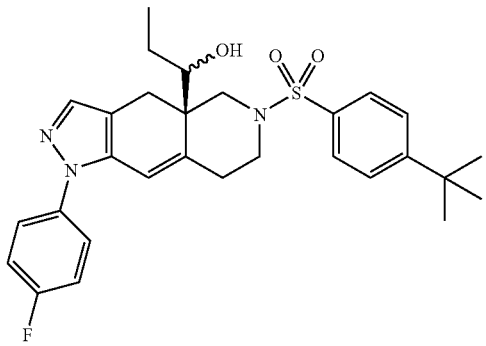

LC-MS (Method A): RT=4.29 min, (M+H)+ 524.

[(R)-6-(4-tert-Butyl-benzenesulfonyl)-1-(4-fluoro-phenyl)-1,4,5,6,7,8-hexahydro-1,2,6-triaza-cyclo-penta[b]naphthalen-4a-yl]-phenyl-methanol

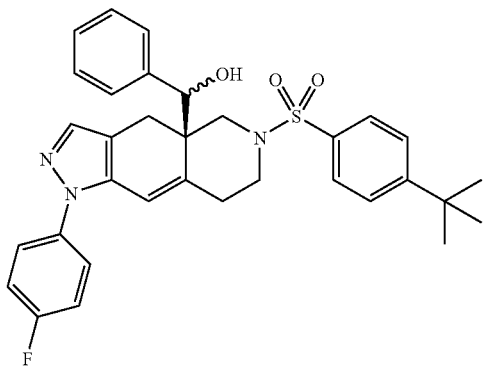

LC-MS (Method A): RT=4.52 min, (M+H)+ 572.

Example 46

[(R)-6-(4-tert-Butyl-benzenesulfonyl)-1-(4-fluoro-phenyl)-1,4,5,6,7,8-hexahydro-1,2,6-triaza-cyclo-penta[b]naphthalen-4a-yl]-phenyl-methanone (57A: $R^1$=Ph; $R^5$=4-F-Ph; $L^2$-$R^2$=$SO_2$(4-t-butylphenyl)

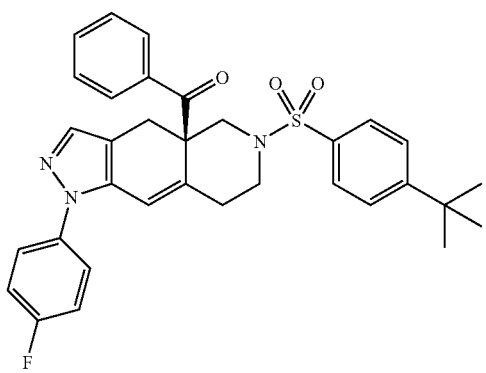

Oxalyl chloride (15 µL, 0.17 mmol) in $CH_2Cl_2$ (1 mL) was cooled to −78° C. and DMSO (26 µL, 0.37 mmol) in $CH_2Cl_2$ (0.5 mL) was added. After 5 min, compound 56A ($R^5$=4-F-Ph; $L^2$-$R^2$=$SO_2$(4-t-butylphenyl) (44 mg, 0.08 mmol) was added and the contents were stirred for 20 min. Triethylamine (54 µL, 0.38 mmol) was added and the contents were warmed to ambient temperature. The organics were partitioned between EtOAc (10 mL) and water (10 mL) and washed with brine and dried ($MgSO_4$). Purification by flash chromatography ($CH_2Cl_2$ 100% to 15% EtOAc in $CH_2Cl_2$) afforded 18 mg of the title compound as colorless oil. LC-MS (Method A): RT=4.56 min, (M+H)+ 570.

Example. 47

(R)-1-Butyl-6-(toluene-4-sulfonyl)-1,4,5,6,7,8-hexahydro-1,2,6-triaza-cyclopenta[b]naphthalene-4a-carboxylic acid methyl ester (44A: $R^5$=n-Butyl; $L^1$-$R^1$=$CO_2Me$; $L^2$-$R^2$=$SO_2$(4-Methylphenyl)

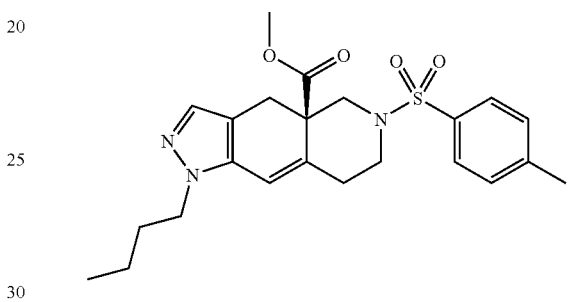

To compound 43A ($L^1$-$R^1$=$CO_2Me$; $L^2$-$R^2$=$SO_2$(4-methylphenyl)) (145 mg, 0.37 mmol) in ethanol (1 mL) was added N-butyl hydrazinecarboxylic acid tert-butyl ester (70 mg, 0.37 mmol) (prepared as in J. Org. Chem. 2002, 67, 8962-8969) in ethanol (4 mL) and the contents were stirred at 80° C. for 2 h. The solvents were then removed. The residue was dissolved in dichloroethane (4 mL) and TFA (1 mL) was added and the contents were stirred at 60° C. for 1 h. Saturated aqueous $NaHCO_3$ (5 mL) was added and the organics were extracted with $CH_2Cl_2$ (3×5 mL), washed with brine and dried ($MgSO_4$). Purification by flash chromatography ($CH_2Cl_2$ 100% to 30% EtOAc in $CH_2Cl_2$) afforded 135 mg of the title compound as a white solid. LC-MS (Method B): RT=16.71 min, (M+H)+ 444.

The following compound was similarly prepared:

(R)-6-(4-Methyl-benzenesulfonyl)-1-(cyclopentyl)-4a-(2-methoxy-ethoxymethyl)-4,4a,5,6,7,8-hexahydro-1H-1,2,6-triaza-cyclopenta[b]naphthalene

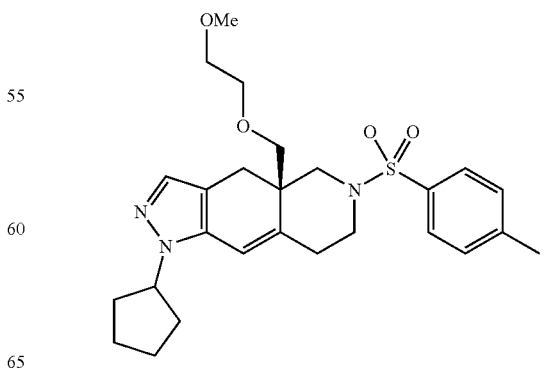

LC-MS (Method A) (M+H)+ 486.

Example 48

(R)-6-(4-tert-Butyl-benzenesulfonyl)-4a-[1,3]
dithian-2-ylidenemethyl-1-(4-fluoro-phenyl)-4,4a,5,
6,7,8-hexahydro-1H-1,2,6-triaza-cyclopenta[b]naph-
thalene (58A: $R^5$=4-F-Ph; $L^2$-$R^2$=$SO_2$(4-t-
butylphenyl)

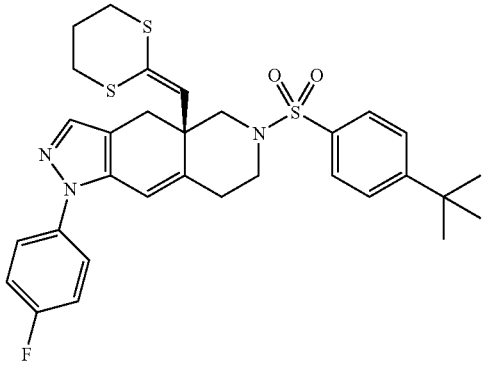

2-Trimethylsilyl-1,3-dithiane (189 mL, 0.99 mmol) in THF (2 mL) was cooled to 0° C. and n-BuLi (0.62 mL, 0.99 mmol) was added. After 10 min, the temperature was lowered to −78° C. and a solution of compound 54A ($R^5$=4-F-Ph; $L^2$-$R^2$=$SO_2$(4-t-butylphenyl) (232 mg, 0.47 mmol) was added. After 30 min brine (5 mL) was added and the organics were extracted with $CH_2Cl_2$ (5 mL) and dried ($MgSO_4$). Purification by flash chromatography ($CH_2Cl_2$ 100% to 10% EtOAc in $CH_2Cl_2$) afforded 168 mg of the title compound as a white solid. LC-MS (Method A): RT=4.27 min, (M+H)$^+$ 596.

Example 49

[(R)-6-(4-tert-Butyl-benzenesulfonyl)-1-(4-fluoro-
phenyl)-1,4,5,6,7,8-hexahydro-1,2,6-triaza-cyclo-
penta[b]naphthalen-4a-yl]-acetic acid methyl ester
(59A: $R^5$=4-F-Ph; $L^2$-$R^2$=$SO_2$(4-t-butylphenyl)

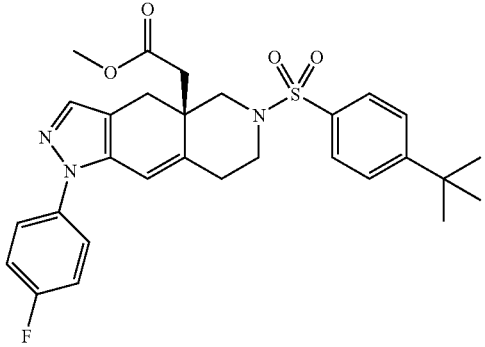

To compound 58A ($R^5$=4-F-Ph; $L^2$-$R^2$=$SO_2$(4-t-butylphenyl) (165 mg, 0.28 mmol) in methanol (12 mL) was added perchloric acid (86 μL, 1.42 mmol) and mercury$^{II}$ chloride (301 mg, 1.11 mmol) and the contents were heated at reflux for 2.5 h. The cooled solution was filtered and the filtrate was concentrated. Purification by flash chromatography ($CH_2Cl_2$ 100% to 30% EtOAc in $CH_2Cl_2$) afforded 168 mg of the title compound as a white solid. LC-MS (Method A): RT=4.38 min, (M+H)$^+$ 538.

Example 50

2-[(R)-6-(4-tert-Butyl-benzenesulfonyl)-1-(4-fluoro-
phenyl)-1,4,5,6,7,8-hexahydro-1,2,6-triaza-cyclo-
penta[b]naphthalen-4a-yl]-ethanol (60A: $R^5$=4-F-Ph;
$L^2$-$R^2$=$SO_2$(4-t-butylphenyl)

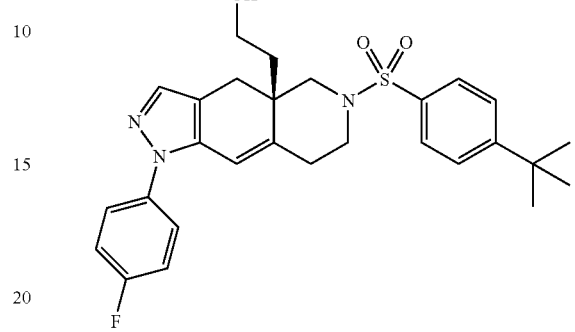

To compound 59A ($R^5$=4-F-Ph; $L^2$-$R^2$=$SO_2$(4-t-butylphenyl) (128 mg, 0.24 mmol) in $CH_2Cl_2$ (2.5 mL) was added DIBAL-H (950 μL, 1.0 M solution, 0.95 mmol) at −78° C. and the contents were stirred for 1 h. The reaction was quenched by the addition of water (5 mL). The organics were extracted with $CH_2Cl_2$ (20 mL), washed with brine and dried ($MgSO_4$). Purification by flash chromatography ($CH_2Cl_2$ 100% to 30% EtOAc in $CH_2Cl_2$) afforded 104 mg of the title compound as a white solid. LC-MS (Method A): RT=3.90 min, (M+H)$^+$ 510.

Example 51

(R)-6-(4-tert-Butyl-benzenesulfonyl)-1-(4-fluoro-
phenyl)-4a-(2-methoxy-ethyl)-4,4a,5,6,7,8-hexahy-
dro-1H-1,2,6-triaza-cyclopenta[b]naphthalene (61A:
$R^{1A}$=Me; $R^5$=4-F-Ph; $L^2$-$R^2$=$SO_2$(4-t-butylphenyl)

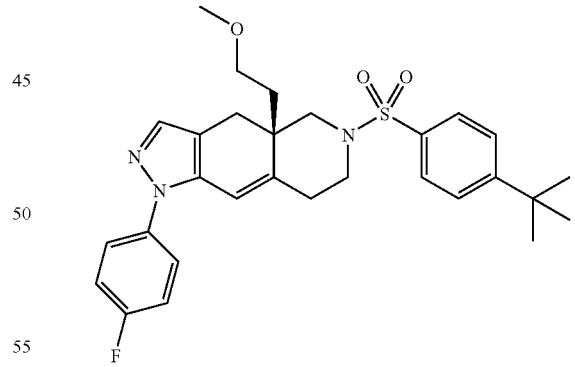

To compound 60A ($R^5$=4-F-Ph; $L^2$-$R^2$=$SO_2$(4-t-butylphenyl) (32 mg, 0.06 mmol) in THF (1 mL) was added a sodium hydride (7.5 mg, 0.19 mmol) and iodomethane (12 μL, 0.19 mmol) and the contents were stirred at 75° C. for 18 h. The cooled contents were partitioned between EtOAc (10 mL) and water (10 mL), washed with brine and dried ($MgSO_4$). Purification by flash chromatography ($CH_2Cl_2$ 100% to 15% EtOAc in $CH_2Cl_2$) afforded 12 mg of the title compound as colorless glass. LC-MS (Method A): RT=4.43 min, (M+H)$^+$ 524.

Example 52

[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-acetaldehyde (62A: R5=4-F-Ph; $L^2$-$R^2$=SO$_2$(4-t-butylphenyl)

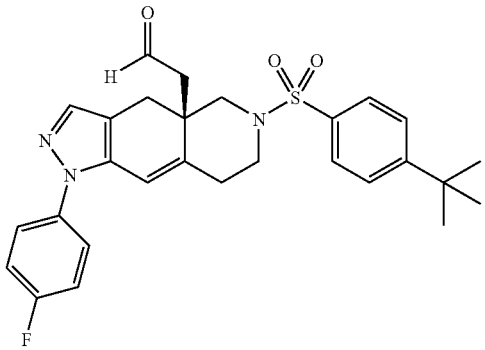

Oxalyl chloride (29 µL, 0.22 mmol) in CH$_2$Cl$_2$ (2 mL) was cooled to −78° C. and DMSO (38 µL, 0.48 mmol) in CH$_2$Cl$_2$ (1 mL) was added. After 5 min, compound 60A (R$^5$=4-F-Ph; $L^2$-$R^2$=SO$_2$(4-t-butylphenyl) (50 mg, 0.10 mmol) was added and the contents were stirred for 20 min. Triethylamine (51 µL, 0.50 mmol) was added and the contents were warmed to ambient temperature. The organics were partitioned between EtOAc (10 mL) and water (10 mL), washed with brine and dried (MgSO$_4$). Purification by flash chromatography (CH$_2$Cl$_2$ 100% to 5% EtOAc in CH$_2$Cl$_2$) afforded 35 mg of the title compound as white solid. LC-MS (Method A): RT=3.87 min, (M+H)$^+$ 508.

Example 53

{2-[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-ethyl}-dimethylamine (63A: $R^{1C}$=$R^{1D}$=Me; R$^5$=4-F-Ph; $L^2$-$R^2$=SO$_2$(4-t-butylphenyl)

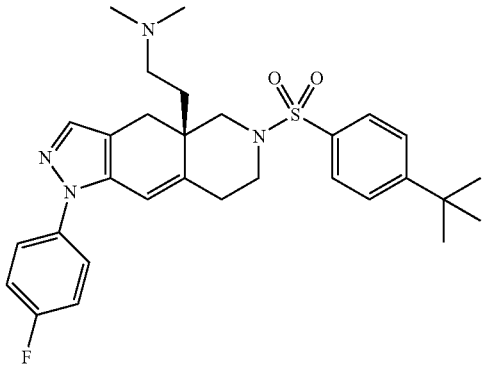

To a solution of compound 62A (R$^5$=4-F-Ph; $L^2$-$R^2$=SO$_2$(4-t-butylphenyl) (35 mg, 0.07 mmol) in dichloroethane (1 mL) was added dimethylamine (0.10 mL, 0.21 mmol) and sodium triacetoxyborohydride (22 mg, 0.11 mmol). The contents were stirred for 18 h at ambient temperature, NaHCO$_3$ (2 mL) was added, and the organics were extracted with CH$_2$Cl$_2$ (10 mL), washed with brine and dried (MgSO$_4$). Purification by flash chromatography (Amino-SPE: CH$_2$Cl$_2$ 100% to 5% EtOAc in CH$_2$C$_2$) afforded 61 mg of the title compound as an off white solid. LC-MS (Method A): RT=2.68 min, (M+H)$^+$ 537.

The following compound was similarly prepared:

(R)-6-(4-tert-Butyl-benzenesulfonyl)-1-(4-fluoro-phenyl)-4a-(2-pyrrolidin-1-yl-ethyl)-4,4a,5,6,7,8-hexahydro-1H-1,2,6-triaza-cyclopenta[b]naphthalene

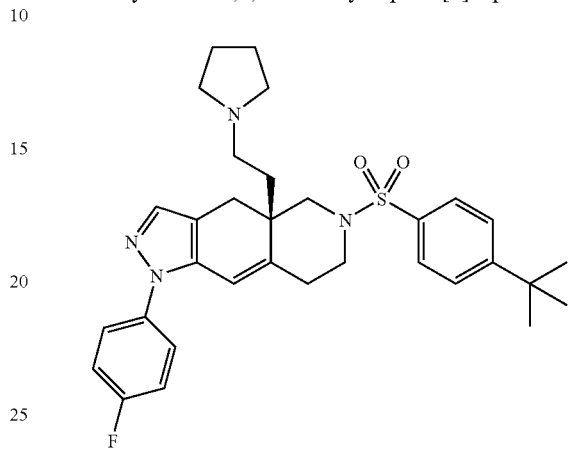

LC-MS (Method A): RT=2.93 min, (M+H)$^+$ 563.

Example 54

(4aS,8aS)-1-(4-Fluoro-phenyl)-4a-morpholin-4-ylmethyl-1,4,4a,5,7,8,8a,9-octahydro-1,2,6-triaza-cyclopenta[b]naphthalene-6-carboxylic acid tert-butyl ester (44B: $L^1$=CH$_2$; R$^1$=Morpholine; $L^2$=CO$_2$-t-Butyl)

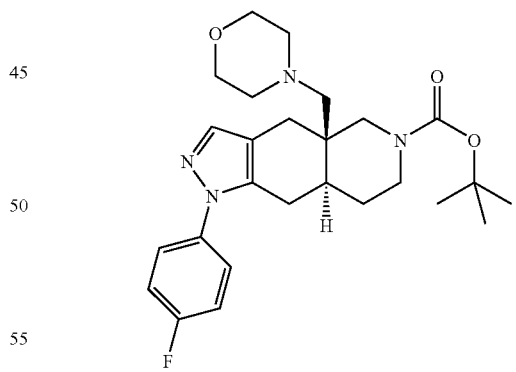

A mixture of compound 44A ($L^1$=CH$_2$; R$^1$=morpholine; $L^2$=CO$_2$-t-butyl) (125 mg, 0.27 mmol) and platinum oxide (9 mg, 0.04 mmol) in methanol (3 mL) was stirred for 2.5 h at ambient temperature under an atmosphere of hydrogen. The solution was filtered and the filtrate was evaporated to dryness. The residue was purified by preparative HPLC to yield the title compound as a white solid, 22 mg, LC-MS: RT=2.48 min, (M+H)$^+$ 471, together with the cis-regioisomer, 35 mg, LC-MS (Method A): RT=2.61 min, (M+H)$^+$ 471.

Example 55

(4aS,8aS)-6-(4-tert-Butyl-benzenesulfonyl)-1-(4-fluoro-phenyl)-4a-morpholin-4-ylmethyl-4,4a,5,6,7,8,8a,9-octahydro-1H-1,2,6-triazacyclopenta[b]naphthalene (44B: $L^1$=$CH_2$; $R^1$=Morpholine; $L^2$-$R^2$=$SO_2$(4-butylphenyl))

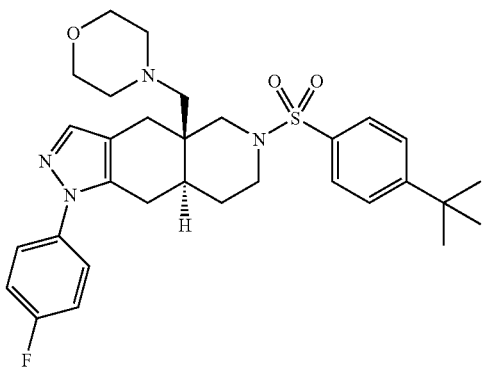

To compound 44B ($L^1$=$CH_2$; $R^1$=morpholine; $L^2$=$CO_2$-t-butyl) (22 mg, 0.05 mmol) was added a 20% solution of TFA in $CH_2Cl_2$ (1 mL) and the contents were stirred at ambient temperature for 1 h. The solvents were then removed. The residue was dissolved in $CH_2Cl_2$ (1 mL) and diisopropylethyl amine (41 µL, 0.23 mmol) and 4-tert-butylphenylsulfonyl chloride (22 mg, 0.09 mmol) were added and the contents were stirred for 18 h. Water (5 mL) was added and the organics extracted with EtOAc (5 mL), washed with brine and dried ($MgSO_4$). Purification by flash chromatography ($CH_2Cl_2$ 100% to 40% EtOAc in $CH_2Cl_2$) afforded 36 mg of the title compound as a white solid. LC-MS (Method B): RT=9.84 min, $(M+H)^+$ 567.

Example 56

4a-Benzyl-1-(4-fluoro-phenyl)-4,4a,5,6,7,8-hexahydro-1H-1,2-diaza-6-azonia-cyclopenta[b]naphthalene hydrochloride (65A: $R^5$=4-F-Phenyl; $L^1$-$R^1$=Benzyl)

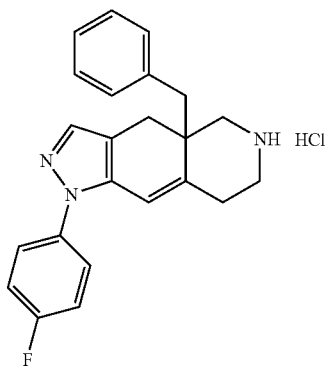

Compound 64A ($R^5$=4-F-phenyl; $L^1$-$R^1$=benzyl) (41 mg, 0.10 mmol) and ACE-Cl (20 µL, 0.18 mmol) were heated in dichloroethane (0.25 mL) at reflux for 18 h. The contents were cooled and the solvent was removed. The residue was dissolved in methanol (1 mL) and the contents were heated for 3 h at reflux. The solvent was removed to afford 21 mg of the title compound as a colorless glass which was used in subsequent examples without further purification. LC-MS (Method A): RT=2.32 min, $(M+H)^+$ 360.

The following compounds were similarly prepared:

4a-(4-Fluoro-benzyl)-1-(4-fluoro-phenyl)-4,4a,5,6,7,8-hexahydro-1H-1,2-diaza-6-azonia-cyclopenta[b]naphthalene

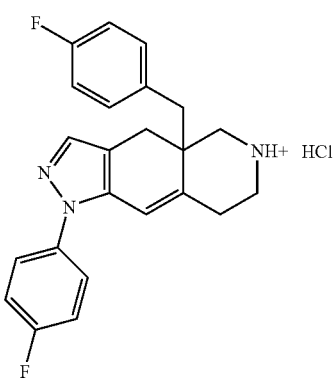

LC-MS (Method A): RT=2.37 min. $(M+H)^+$ 378.

Example 57

6-(4-tert-Butyl-benzenesulfonyl)-4a-(4-fluoro-benzyl)-1-(4-fluoro-phenyl)-4,4a,5,6,7,8-hexahydro-1H-1-2,6-triaza-cyclopenta[b]naphthalene (44A: $R^5$=4-F-Phenyl; $L^1$=$CH_2$; $R^1$=4-F-Phenyl; $L^2$-$R^2$=$SO_2$(4-t-butylphenyl))

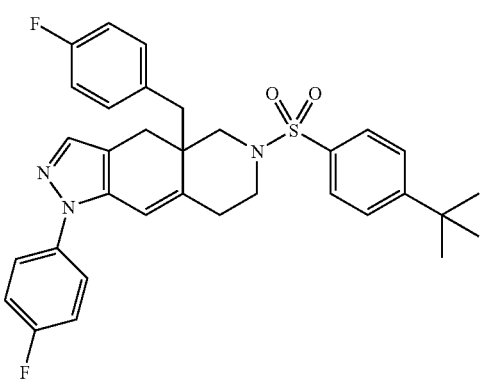

Compound 65A ($R^5$=4-F-phenyl; $L^1$-$R^1$=4-F-benzyl) (100 mg, 0.24 mmol) was dissolved in $CH_2Cl_2$ (5 mL) and diisopropylethylamine (134 µL, 0.97 mmol) and 4-tert-butylphenylsulfonyl chloride (56 mg, 0.24 mmol) were added and the contents were stirred for 18 h. Water (10 mL) was added and the organics were extracted with EtOAc (15 mL), washed with brine and dried ($MgSO_4$). Purification by flash chromatography ($CH_2Cl_2$ 100% to 5% EtOAc in $CH_2Cl_2$) afforded 89 mg of the title compound as a cream solid. LC-MS (Method A): RT=4.82 min, $(M+H)^+$ 574

The following compounds were similarly prepared: .

121

6-Benzenesulfonyl-4a-(4-fluoro-benzyl)-1-(4-fluoro-phenyl)-4,4a,5,6,7,8-hexahydro-1H-1,2,6-triaza-cyclopenta[b]naphthalene

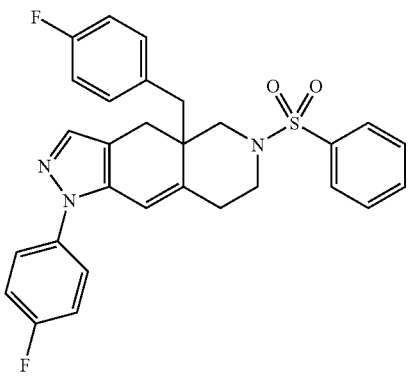

LC-MS (Method A): RT=4.31 min, (M+H)$^+$ 518.

4a-(4-Fluoro-benzyl)-1-(4-fluoro-phenyl)-6-(toluene-4-sulfonyl)-4,4a,5,6,7,8-hexahydro-1H-1,2,6-triaza-cyclopenta[b]naphthalene

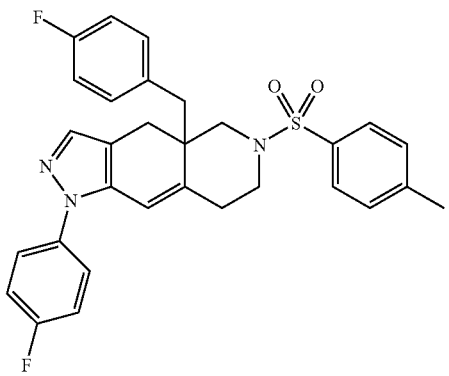

LC-MS (Method A): RT=4.47 min, (M+H)$^+$ 532.

6-(4-Fluoro-benzenesulfonyl)-4a-(4-fluoro-benzyl)-1-(4-fluoro-phenyl)-4,4a,5,6,7,8-hexahydro-1H-1,2,6-triaza-cyclopenta[b]naphthalene

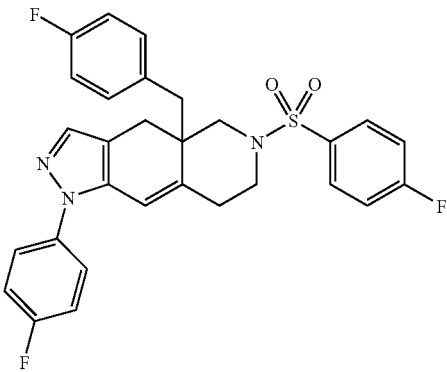

LC-MS (Method A): RT=4.34 min, (M+H)$^+$ 536.

122

4a-(4-Fluoro-benzyl)-1-(4-fluoro-phenyl)-6-methanesulfonyl-4,4a,5,6,7,8-hexahydro-1H-1,2,6-triaza-cyclopenta[b]naphthalene

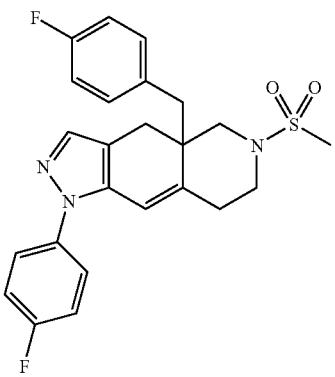

LC-MS (Method A): RT=3.78 min, (M+H)$^+$ 456.

6-(Butane-1-sulfonyl)-4a-(4-fluoro-benzyl)-1-(4-fluoro-phenyl)-4,4a,5,6,7,8-hexahydro-1H-1,2,6-triaza-cyclopenta[b]naphthalene

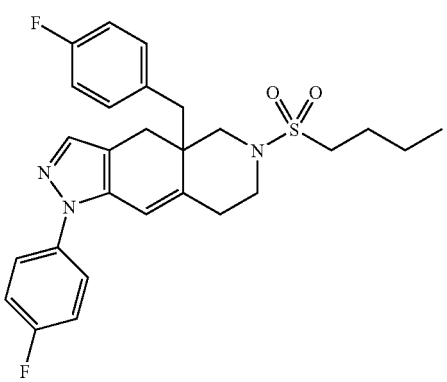

LC-MS (Method A): RT=4.26 min, (M+H)$^+$ 498.

4a-Benzyl-1-(4-fluoro-phenyl)-6-(propane-2-sulfonyl)-4,4a,5,6,7,8-hexahydro-1H-1,2,6-triaza-cyclopenta[b]naphthalene

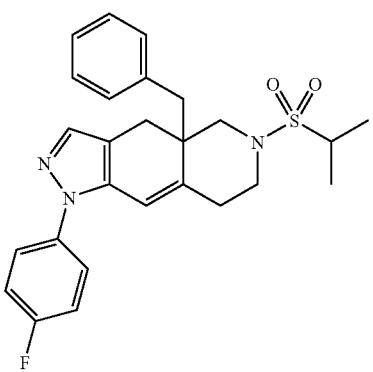

LC-MS (Method A): RT=4.01 min, (M+H)$^+$ 466.

123

4a-(4-Fluoro-benzyl)-1-(4-fluoro-phenyl)-6-(1-methyl-1H-imidazole-4-sulfonyl)-4,4a,5,6,7,8-hexahydro-1H-1,2,6-triaza-cyclopenta[b]naphthalene

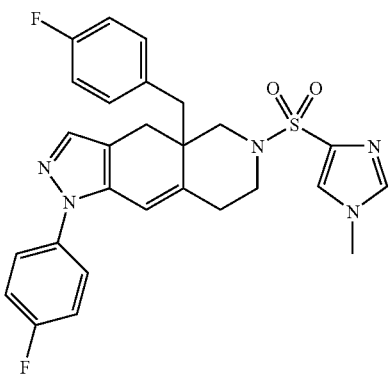

LC-MS (Method A): RT=3.59 min, (M+H)+ 522.

4a-(4-Fluoro-benzyl)-1-(4-fluoro-phenyl)-6-(4-methyl-3,4-dihydro-2H-benzo[1,4]oxazine-7-sulfonyl)-4,4a,5,6,7,8-hexahydro-1H-1,2,6-triaza-cyclopenta[b]naphthalene

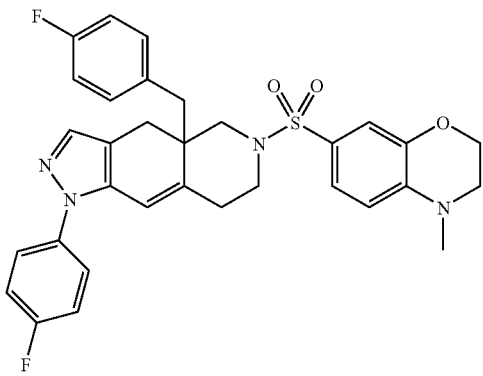

LC-MS (Method A): RT=4.38 min, (M+H)+ 589.

6-(6-tert-Butyl-pyridine-3-sulfonyl)-4a-(4-fluoro-benzyl)-1-(4-fluoro-phenyl)-4,4a,5,6,7,8-hexahydro-1H-1,2,6-triaza-cyclopenta[b]naphthalene

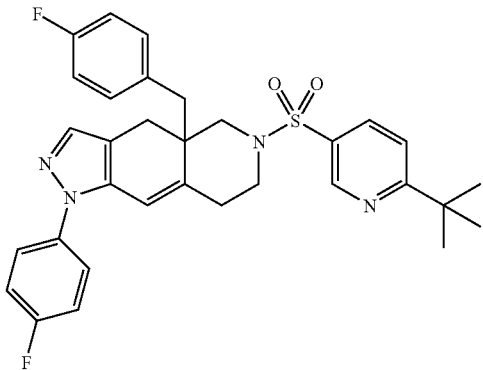

LC-MS (Method A): RT=4.64 min, (M+H)+ 575.

124

4a-(4-Fluoro-benzyl)-1-(4-fluoro-phenyl)-6-(4-morpholin-4-yl-benzenesulfonyl)-4,4a,5,6,7,8-hexahydro-1H-1,2,6-triaza-cyclopenta[b]naphthalene

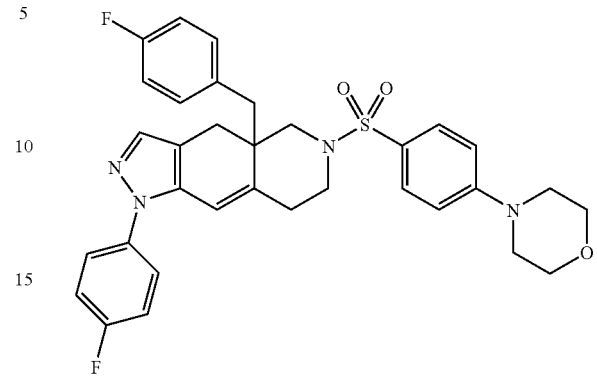

LC-MS (Method A): RT=4.21 min, (M+H)+ 603.

Example 58

4a-(4-Fluoro-benzyl)-1-(4-fluoro-phenyl)-6-pyridin-4-ylmethyl-4,4a,5,6,7,8-hexahydro-1H-1,2,6-triaza-cyclopenta[b]naphthalene (44A: $R^5$=4-F-Phenyl; $L^1$-$R^1$=4-F-benzyl; $L^2$-$R^2$=4-Pyridinylmethyl)

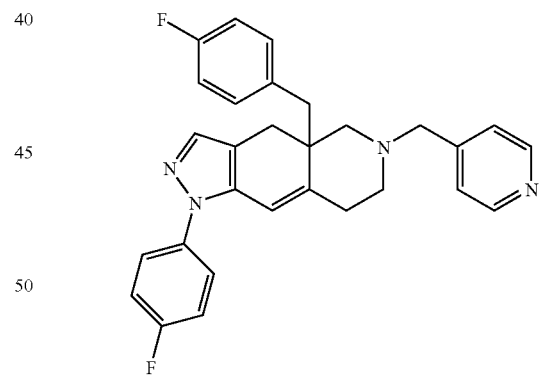

To a solution of compound 65A ($R^5$=4-F-Phenyl; $L^1$-$R^1$=4-F-benzyl) (50 mg, 0.12 mmol) in CH$_2$Cl$_2$ (1 mL) was added 4-pyridinecarboxaldehyde (12 μL, 0.12 mmol) and sodium triacetoxyborohydride (39 mg, 0.18 mmol). The contents were stirred for 18 h at ambient temperature, NaHCO$_3$ (2 mL) was added, and the organics were extracted with CH$_2$Cl$_2$ (10 mL) and washed with brine and dried (MgSO$_4$). Purification by flash chromatography (CH$_2$Cl$_2$ 100% to 25% EtOAc in CH$_2$Cl$_2$) afforded 29 mg of the title compound as an off-white solid. LC-MS (Method A): RT=2.71 min, (M+H)+ 469.

The following compounds were similarly prepared:

125

4a-(4-Fluoro-benzyl)-1-(4-fluoro-phenyl)-6-pyridin-3-ylmethyl-4,4a,5,6,7,8-hexahydro-1H-1,2,6-triaza-cyclopenta[b]naphthalene

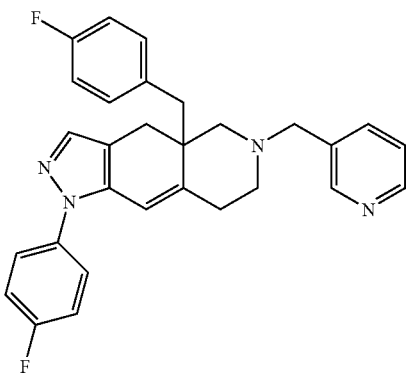

LC-MS (Method A): RT=2.54 min, (M+H)+ 469.

4a-(4-Fluoro-benzyl)-1-(4-fluoro-phenyl)-6-pyridin-2-ylmethyl-4,4a,5,6,7,8-hexahydro-1H-1,2,6-triaza-cyclopenta[b]naphthalene

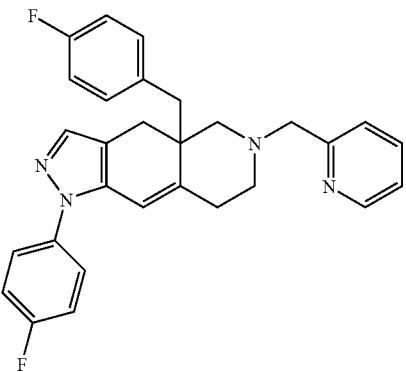

LC-MS (Method A): RT=2.55 min, (M+H)+ 469.

6-(6-tert-Butyl-pyridin-3-ylmethyl)-4a-(4-fluoro-benzyl)-1-(4-fluoro-phenyl)-4,4a,5,6,7,8-hexahydro-1H-1,2,6-triaza-cyclopenta[b]naphthalene

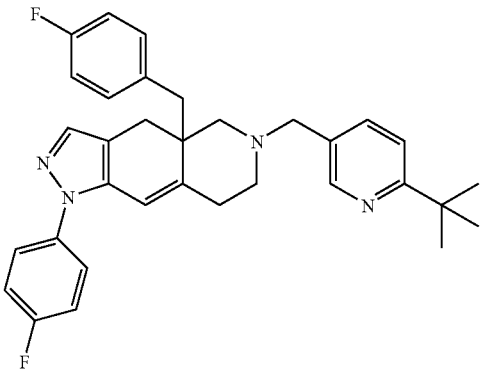

LC-MS (Method A): RT=3.07 min, (M+H)+ 525.

126

4a-(4-Fluoro-benzyl)-1-(4-fluoro-phenyl)-6-propyl-4,4a,5,6,7,8-hexahydro-1H-1,2,6-triaza-cyclopenta[b]naphthalene

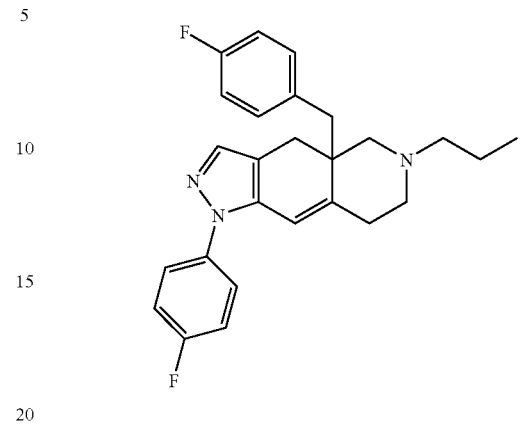

LC-MS (Method A): RT=2.44 min, (M+H)+ 420.

4a-Benzyl-1-(4-fluoro-phenyl)-6-(1H-imidazol-4-ylmethyl)-4,4a,5,6,7,8-hexahydro-1H-1,2,6-triaza-cyclopenta[b]naphthalene

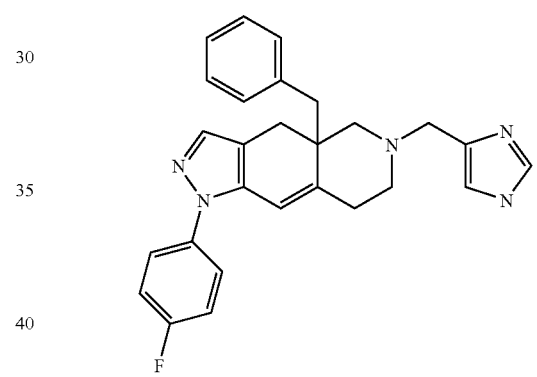

LC-MS (Method A): RT=2.18 min, (M+H)+ 440.

4a-Benzyl-1-(4-fluoro-phenyl)-6-pyridin-4-ylmethyl-4,4a,5,6,7,8-hexahydro-1H-1,2,6-triaza-cyclopenta[b]naphthalene

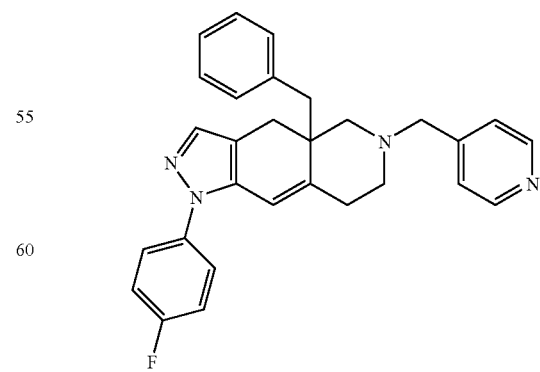

LC-MS (Method A): RT=2.65 min, (M+H)+ 451.

Example 59

4a-(4-Fluoro-benzyl)-1-(4-fluoro-phenyl)-6-phenyl-4,4a,5,6,7,8-hexahydro-1H-1,2,6-triaza-cyclopenta[b]naphthalene (44A: $R^5$=4-F-Phenyl; $L^1$-$R^1$=4-F-benzyl; $L^2$-$R^2$=Phenyl)

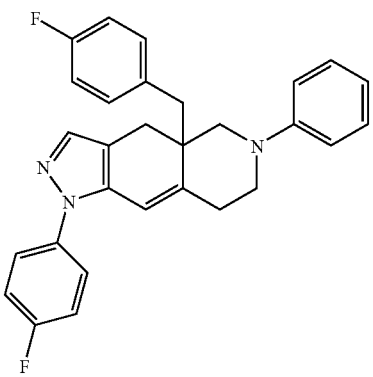

To a solution of compound 65A ($R^5$=4-F-phenyl; $L^1$-$R^1$=4-F-benzyl) (70 mg, 0.17 mmol) in $CH_2Cl_2$ (2.5 mL) was added copper$^{II}$ acetate (61 mg, 0.34 mmol) and phenyl boronic acid (41 mg, 0.34 mmol) and the contents were stirred at ambient temperature for 48 h. Water (2 mL) was added and the organics were extracted with $CH_2Cl_2$ (10 mL) and washed with brine and dried ($MgSO_4$). Purification by flash chromatography ($CH_2Cl_2$ 100% to 25% EtOAc in $CH_2Cl_2$) afforded 15 mg of the title compound as an off-white solid. LC-MS (Method A): RT=4.84 min, (M+H)$^+$ 454.

Example 60

4a-(4-Fluoro-benzyl)-1-(4-fluoro-phenyl)-1,4,4a,5,7,8-hexahydro-1,2,6-triaza-cyclopenta[b]naphthalene-6-carboxylic acid phenylamide (44A: $R^5$=4-F-Phenyl; $L^1$-$R^1$=4-F-benzyl; $L^2$-$R^2$=CONHPhenyl)

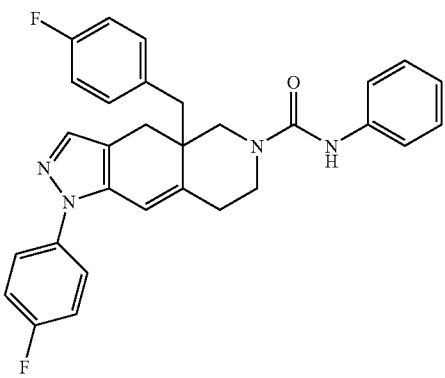

Compound 65A ($R^5$=4-F-phenyl; $L^1$-$R^1$=4-F-benzyl) (50 mg, 0.12 mmol) was dissolved in $CH_2Cl_2$ (2 mL) and triethylamine (18 μL, 0.13 mmol) and phenyl isocyanate (14 μL, 0.13 mmol) were added and the contents stirred for 18 h. Water (5 mL) was added and the organics were extracted with EtOAc (5 mL) and washed with brine and dried ($MgSO_4$). Purification by flash chromatography ($CH_2Cl_2$ 100% to 5% EtOAc in $CH_2Cl_2$) afforded 10 mg of the title compound as a cream solid. LC-MS (Method A): RT=3.96 min, (M+H)$^+$ 497.

Example 61

4a-(4-Fluoro-benzyl)-1-(4-fluoro-phenyl)-1,4,4a,5,7,8-hexahydro-1,2,6-triaza-cyclopenta[b]naphthalene-6-sulfonic acid phenylamide (44A: $R^5$=4-F-Phenyl; $L^1$-$R^1$=4-F-Phenyl; $L^2$-$R^2$=$SO_2$NHPhenyl)

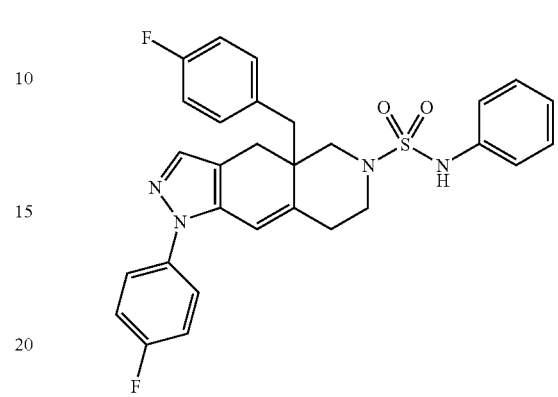

Compound 65A ($R^5$=4-F-Phenyl; $L^1$-$R^1$=4-F-benzyl) (25 mg, 0.06 mmol) was dissolved in $CH_2Cl_2$ (2 mL) and triethylamine (101 μL, 0.73 mmol) and phenyl sulfamoyl chloride (65 mg, 0.34 mmol) were added and the contents were stirred for 18 h. Water (5 mL) was added and the organics were extracted with EtOAc (5 mL) and washed with brine and dried ($MgSO_4$). Purification by flash chromatography ($CH_2Cl_2$ 100% to 5% EtOAc in $CH_2Cl_2$) afforded 15 mg of the title compound as a cream solid. LC-MS (Method A): RT=4.14 min, (M+H)$^+$ 533.

The following compounds were similarly prepared:

4a-(4-Fluoro-benzyl)-1-(4-fluoro-phenyl)-6-(morpholine-4-sulfonyl)-4,4a,5,6,7,8-hexahydro-1H-1,2,6-triaza-cyclopenta[b]naphthalene

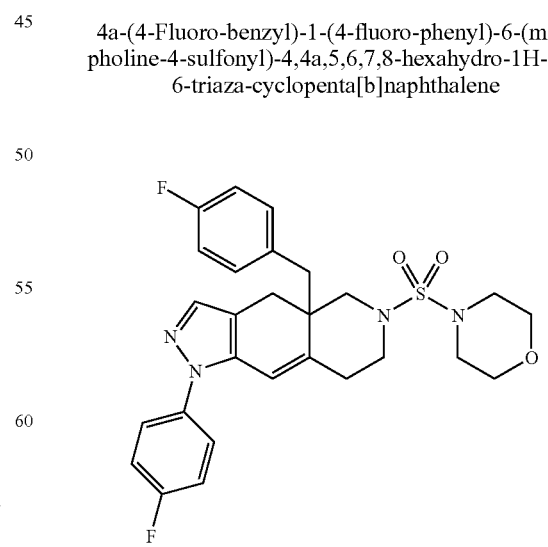

LC-MS (Method A): RT=3.90 min, (M+H)$^+$ 527.

4a-(4-Fluoro-benzyl)-1-(4-fluoro-phenyl)-6-(4-methyl-piperazine-1-sulfonyl)-4,4a,5,6,7,8-hexahydro-1H-1,2,6-triaza-cyclopenta[b]naphthalene

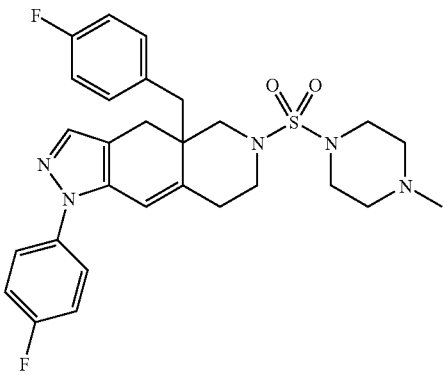

LC-MS (Method A): RT=2.63 min, (M+H)$^+$ 540.

4a-(4-Fluoro-benzyl)-1-(4-fluoro-phenyl)-6-(piperidine-1-sulfonyl)-4,4a,5,6,7,8-hexahydro-1H-1,2,6-triaza-cyclopenta[b]naphthalene:F

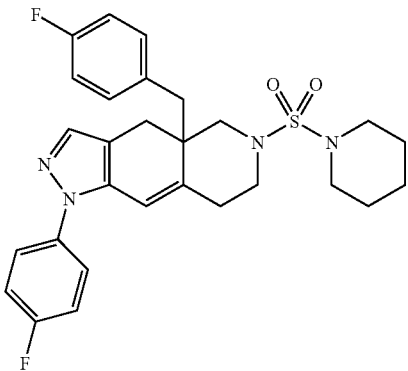

LC-MS (Method A): RT=4.36 min, (M+H)$^+$ 525.

Example 62

2-[4a-Benzyl-1-(4-fluoro-phenyl)-1,4,4a,5,7,8-hexahydro-1,2,6-triaza-cyclopenta[b]naphthalen-6-yl]-N,N-dimethyl-acetamide (44A: (44A: R$^5$=4-F-Phenyl; L$^1$-R$^1$=Benzyl; L$^2$-R$^2$=CH$_2$CONMe$_2$)

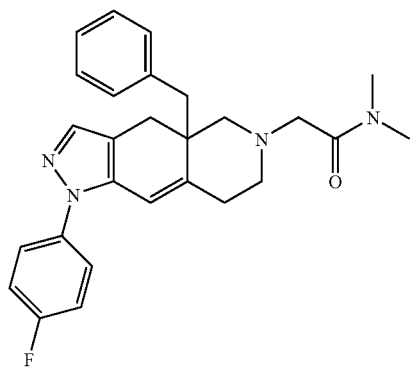

Compound 65A (R$^5$=4-F-phenyl; L$^1$-R$^1$=benzyl) (42 mg, 0.11 mmol) was dissolved in CH$_2$Cl$_2$ (2 mL) and sodium hydride (5 mg, 0.13 mmol) and 2-chloro-N,N-dimethylacetamide (13 µL, 0.13 mmol) were added and the contents were stirred for 18 h. Water (5 mL) was added and the organics were extracted with EtOAc (5 mL) and washed with brine and dried (MgSO$_4$). Purification by flash chromatography (CH$_2$Cl$_2$ 100% to 10% EtOAc in CH$_2$Cl$_2$) afforded 9 mg of the title compound as a yellow oil LC-MS (Method A): RT=2.34 min, (M+H)$^+$ 445.

Example 63

Glucocorticoid Receptor Binding Assay

The following is a description of an assay for determining the inhibition of dexamethasone binding of the Human Recombinant Glucocorticoid Receptor:

Binding protocol: Compounds were tested in a binding displacement assay using human recombinant glucocorticoid receptor with $^3$H-dexamethasone as the ligand. The source of the receptor was recombinant baculovirus-infected insect cells. This GR was a full-length steroid hormone receptor likely to be associated with heat-shock and other endogenous proteins.

The assay was carried out in v-bottomed 96-well polypropylene plates in a final volume of 200 µl containing 0.5 nM GR solution, 2.5 nM 3H-dexamethasone (Amersham TRK 645) in presence of test compounds, test compound vehicle (for total binding) or excess dexamethasone (20 µM, to determine non-specific binding) in an appropriate volume of assay buffer.

For the Primary Screen, test compounds were tested at 1 µM in duplicate. These compounds were diluted from 10 mM stock in 100% DMSO. After dilution to 100 µM, 5 µl were added to 245 µl assay buffer to obtained 2 µM compound and 2% DMSO.

For the IC$_{50}$ determinations, test compounds were tested at 6 concentrations in duplicate (concentration range depends on % inhibition binding that was obtained in the Primary Screen). Test compounds were diluted from 10 mM stock in 100% DMSO. The tested solutions were prepared at 2× final assay concentration in 2% DMSO/assay buffer.

All reagents and the assay plate were kept on ice during the addition of reagents. The reagents were added to wells of a v-bottomed polypropylene plate in the following order: 50 µl of 10 nM 3H-dexamethasone solution, 100 µl of TB/NSB/compound solution and 50 µl of 2 nM GR solution. After the additions, the incubation mixture was mixed and incubated for 2.5 hrs at 4° C.

After 2.5 hrs incubation, unbound counts were removed with dextran coated charcoal (DCC) as follows: 25 µl of DCC solution (10% DCC in assay buffer) was added to all wells and mixed (total volume 225 µl). The plate was centrifuged at 400 rpm for 10 minutes at 4° C. 75 µl of the supernatants (i.e. ⅓ of total volume) was carefully pipetted into an optiplate. 200 µl of scintillation cocktail were added (Microscint-40, Packard Bioscience. B.V.). The plate was vigorously shaken for approx. 10 minutes and counted on Topcount.

For the IC$_{50}$ determinations, the results were calculated as % inhibition [$^3$H]-dexamethasone bound and fitted to sigmoidal curves (fixed to 100 and 0) to obtain IC$_{50}$ values (concentration of compound that displaces 50% of the bound counts). The IC$_{50}$ values were converted to K$_i$ (the inhibition constant) using the Cheng-Prusoff equation. Test results are presented in Table I for selected compounds of the Invention. Compounds with a K$_i$ value of <10 nM are designated with ***; compounds with a K$_i$ value of 10-100 nM are designated with

**; compounds with a K$_i$ of >100 nM are designated with *.
A—indicates that the compound was not tested.

Reagents: Assay buffer: 10 mM potassium phosphate buffer pH 7.6 containing 5 mM DTT, 10 mM sodium molybdate, 100 µM EDTA and 0.1% BSA.

TABLE I

| Structure | GR Binding | GR Functional |
|---|---|---|
| | *** | ** |
| | *** | * |
| | *** | * |
| | *** | * |
| | *** | ** |

TABLE I-continued

| Structure | GR Binding | GR Functional |
|---|---|---|
| | *** | *** |
| | *** | ** |
| | *** | * |
| | *** | * |
| | ** | — |

TABLE I-continued

| | GR Binding | GR Functional |
|---|---|---|
| (structure) | *** | ** |
| (structure) | ** | * |
| (structure) | * | * |
| (structure) | ** | * |

TABLE I-continued

| | GR Binding | GR Functional |
|---|---|---|
| (structure) | *** | * |
| (structure) | *** | * |
| (structure) | *** | ** |
| (structure) | *** | * |
| (structure) | *** | * |

TABLE I-continued

| | GR Binding | GR Functional |
|---|---|---|
| (structure) | *** | * |
| (structure) | *** | ** |
| (structure) | *** | *** |
| (structure) | *** | ** |
| (structure) | *** | * |
| (structure) | *** | * |
| (structure) | ** | — |
| (structure) | *** | ** |
| (structure) | ** | * |
| (structure) | * | * |

TABLE I-continued
| | GR Binding | GR Functional |
|---|---|---|
| 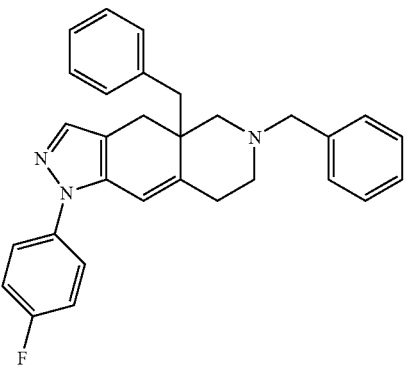 | ** | * |
| 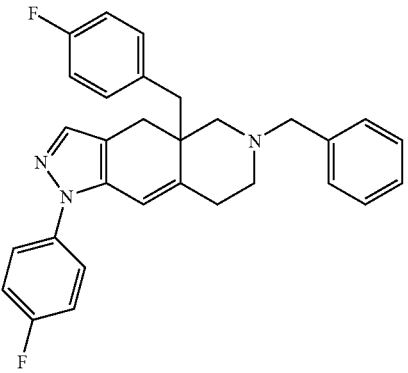 | *** | * |
| 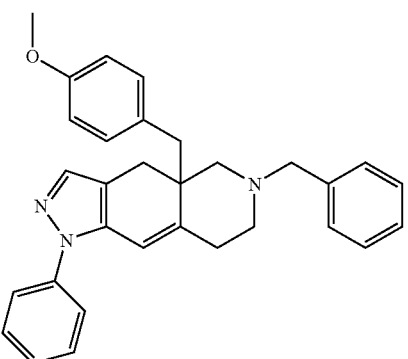 | *** | * |
| 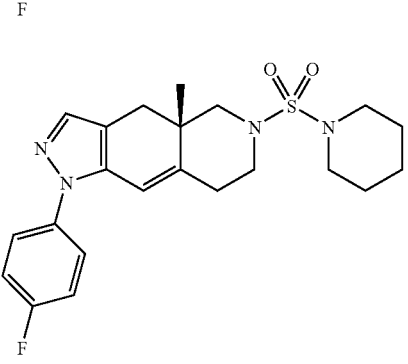 | ** | * |
TABLE I-continued
| | GR Binding | GR Functional |
|---|---|---|
| 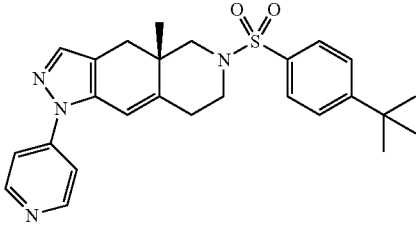 | *** | * |
| 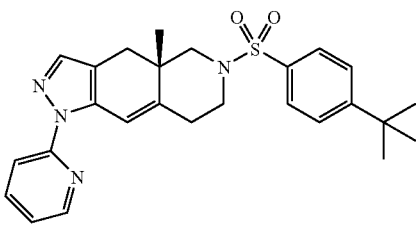 | ** | — |
| 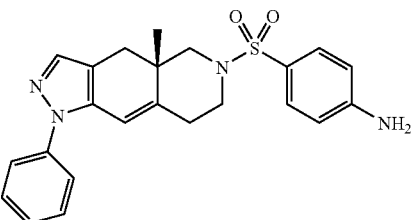 | ** | * |
| 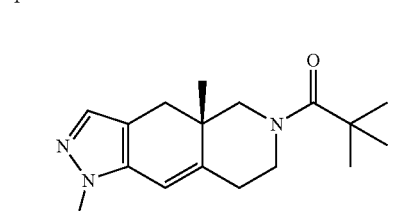 | * | * |
| 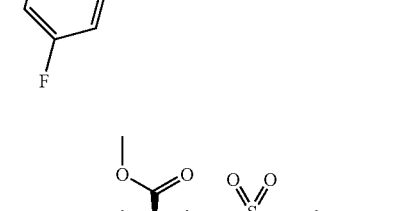 | * |  |

TABLE I-continued
| | GR Binding | GR Functional |
|---|---|---|
| 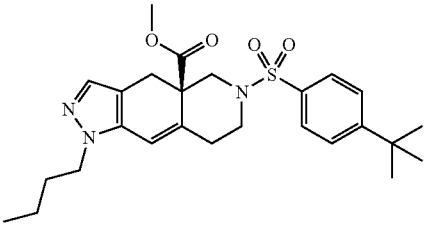 | ** | * |
| 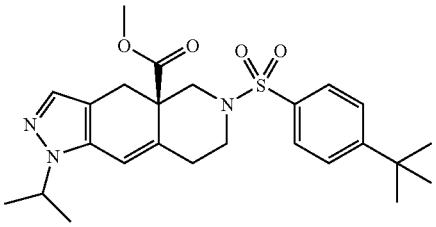 | ** | * |
| 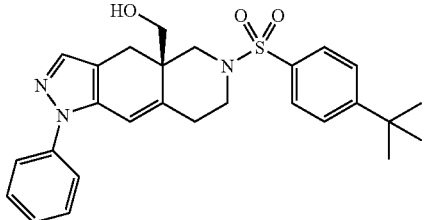 | * |  |
| 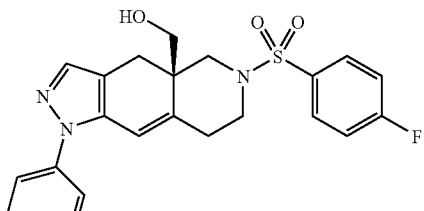 | *** | * |
| 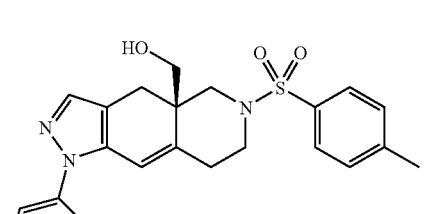 | * |  |
TABLE I-continued
| | GR Binding | GR Functional |
|---|---|---|
| 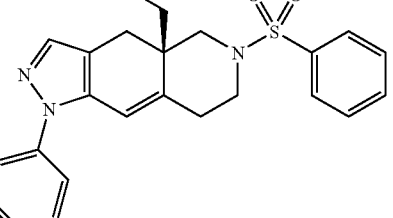 | ** | — |
| 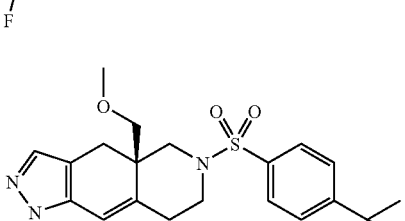 | * | * |
|  | * | * |
| 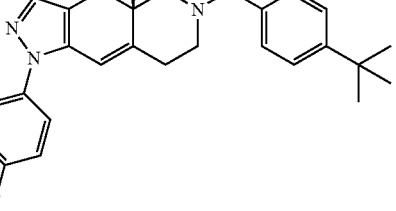 | * |  |

TABLE I-continued
| | GR Binding | GR Functional |
|---|---|---|
| 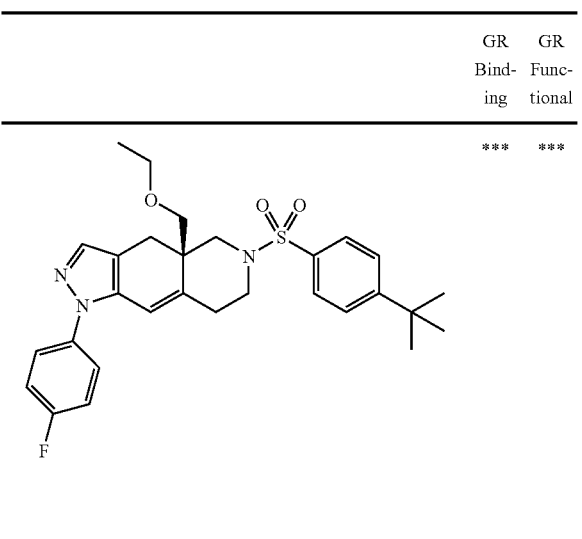 | * | * |
| 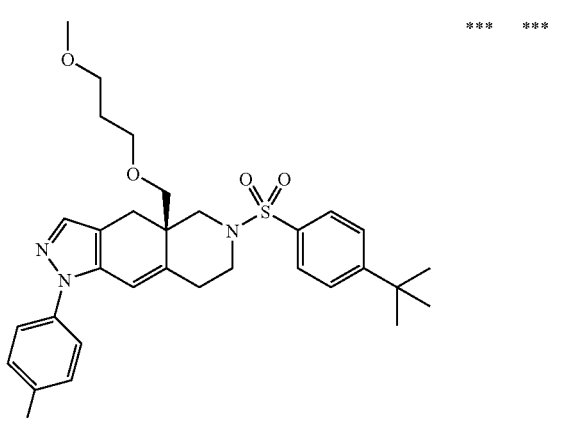 | * | * |
| 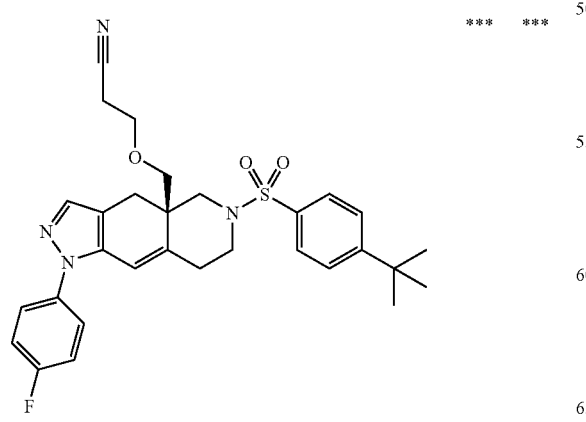 | * | * |
TABLE I-continued
| | GR Binding | GR Functional |
|---|---|---|
| 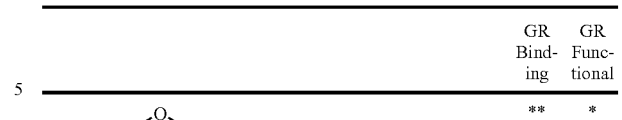 | ** | * |
| 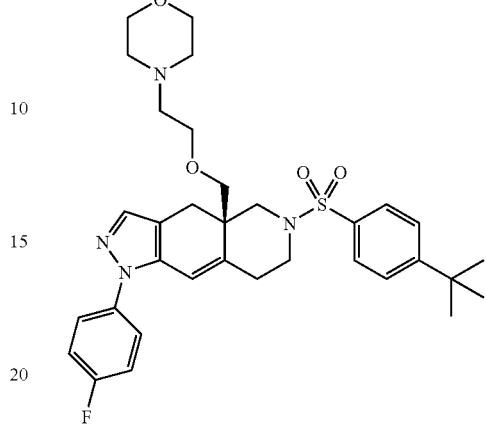 | * | * |
| 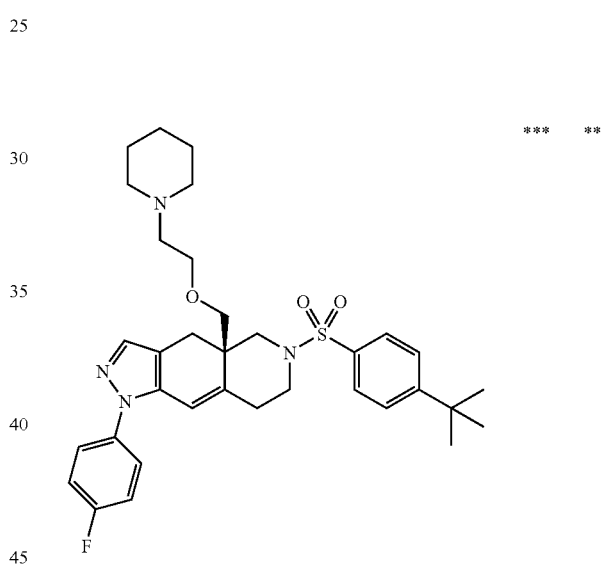 | * |  |
| 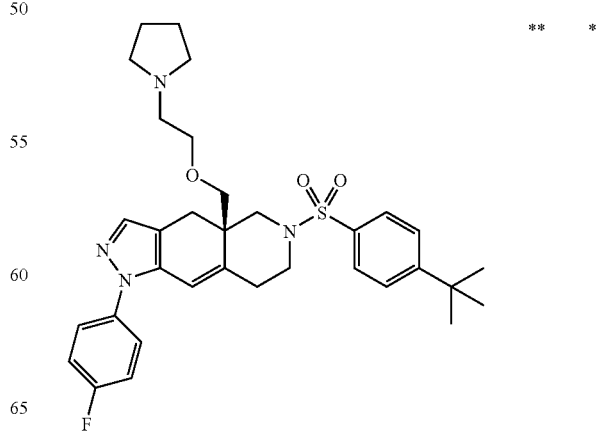 | ** | * |

TABLE I-continued
| | GR Binding | GR Functional |
|---|---|---|
| 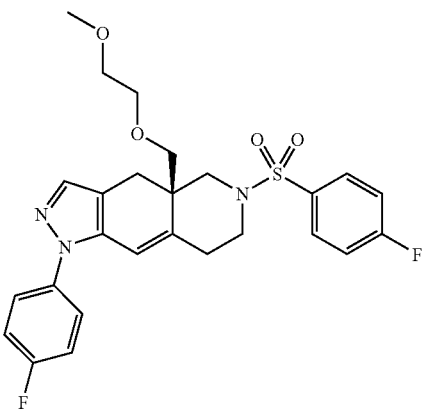 | * | * |
| 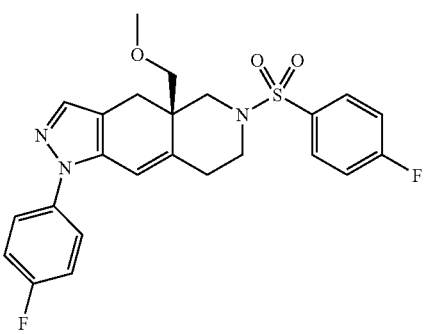 | * |  |
| 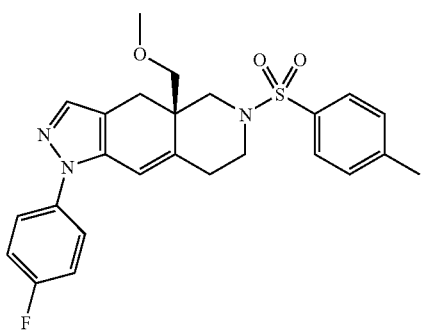 | * | * |
| 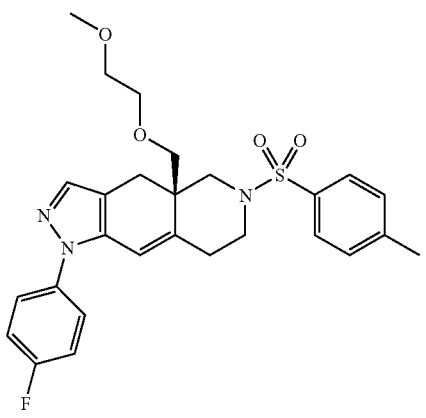 | * | * |
TABLE I-continued
| | GR Binding | GR Functional |
|---|---|---|
| 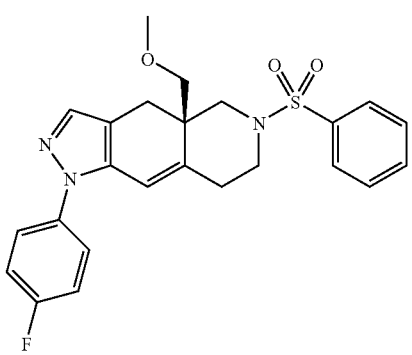 | * | * |
| (second structure) | * |  |
| 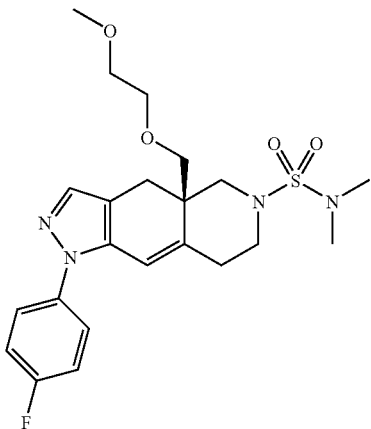 | * | * |
| 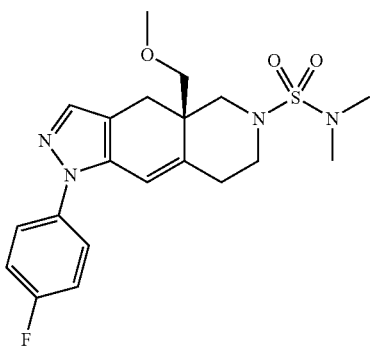 | ** | * |

TABLE I-continued
| | GR Binding | GR Functional |
|---|---|---|
| 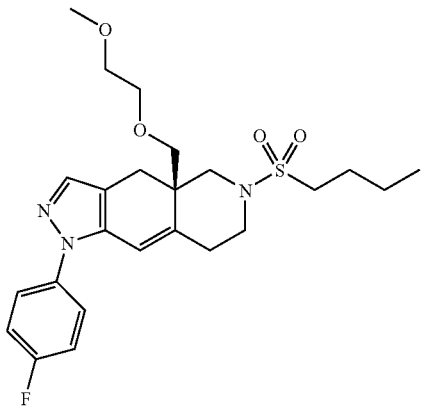 | * |  |
| 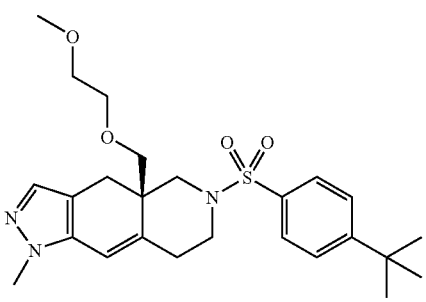 | ** | * |
| 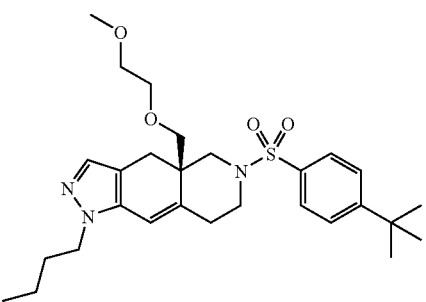 | * |  |
| 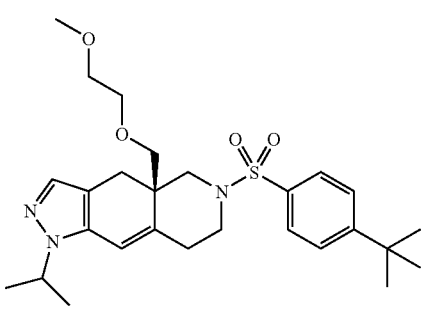 | * |  |
| 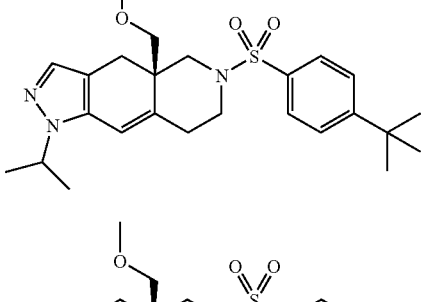 | ** | * |
TABLE I-continued
| | GR Binding | GR Functional |
|---|---|---|
| 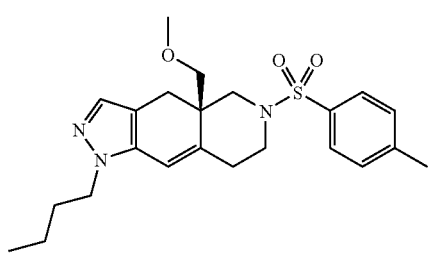 | ** | * |
| 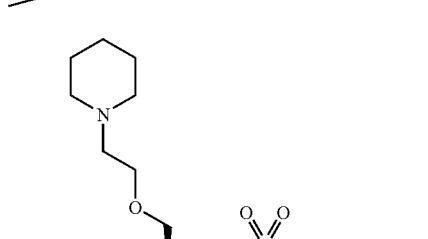 | * |  |
| 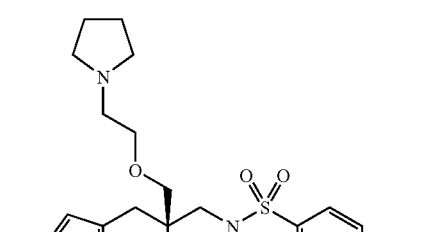 | ** | * |
| 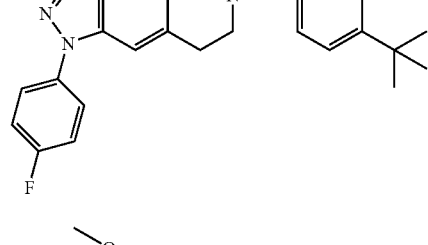 | * | * |

TABLE I-continued
| | GR Binding | GR Functional |
|---|---|---|
| 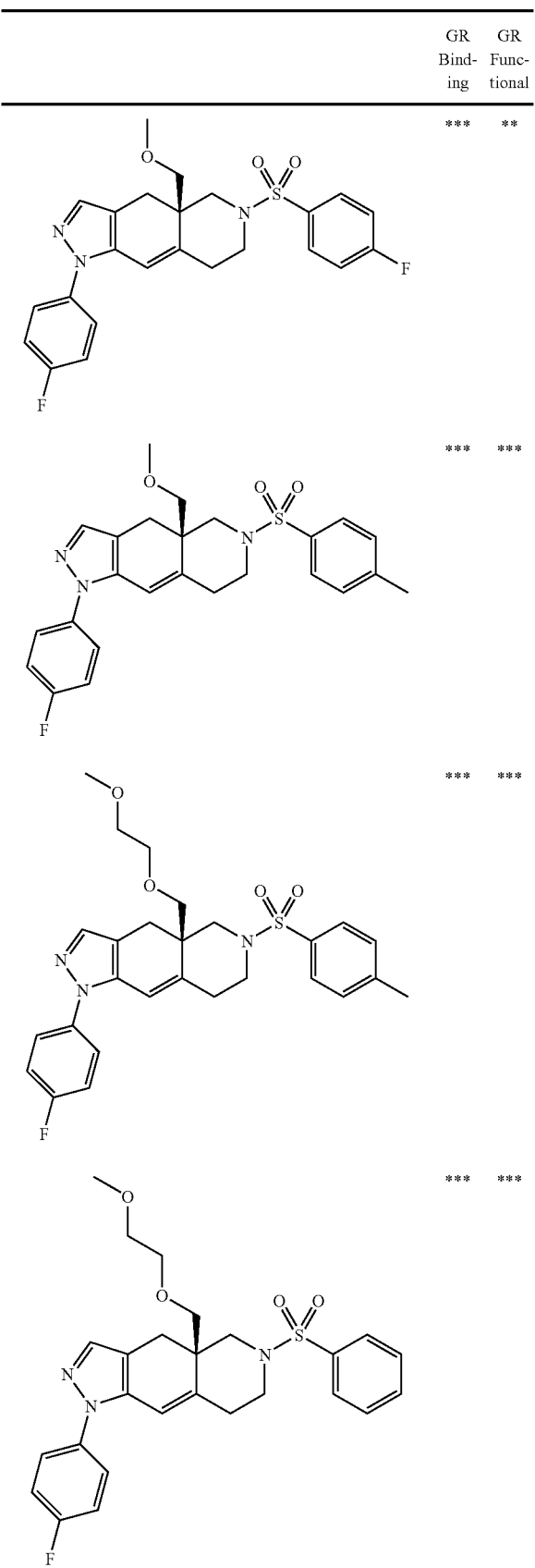 | * |  |
| | * | * |
| | *** | *** |
| | *** | *** |
TABLE I-continued
| | GR Binding | GR Functional |
|---|---|---|
| 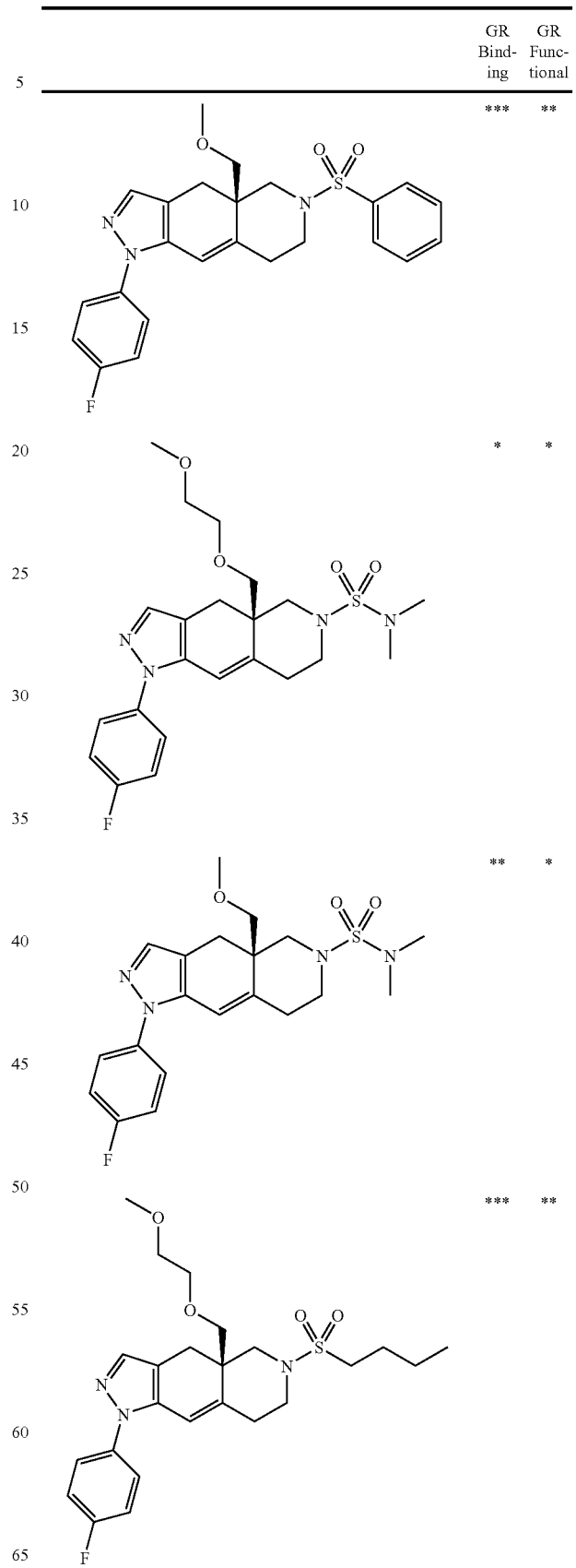 | * |  |
| | * | * |
| | ** | * |
| | *** | ** |

TABLE I-continued
| | GR Binding | GR Functional |
|---|---|---|
| 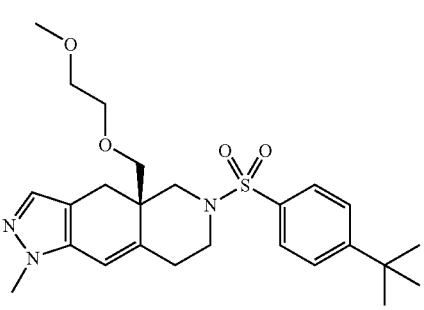 | ** | * |
| 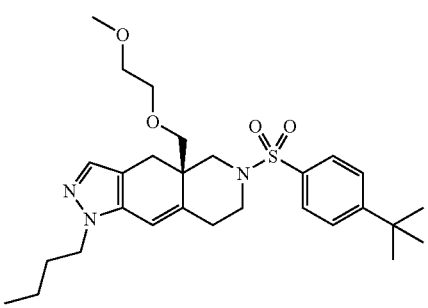 | * |  |
| 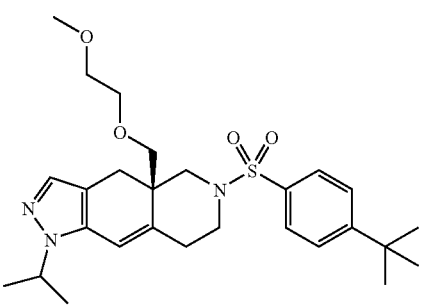 | * |  |
| 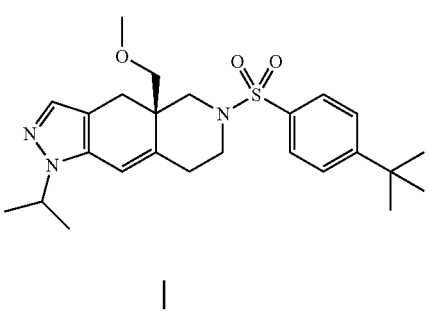 | ** | * |
| 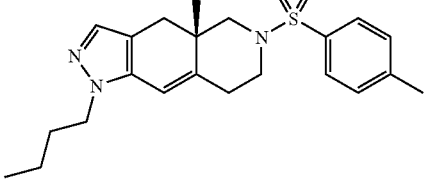 | ** | * |
TABLE I-continued
| | GR Binding | GR Functional |
|---|---|---|
| 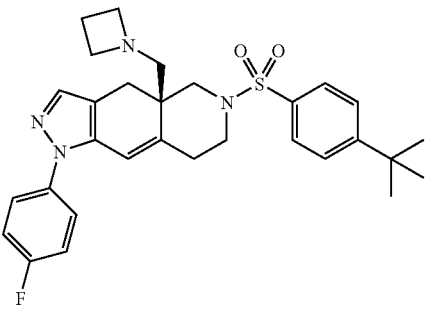 | * |  |
| 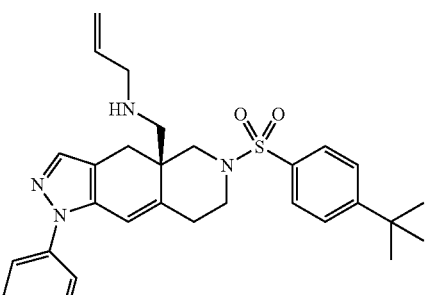 | * |  |
| 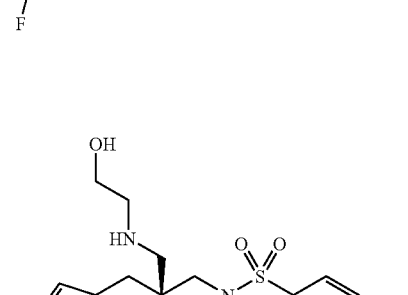 | * |  |
| 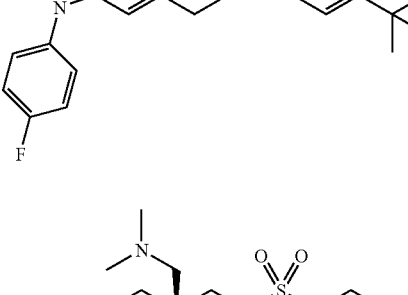 | * |  |

TABLE I-continued
| | GR Binding | GR Functional |
|---|---|---|
| 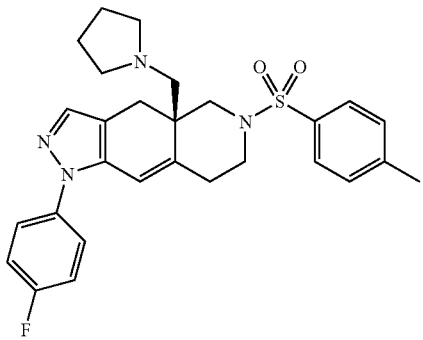 | * | * |
| 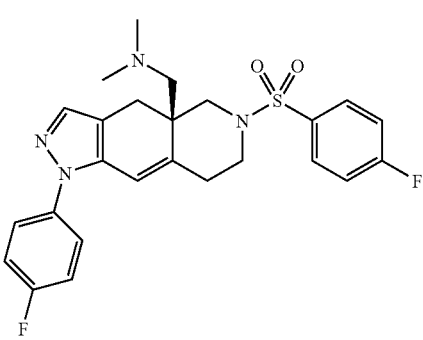 | * |  |
| 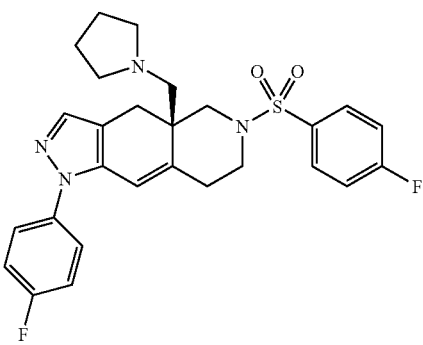 | * | * |
| 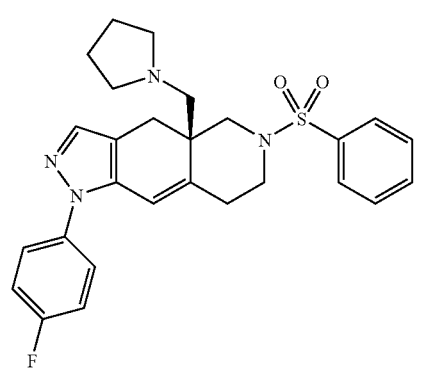 | * | * |
TABLE I-continued
| | GR Binding | GR Functional |
|---|---|---|
| 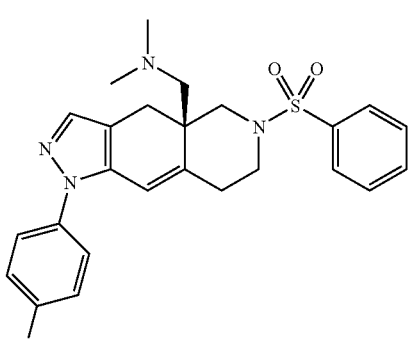 | * |  |
| 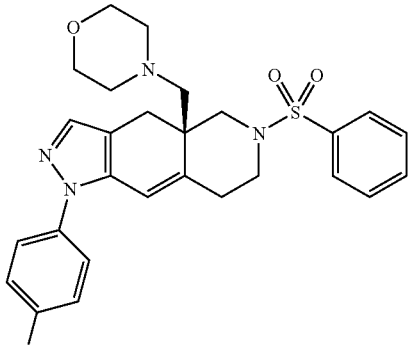 | * |  |
| 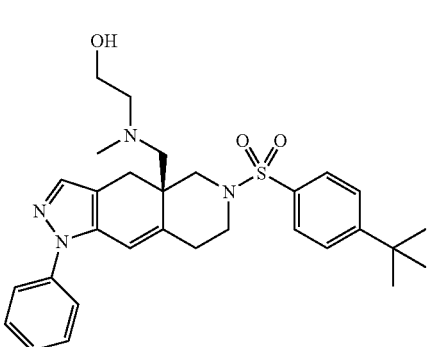 | * | * |
| 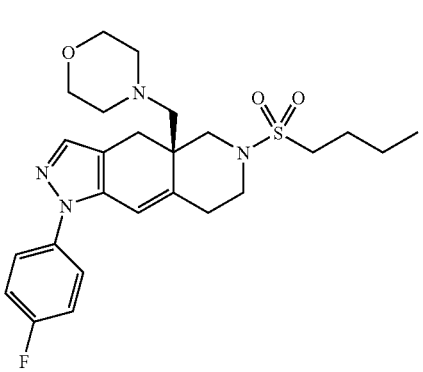 | ** | * |

TABLE I-continued
| | GR Binding | GR Functional |
|---|---|---|
| 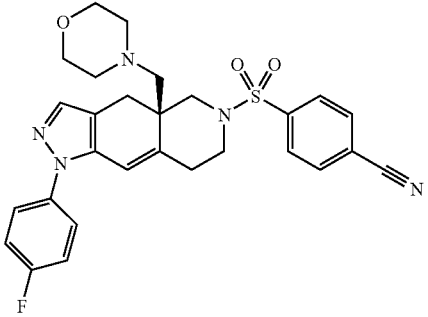 | *** | * |
| 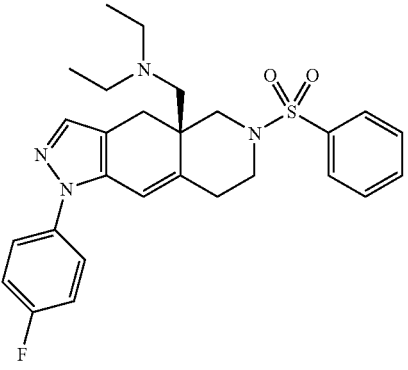 | * |  |
| 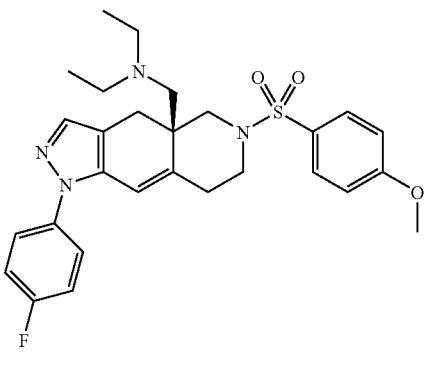 | * |  |
| 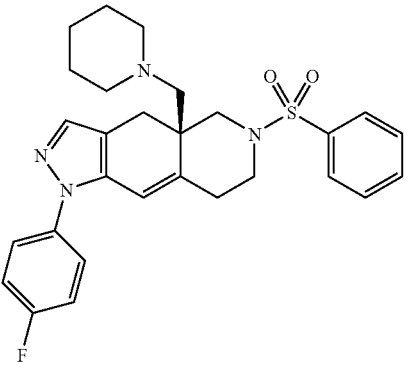 | * |  |
TABLE I-continued
| | GR Binding | GR Functional |
|---|---|---|
| 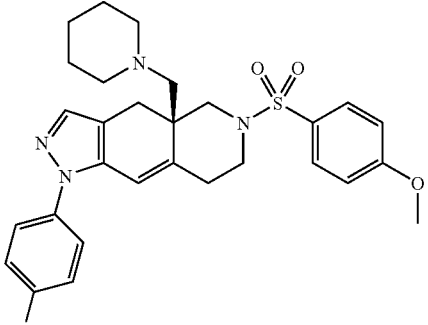 |  |  |
| 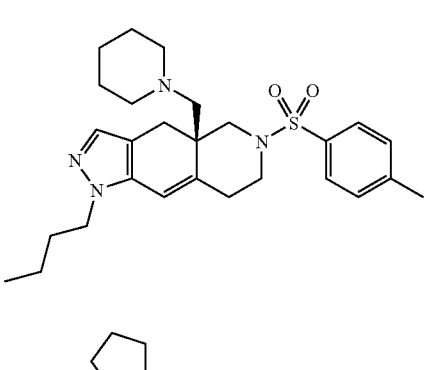 | ** | — |
| 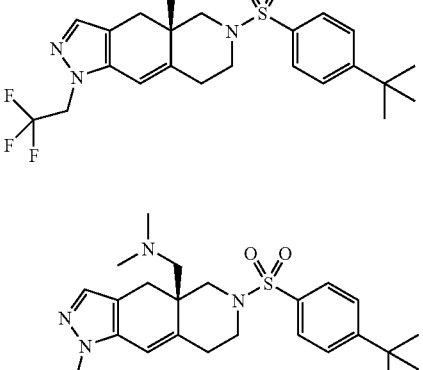 | ** | * |
| 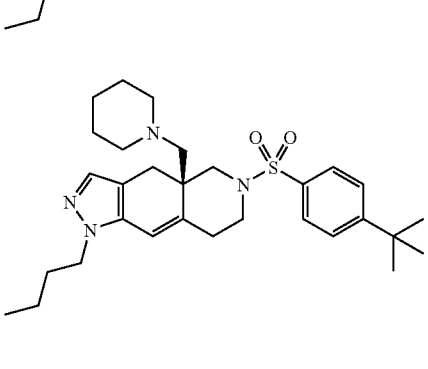 | ** | * |
| 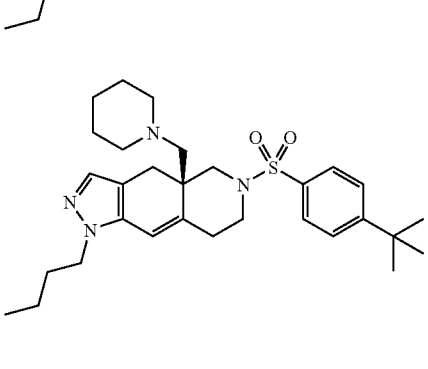 | * |  |

TABLE I-continued
| | GR Binding | GR Functional |
|---|---|---|
| 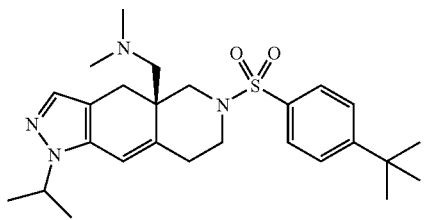 | ** | * |
| 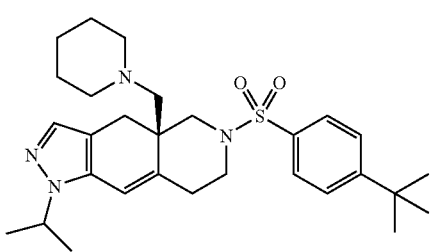 | * | * |
| 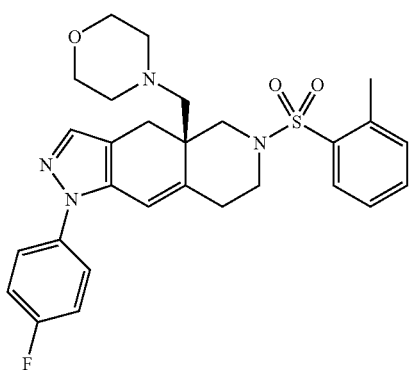 | * |  |
| 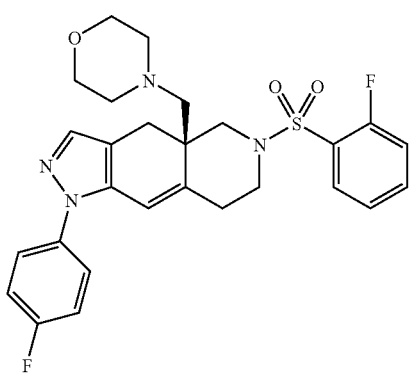 | * |  |
TABLE I-continued
| | GR Binding | GR Functional |
|---|---|---|
| 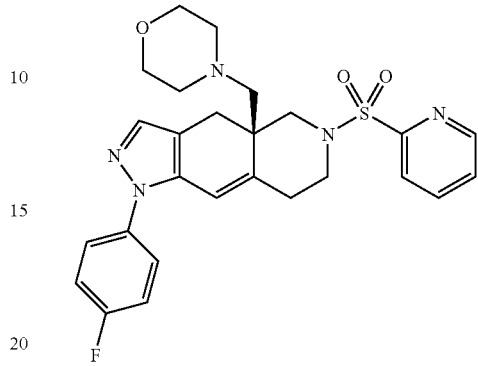 | *** | — |
| 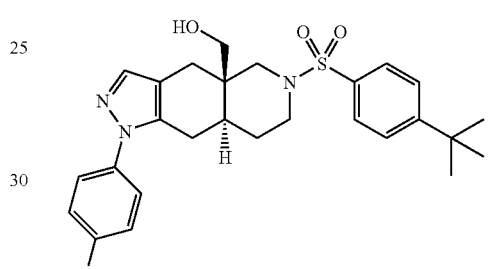 | * | * |
| 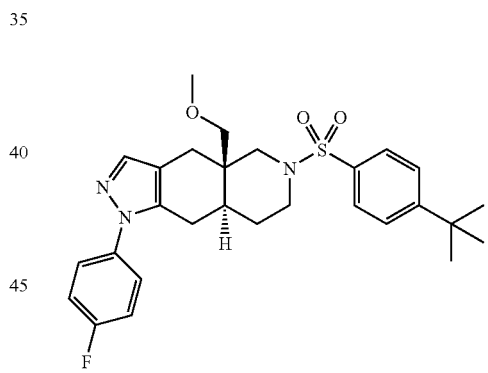 | *** | * |
| 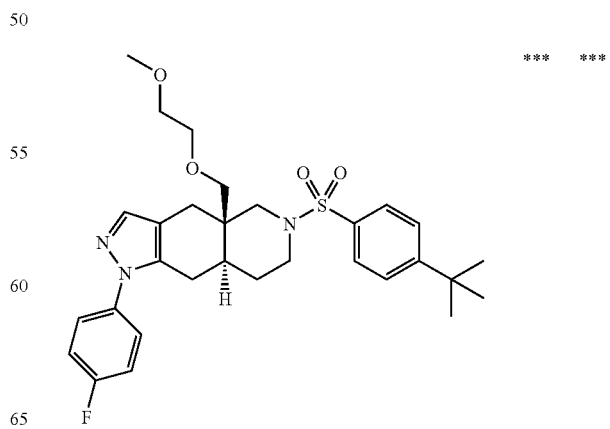 | * | * |

TABLE I-continued

| Structure | GR Binding | GR Functional |
|---|---|---|
| (4-fluorophenyl-pyrazole fused bicyclic with CH2-O-CH2CH2-OCH3 and phenylsulfonyl, H stereochem) | *** | ** |
| (4-fluorophenyl-pyrazole fused bicyclic with CH2-OCH3 and phenylsulfonyl, H stereochem) | ** | * |
| (4-fluorophenyl-pyrazole fused bicyclic with benzyl-NH-C(O)- and 4-tert-butylphenylsulfonyl) | ** | * |
| (4-fluorophenyl-pyrazole fused bicyclic with morpholinomethyl and 4-tert-butylphenylsulfonyl) | ** | * |
| (4-fluorophenyl-pyrazole fused bicyclic with piperidinyl-C(O)- and 4-tert-butylphenylsulfonyl) | *** | * |
| (4-fluorophenyl-pyrazole fused bicyclic with pyrrolidinyl-C(O)- and 4-tert-butylphenylsulfonyl) | *** | ** |
| (4-fluorophenyl-pyrazole fused bicyclic with ethyl-NH-C(O)- and 4-tert-butylphenylsulfonyl) | *** | * |
| (4-fluorophenyl-pyrazole fused bicyclic with N,N-dimethyl-C(O)- and 4-tert-butylphenylsulfonyl) | ** | * |
| (4-fluorophenyl-pyrazole fused bicyclic with CH(OH)CH3 and 4-tert-butylphenylsulfonyl) | *** | ** |

TABLE I-continued
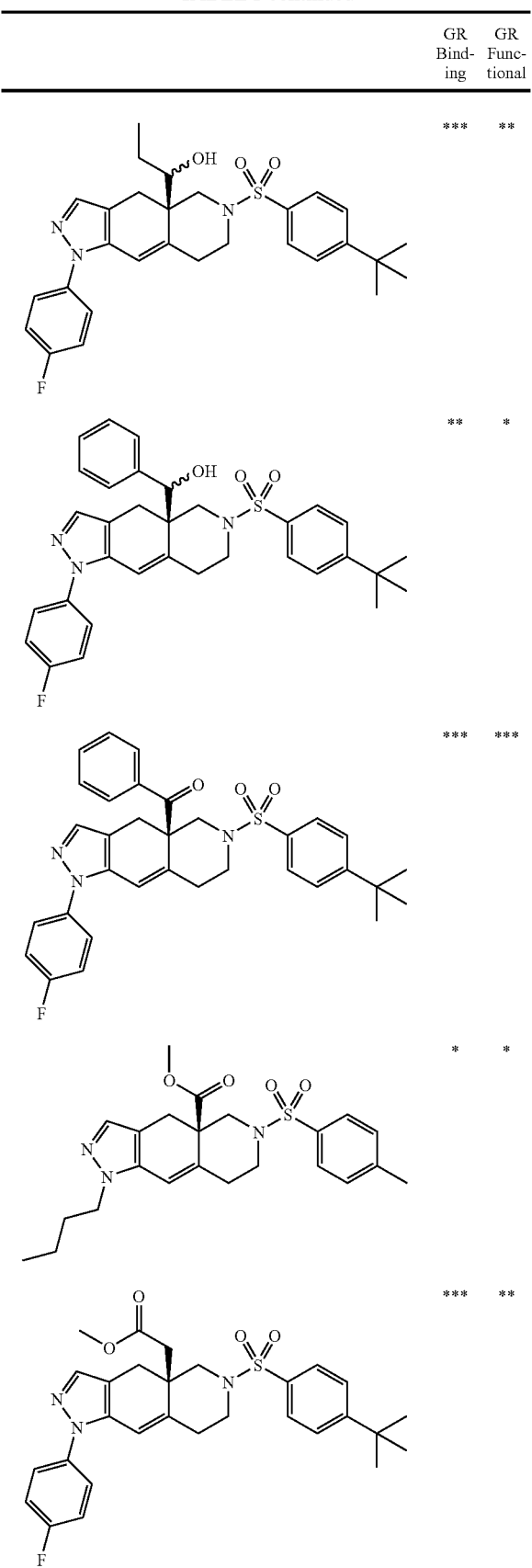
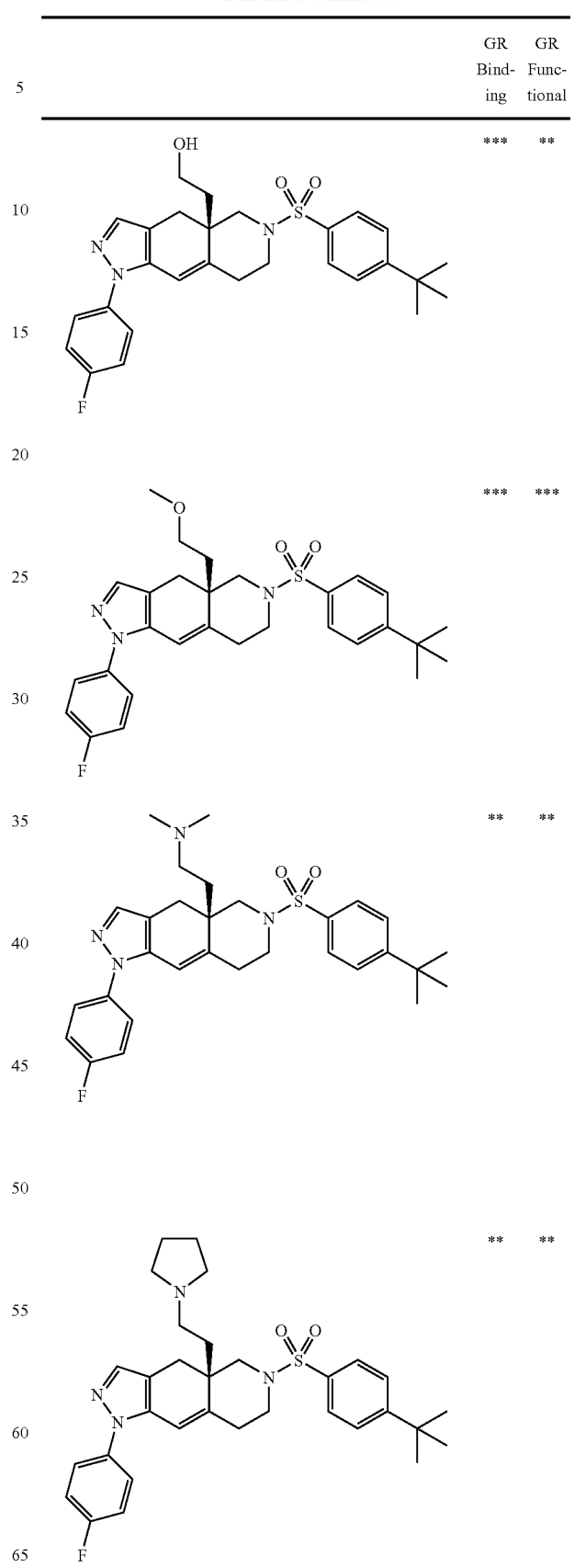

TABLE I-continued
| | GR Binding | GR Functional |
|---|---|---|
| 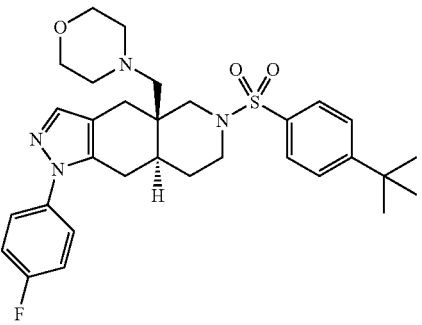 | * |  |
| 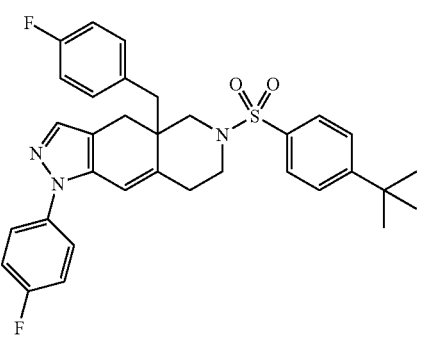 | * |  |
| 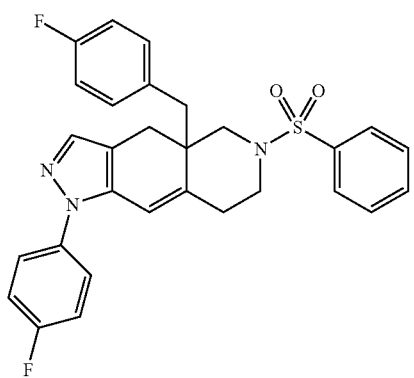 | * |  |
| 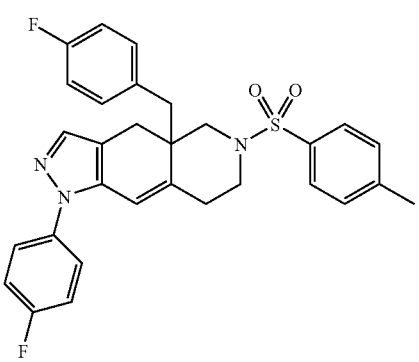 | * |  |
TABLE I-continued
| | GR Binding | GR Functional |
|---|---|---|
| 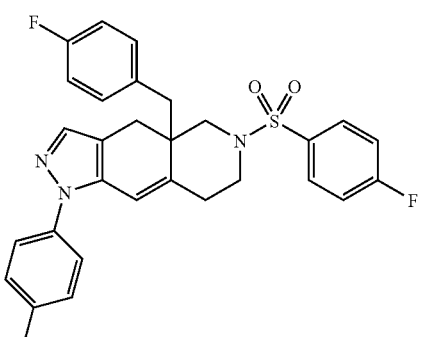 | * |  |
| 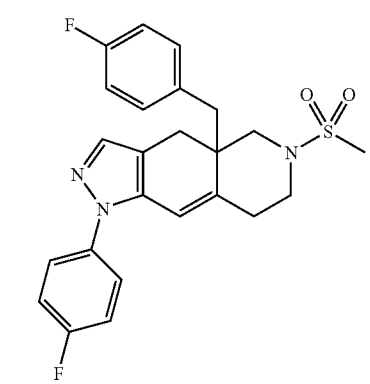 | ** | * |
| 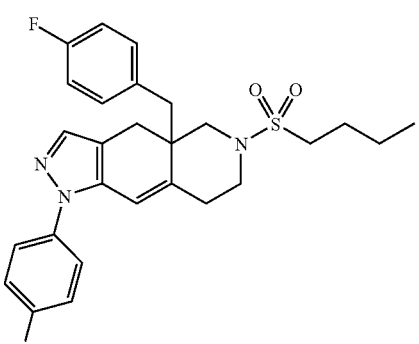 | ** | * |
| 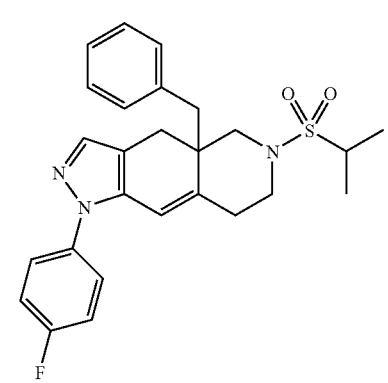 | * | * |

TABLE I-continued
| | GR Binding | GR Functional |
|---|---|---|
| 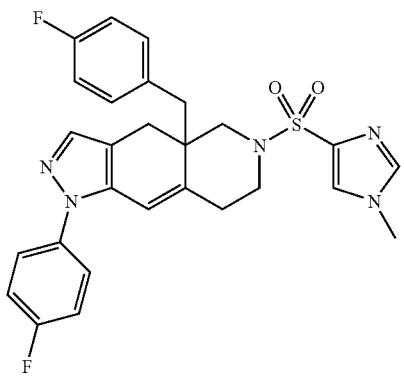 | *** | * |
| 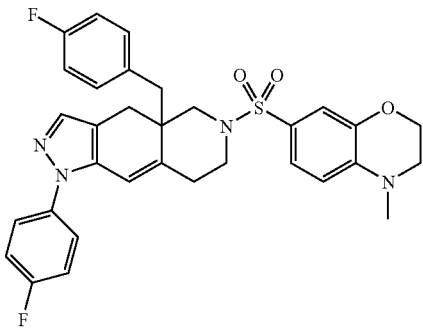 | * | * |
| 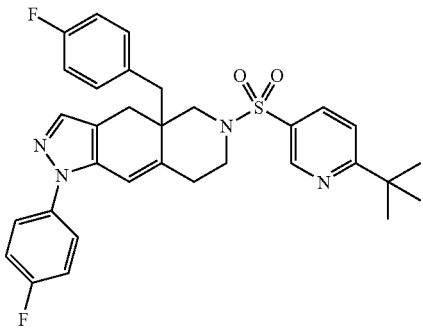 | *** | * |
| 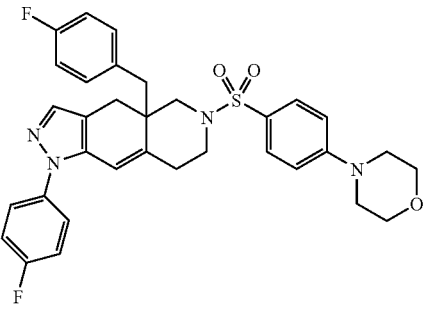 | * |  |
TABLE I-continued
| | GR Binding | GR Functional |
|---|---|---|
| 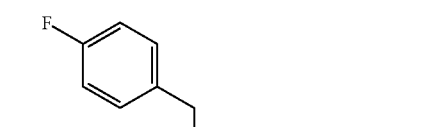 | ** | * |
| 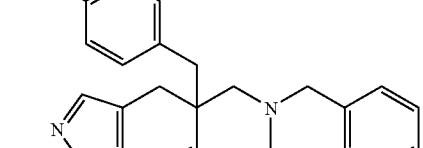 | ** | * |
| 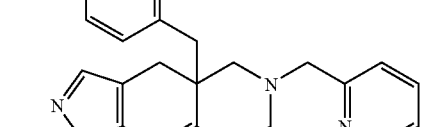 | *** | * |
|  | *** | * |

TABLE I-continued

| | GR Binding | GR Functional |
|---|---|---|
| (structure) | ** | * |
| (structure) | * | * |
| (structure) | ** | * |
| (structure) | ** | * |

TABLE I-continued

| | GR Binding | GR Functional |
|---|---|---|
| (structure) | *** | ** |
| (structure) | ** | * |
| (structure) | ** | * |
| (structure) | ** | * |

TABLE I-continued

| | GR Binding | GR Functional |
|---|---|---|
| (structure: 4-fluorobenzyl indazole tetrahydroisoquinoline with sulfonyl piperidine, N-(4-fluorophenyl)) | ** | * |
| (structure: benzyl indazole tetrahydroisoquinoline with dimethylaminoacetamide, N-(4-fluorophenyl)) | * | * |
| (structure: OMe-ethoxymethyl indazole tetrahydroisoquinoline with tosyl sulfonamide, N-cyclopentyl) | *** | ** |

Example 64

Selectivity Binding Assays

Selectivity binding assays were performed against human estrogen (ERα), progesterone (PR), androgen (AR) and mineralocorticoid (MR) receptors. The selectivity assays were carried out in the same assay buffer and volumes as the GR binding assay and DCC was used to separate free from bound label.

Mineralocorticoid binding assay: MR was obtained from Sf9 cells infected with recombinant baculovirus containing MR, and the MR was isolated according to the method of Binart et al (Binart, N.; Lombes, M.; Rafestin-Oblin, M. E.; Baulieu, E. E. Characterisation of human mineralocorticoid receptor expressed in the baculovirus system. *PNAS US*, 1991, 88, 10681-10685). Compounds were tested against an appropriate dilution of the MR (determined for each batch of receptor) with 2.4 nM of [$^3$H] aldosterone (Perkin Elmer NET419) and incubated for 60 mins at room temperature.

Estrogen binding assay: Compounds were tested for displacement of 0.56 nM [$^3$H]-estradiol (Perkin Elmer NET517) binding to 0.5 nM ERα (obtained from Pan Vera 26467A) following an incubation period of 90 mins at room temperature.

Progesterone binding assay: Compounds were tested for displacement of 3 nM [$^3$H]-progesterone (Perkin Elmer NET381) binding to 1 nM PR (obtained from Pan Vera 24900). This assay was incubated for 120 mins at 4° C.

Androgen binding assay: Compounds were tested, in triplicate, for displacement of 6 nM [$^3$H]-dihydrotestosterone (Perkin Elmer NET453) binding to 3 nM PR (obtained from Pan Vera 24938). This assay was incubated overnight at 4° C.

Compounds in Table I inhibited <50% binding at the MR, ER, PR, and AR receptors under the above protocols when tested at 10 μM.

Example 65

GR Functional Assay Using SW1353/MMTV-5 Cells

SW1353/MMTV-5 is an adherent human chondrosarcoma cell line that contains endogenous glucocorticoid receptors. It was transfected with a plasmid (pMAMneo-Luc) encoding firefly luciferase located behind a glucocorticoid-responsive element (GRE) derived from a viral promoter (long terminal repeat of mouse mammary tumor virus). A stable cell line SW1353/MMTV-5 was selected with geneticin, which was required to maintain this plasmid. This cell line was thus sensitive to glucocorticoids (dexamethasone) leading to expression of luciferase ($EC_{50}^{dex}$ 10 nM). This dexamethasone-induced response was gradually lost over time, and a new culture from an earlier passage was started (from a cryo-stored aliquot) every three months.

In order to test for a GR-antagonist, SW1353/MMTV-5 cells were incubated with several dilutions of the compounds in the presence of $5 \times EC_{50}^{dex}$ (50 nM), and the inhibition of induced luciferase expression was measured using a luminescence in a Topcounter (LucLite kit from Perkin Elmer). For each assay, a dose-response curve for dexamethasone was prepared in order to determine the $EC_{50}^{dex}$ required for calculating the $K_i$ from the $IC_{50}$'s of each tested compound. Test results are presented in Table I for selected compounds of the Invention. Compounds with a $K_i$ value of <10 nM are designated with *; compounds with a $K_i$ value of 10-100 nM are designated with ; compounds with a $K_i$ of >100 nM are designated with *. A—indicates that the compound was not tested.

SW1353/MMTV-5 cells were distributed in 96-well plates and incubated in medium (without geneticin) for 24 hrs (in the absence of $CO_2$). Dilutions of the compounds in medium+50 nM dexamethasone were added and the plates further incubated for another 24 hrs after which the luciferase expression is measured.

Example 66

Cytotoxicity Assay Using SW1353/Luc-4 Cells

In order to exclude the possibility that compounds inhibit the dexamethasone-induced luciferase response (GR-antagonist) due to their cytotoxicity or due to their direct inhibition of luciferase, a SW1353 cell line was developed that constitutively expressed firefly luciferase, by transfection with plasmid pcDNA3.1-Luc and selection with geneticin. The cell line SW1353/Luc-4 was isolated that constitutively expressed luciferase.

SW1353/Luc-4 cells were distributed in 96-well plates and incubated (no $CO_2$) for 24 hrs, after which compound dilutions (without dexamethasone) were added. After a further 24 hrs incubation, luciferase expression was measured using the "LucLite" assay. The compounds listed in Table I did not demonstrate cytotoxicity in this assay when tested at a concentration of 1-3 micromolar.

Example 67

MR and PR Functional Assays Using T47D/MMTV-5 Cells

T47D/MMTV-5 is an adherent human breast carcinoma cell line containing endogenous mineralocorticoid-(MR) and progesterone (PR) receptors. As for the SW1353 cell line, T47D cells was transfected with the same pMAMneo-Luc plasmid, and stable lines selected with geneticin. A cell line T47D/MMTV-5 was isolated which responded to aldosterone ($EC_{50}^{ald}$ 100 nM), and progesterone ($EC_{50}^{prog}$ 10 nM), leading to expression of luciferase.

As for the GR assay to test for MR- or PR-antagonists, the T47D/MMTV-5 cells were incubated with several dilutions of the compounds in the presence of the $5 \times EC_{50}$ of the agonist aldosterol ($EC_{50}^{ald}$ 100 nM) or progesterone ($EC_{50}^{prog}$ 10 nM), respectively. For each assay, a dose response curve was prepared for both aldosterone and progesterone.

T47D/MMTV-5 cells were distributed in 96-well plates (100 μl) in RPMI1640 medium+10% Charcoal stripped FCS. The cells were incubated for 24 hrs in the $CO_2$-oven. A volume of 100 μl of the compound dilutions in medium+agonist (500 nM aldost; 50 nM progest) were added, and the plates further incubated for another 24 hrs after which the luciferase expression was measured.

Compounds of the Invention did not display MR or PR functional activity in these assays. For example, the compound of Example 29 inhibited only 8% of the PR agonist response and 10% of the MR functional response when tested at a concentration of 3 micromolar.

What is claimed is:

1. A compound having the formula

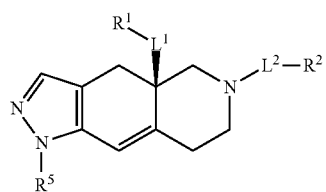

(XI)

wherein
$L^1$ and $L^2$ are members independently selected from a bond and unsubstituted alkylene;
$R^1$ is a member selected from unsubstituted alkyl, unsubstituted heteroalkyl, unsubstituted heterocycloalkyl, —$OR^{1A}$, —$NR^{1C}R^{1D}$, —$C(O)NR^{1C}R^{1D}$, and —$C(O)OR^{1A}$, wherein
$R^{1A}$ is a member selected from hydrogen, unsubstituted alkyl and unsubstituted heteroalkyl,
$R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen;

$R^2$ has the formula:

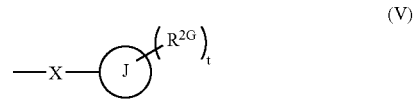

(V)

wherein
$R^{2G}$ is a member selected from hydrogen, halogen, unsubstituted alkyl, unsubstituted heteroalkyl, unsubstituted cycloalkyl, unsubstituted heterocycloalkyl, —CN, and —$CF_3$;
J is phenyl;
t is an integer from 0 to 5;
X is —$S(O_2)$—; and
$R^5$ is phenyl optionally substituted with 1-5 $R^{5A}$ groups, wherein
$R^{5A}$ is a member selected from hydrogen, halogen, —$OR^{5A1}$, —$S(O_2)NR^{5A2}R^{5A3}$, —CN, and unsubstituted alkyl, wherein
$R^{5A1}$ is a member selected from hydrogen and unsubstituted alkyl, and
$R^{5A2}$ and $R^{5A3}$ are members independently selected from hydrogen and unsubstituted alkyl.

2. The compound of claim 1, wherein
$R^{2G}$ is a member selected from hydrogen, unsubstituted ($C_1$-$C_{10}$) alkyl, unsubstituted 2-10 membered heteroalkyl, unsubstituted ($C_3$-$C_7$)cycloalkyl, and unsubstituted 3-7 membered heterocycloalkyl.

3. The compound of claim 1, wherein $R^{2G}$ is a branched or unbranched ($C_1$-$C_{10}$)alkyl.

4. The compound of claim 1, wherein $L^1$ and $L^2$ are members independently selected from a bond and unsubstituted ($C_1$-$C_6$) alkylene.

5. A pharmaceutical composition comprising a pharmaceutically acceptable excipient and the compound of claim 1.

6. The compound of claim 1, having the formula

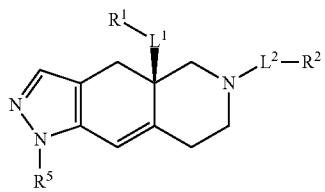

(XI)

wherein,
$L^1$-$R^1$ is a member selected from methyl, —$OR^{1A}$, —$C(O)OR^{1A}$, $CH_2$—$OR^{1A}$, $(CH_2)_2$—$OR^{1A}$, $NR^{1C}R^{1D}$, —$C(O)NR^{1C}R^{1D}$, —$CH_2$—$NR^{1C}R^{1D}$, and —$(CH_2)$—$NR^{1C}R^{1D}$.

7. The compound of claim 6, wherein $L^1$-$R^1$ is a member selected from —$CH_2$—$OR^{1A}$, and —$(CH_2)$—$NR^{1C}R^{1D}$.

8. The compound of claim 1, having the formula

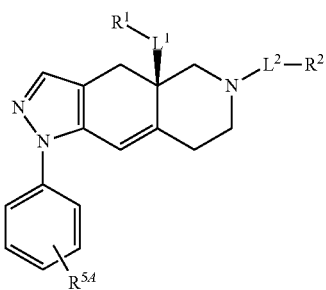

(IX)

wherein,
L¹-R¹ is a member selected from methyl, —OR¹ᴬ, —C(O)OR¹ᴬ, CH₂—OR¹ᴬ, (CH₂)₂—OR¹ᴬ, NR¹ᶜR¹ᴰ, —C(O)NR¹ᶜR¹ᴰ, —CH₂—NR¹ᶜR¹ᴰ, and —(CH₂)—NR¹ᶜR¹ᴰ.

9. The compound of claim 1, having the formula

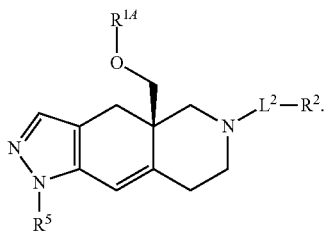

10. The compound of claim 1, selected from the group consisting of:
(S)-6-(4-tert-Butyl-benzenesulfonyl)-1-(4-fluoro-phenyl)-4a-methyl-4,4a,5,6,7,8-hexahydro-1H-1,2,6-triaza-cyclopenta[b]naphthalene;
(S)-6-Benzenesulfonyl-1-(4-fluoro-phenyl)-4a-methyl-4,4a,5,6,7,8-hexahydro-1H-1,2,6-triaza-cyclopenta[b]naphthalene;
(S)-1-(4-Fluoro-phenyl)-4a-methyl-6-(toluene-4-sulfonyl)-4,4a,5,6,7,8-hexahydro-1H-1,2,6-triaza-cyclopenta[b]naphthalene;
(S)-1-(4-Trifluoromethyl-phenyl)-4a-methyl-6-(toluene-4-sulfonyl)-4,4a,5,6,7,8-hexahydro-1H-1,2,6-triaza-cyclopenta[b]naphthalene;
(S)-1-(4-Fluoro-phenyl)-4a-methyl-6-(4-morpholin-4-yl-benzenesulfonyl)-4,4a,5,6,7,8-hexahydro-1H-1,2,6-triaza-cyclopenta[b]naphthalene;
(S)-1-(4-Fluoro-phenyl)-4a-methyl-6-(4-methyl-3,4-dihydro-2H-benzo[1,4]oxazine-7-sulfonyl)-4,4a,5,6,7,8-hexahydro-1H-1,2,6-triaza-cyclopenta[b]naphthalene;
4-[(S)-1-(4-Fluoro-phenyl)-4a-methyl-1,4,4a,5,7,8-hexahydro-1,2,6-triaza-cyclopenta[b]naphthalene-6-sulfonyl]-benzonitrile;
(S)-1-(4-Fluoro-phenyl)-6-(4-methoxy-benzenesulfonyl)-4a-methyl-4,4a,5,6,7,8-hexahydro-1H-1,2,6-triaza-cyclopenta[b]naphthalene;
(S)-6-(4-Fluoro-benzenesulfonyl)-1-(4-fluoro-phenyl)-4a-methyl-4,4a,5,6,7,8-hexahydro-1H-1,2,6-triaza-cyclopenta[b]naphthalene;
(S)-6-(2-Fluoro-benzenesulfonyl)-1-(4-fluoro-phenyl)-4a-methyl-4,4a,5,6,7,8-hexahydro-1H-1,2,6-triaza-cyclopenta[b]naphthalene;
(S)-1-(4-Fluoro-phenyl)-4a-methyl-6-(toluene-2-sulfonyl)-4,4a,5,6,7,8-hexahydro-1H-1,2,6-triaza-cyclopenta[b]naphthalene;
4-[(S)-1-(4-Fluoro-phenyl)-4a-methyl-1,4,4a,5,7,8-hexahydro-1,2,6-triaza-cyclopenta[b]naphthalene-6-sulfonyl]-phenylamine;
(R)-6-(4-tert-Butyl-benzenesulfonyl)-1-(4-fluoro-phenyl)-1,4,5,6,7,8-hexahydro-1,2,6-triaza-cyclopenta[b]naphthalene-4a-carboxylic acid methyl ester;
[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-methanol;
[(R)-6-(4-Fluoro-benzenesulfonyl)-1-(4-fluoro-phenyl)-1,4,5,6,7,8-hexahydro-1,2,6-triaza-cyclopenta[b]naphthalen-4a-yl]-methanol;
[(R)-1-(4-Fluoro-phenyl)-6-(toluene-4-sulfonyl)-1,4,5,6,7,8-hexahydro-1,2,6-triaza-cyclopenta[b]naphthalen-4a-yl]-methanol;
[(R)-6-Benzenesulfonyl-1-(4-fluoro-phenyl)-1,4,5,6,7,8-hexahydro-1,2,6-triaza-cyclopenta[b]naphthalen-4a-yl]-methanol;
(R)-6-(4-tert-Butyl-benzenesulfonyl)-1-(4-fluoro-phenyl)-4a-methoxymethyl-4,4a,5,6,7,8-hexahydro-1H-1,2,6-triaza-cyclopenta[b]naphthalene;
(R)-6-(4-tert-Butyl-benzenesulfonyl)-1-(4-fluoro-phenyl)-4a-(2-methoxy-ethoxymethyl)-,6,7,8-hexahydro-1H-1,2,6-triaza-cyclopenta[b]naphthalene;
(R)-6-(Benzenesulfonyl)-1-(4-fluoro-phenyl)-4a-(2-hydroxy-ethoxymethyl)-4,4a,5,6,7,8-hexahydro-1H-1,2,6-triaza-cyclopenta[b]naphthalene;
(R)-6-(4-tert-Butyl-benzenesulfonyl)-4a-ethoxymethyl-1-(4-fluoro-phenyl)-4,4a,5,6,7,8-hexahydro-1H-1,2,6-triaza-cyclopenta[b]naphthalene;
(R)-6-(4-tert-Butyl-benzenesulfonyl)-1-(4-fluoro-phenyl)-4a-(3-methoxy-propoxymethyl)-4,4a,5,6,7,8-hexahydro-1H-1,2,6-triaza-cyclopenta[b]naphthalene;
3-[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethoxy]-propionitrile;
(R)-6-(4-tert-Butyl-benzenesulfonyl)-1-(4-fluoro-phenyl)-4a-(2-morpholin-4-yl-ethoxymethyl)-4,4a,5,6,7,8-hexahydro-1H-1,2,6-triaza-cyclopenta[b]naphthalene;
(R)-6-(4-tert-Butyl-benzenesulfonyl)-1-(4-fluoro-phenyl)-4a-(2-piperidin-1-yl-ethoxymethyl)-4,4a,5,6,7,8-hexahydro-1H-1,2,6-triaza-cyclopenta[b]naphthalene;
(R)-6-(4-tert-Butyl-benzenesulfonyl)-1-(4-fluoro-phenyl)-4a-(2-pyrrolidin-1-yl-ethoxymethyl)-4,4a,5,6,7,8-hexahydro-1H-1,2,6-triaza-cyclopenta[b]naphthalene;
(R)-6-(4-Fluoro-benzenesulfonyl)-1-(4-fluoro-phenyl)-4a-(2-methoxy-ethoxymethyl)-4,4a,5,6,7,8-hexahydro-1H-1,2,6-triaza-cyclopenta[b]naphthalene;
(R)-6-(4-Fluoro-benzenesulfonyl)-1-(4-fluoro-phenyl)-4a-methoxymethyl-4,4a,5,6,7,8-hexahydro-1H-1,2,6-triaza-cyclopenta[b]naphthalene;
(R)-1-(4-Fluoro-phenyl)-4a-methoxymethyl-6-(toluene-4-sulfonyl)-4,4a,5,6,7,8-hexahydro-1H-1,2,6-triaza-cyclopenta[b]naphthalene;
(R)-1-(4-Fluoro-phenyl)-4a-(2-methoxy-ethoxymethyl)-6-(toluene-4-sulfonyl)-4,4a,5,6,7,8-hexahydro-1H-1,2,6-triaza-cyclopenta[b]naphthalene;
(R)-6-Benzenesulfonyl-1-(4-fluoro-phenyl)-4a-(2-methoxy-ethoxymethyl)-4,4a,5,6,7,8-hexahydro-1H-1,2,6-triaza-cyclopenta[b]naphthalene;
(R)-6-Benzenesulfonyl-1-(4-fluoro-phenyl)-4a-methoxymethyl-4,4a,5,6,7,8-hexahydro-1H-1,2,6-triaza-cyclopenta[b]naphthalene;

(R)-6-(4-tert-Butyl-benzenesulfonyl)-1-(4-fluoro-phenyl)-1,4,5,6,7,8-hexahydro-1,2,6-triaza-cyclopenta[b]naphthalene-4a-carbaldehyde;

[(S)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethyl]-dimethyl-amine;

(S)-6-(4-tert-Butyl-benzenesulfonyl)-1-(4-fluoro-phenyl)-4a-morpholin-4-ylmethyl-4,4a,5,6,7,8-hexahydro-1H-1,2,6-triaza-cyclopenta[b]naphthalene;

(S)-6-(4-Trifluoromethyl-benzenesulfonyl)-1-(4-fluoro-phenyl)-4a-morpholin-4-ylmethyl-4,4a,5,6,7,8-hexahydro-1H-1,2,6-triaza-cyclopenta[b]naphthalene;

(S)-6-(4-tert-Butyl-benzenesulfonyl)-1-(4-fluoro-phenyl)-4a-pyrrolidin-1-ylmethyl-4,4a,5,6,7,8-hexahydro-1H-1,2,6-triaza-cyclopenta[b]naphthalene;

([(S)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethyl]-ethyl-amine;

[(S)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethyl]-diethyl-amine;

(S)-6-(4-tert-Butyl-benzenesulfonyl)-1-(4-fluoro-phenyl)-4a-piperidin-1-ylmethyl-4,4a,5,6,7,8-hexahydro-1H-1,2,6-triaza-cyclopenta[b]naphthalene; [(S)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethyl]-(2-methoxy-ethyl)-amine;

(S)-6-(4-tert-Butyl-benzenesulfonyl)-1-(4-fluoro-phenyl)-4a-(4-methyl-piperazin-1-ylmethyl)-4,4a,5,6,7,8-hexahydro-1H-1,2,6-triaza-cyclopenta[b]naphthalene;

N'-[(S)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethyl]-N,N-dimethyl-ethane-1,2-diamine;

N-[(S)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethyl]-N,N',N'-trimethyl-ethane-1,2-diamine;

N'-[(S)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethyl]-N,N-dimethyl-propane-1,3-diamine;

N-[(S)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethyl]-N,N',N'-trimethyl-propane-1,3-diamine;

[(S)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethyl]-(2-methoxy-ethyl)-methyl-amine;

[(S)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethyl]-isopropyl-amine;

(S)-4a-Azetidin-1-ylmethyl-6-(4-tert-butyl-benzenesulfonyl)-1-(4-fluoro-phenyl)-4,4a,5,6,7,8-hexahydro-1H-1,2,6-triaza-cyclopenta[b]naphthalene;

Allyl-[(S)-6-(4-tert-butyl-benzenesulfonyl)-1-(4-fluoro-phenyl)-1,4,5,6,7,8-hexahydro-1,2,6-triaza-cyclopenta[b]naphthalen-4a-ylmethyl]-amine;

2-{[(S)-6-(4-tert-Butyl-benzenesulfonyl)-1-(4-fluoro-phenyl)-1,4,5,6,7-8-hexahydro-1,2,6-triaza-cyclopenta[b]naphthalen-4a-ylmethyl]-amino}-ethanol;

[(S)-1-(4-Fluoro-phenyl)-6-(toluene-4-sulfonyl)-1,4,5,6,7,8-hexahydro-1,2,6-triaza-cyclopenta[b]naphthalen-4a-ylmethyl]-dimethyl-amine;

(S)-1-(4-Fluoro-phenyl)-4a-pyrrolidin-1-ylmethyl-6-(toluene-4-sulfonyl)-4,4a,5,6,7,8-hexahydro-1H-1,2,6-triaza-cyclopenta[b]naphthalene; [(S)-6-(4-Fluoro-benzenesulfonyl)-1-(4-fluoro-phenyl)-1,4,5,6,7,8-hexahydro-1,2,6-triaza-cyclopenta[b]naphthalen-4a-ylmethyl]-dimethyl-amine;

(S)-6-(4-Fluoro-benzenesulfonyl)-1-(4-fluoro-phenyl)-4a-pyrrolidin-1-ylmethyl-4,4a,5,6,7,8-hexahydro-1H-1,2,6-triaza-cyclopenta[b]naphthalene;

(S)-6-Benzenesulfonyl-1-(4-fluoro-phenyl)-4a-pyrrolidin-1-ylmethyl-4,4a,5,6,7,8-hexahydro-1H-1,2,6-triaza-cyclopenta[b]naphthalene;

(S)-6-Benzenesulfonyl-1-(4-fluoro-phenyl)-1,4,5,6,7,8-hexahydro-1,2,6-triaza-cyclopenta[b]naphthalen-4a-ylmethyl]-dimethyl-amine;

(S)-6-Benzenesulfonyl-1-(4-fluoro-phenyl)-4a-morpholin-4-ylmethyl-4,4a,5,6,7,8-hexahydro-1H-1,2,6-triaza-cyclopenta[b]naphthalene;

2-{[(S)-6-(4-tert-Butyl-benzenesulfonyl)-1-(4-fluoro-phenyl)-1,4,5,6,7,8-hexahydro-1,2,6-triaza-cyclopenta[b]naphthalen-4a-ylmethyl]-methyl-amino}-ethanol;

4-[(S)-1-(4-Fluoro-phenyl)-4a-morpholin-4-ylmethyl-1,4,4a,5,7,8-hexahydro-1,2,6-triaza-cyclopenta[b]naphthalene-6-sulfonyl]-benzonitrile;

[(S)-6-Benzenesulfonyl-1-(4-fluoro-phenyl)-1,4,5,6,7,8-hexahydro-1,2,6-triaza-cyclopenta[b]naphthalen-4a-ylmethyl]-diethyl-amine;

Diethyl-[(S)-1-(4-fluoro-phenyl)-6-(4-methoxy-benzenesulfonyl)-1,4,5,6,7,8-hexahydro-1,2,6-triaza-cyclopenta[b]naphthalen-4a-ylmethyl]-amine;

(S)-6-Benzenesulfonyl-1-(4-fluoro-phenyl)-4a-piperidin-1-ylmethyl-4,4a,5,6,7,8-hexahydro-1H-1,2,6-triaza-cyclopenta[b]naphthalene;

(S)-1-(4-Fluoro-phenyl)-6-(4-methoxy-benzenesulfonyl)-4a-piperidin-1-ylmethyl-4,4a,5,6,7,8-hexahydro-1H-1,2,6-triaza-cyclopenta[b]naphthalene;

(S)-1-(4-Fluoro-phenyl)-4a-morpholin-4-ylmethyl-6-(toluene-2-sulfonyl)-4,4a,5,6,7,8-hexahydro-1H-1,2,6-triaza-cyclopenta[b]naphthalene;

(S)-6-(2-Fluoro-benzenesulfonyl)-1-(4-fluoro-phenyl)-4a-morpholin-4-ylmethyl-4,4a,5,6,7,8-hexahydro-1H-1,2,6-triaza-cyclopenta[b]naphthalene;

(R)-6-(4-tert-Butyl-benzenesulfonyl)-1-(4-fluoro-phenyl)-1,4,5,6,7,8-hexahydro-1,2,6-triaza-cyclopenta[b]naphthalene-4a-carboxylic acid;

(R)-6-(4-tert-Butyl-benzenesulfonyl)-1-(4-fluoro-phenyl)-1,4,5,6,7,8-hexahydro-1,2,6-triaza-cyclopenta[b]naphthalene-4a-carboxylic acid benzylamide;

[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-morpholin-4-yl-methanone;

[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-piperidin-1-yl-methanone;

[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-pyrrolidin-1-yl-methanone;

(R)-6-(4-tert-Butyl-benzenesulfonyl)-1-(4-fluoro-phenyl)-1,4,5,6,7,8-hexahydro-1,2,6-triaza-cyclopenta[b]naphthalene-4a-carboxylic acid ethylamide;

(R)-6-(4-tert-Butyl-benzenesulfonyl)-1-(4-fluoro-phenyl)-1,4,5,6,7,8-hexahydro-1,2,6-triaza-cyclopenta[b]naphthalene-4a-carboxylic acid dimethylamide;

1-[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-ethanol;

1-[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-propan-1-ol;

[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-acetic acid methyl ester;

2-[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-ethanol;

(R)-6-(4-tert-Butyl-benzenesulfonyl)-1-(4-fluoro-phenyl)-4a-(2-methoxy-ethyl)-4,4a,5,6,7,8-hexahydro-1H-1,2,6-triaza-cyclopenta[b]naphthalene;

{2-[(R)-6-(4-tert-Butyl-benzenesulfonyl)-1-(4-fluoro-phenyl)-1,4,5,6,7,8-hexahydro-1,2,6-triaza-cyclopenta[b]naphthalen-4a-yl]-ethyl}-dimethylamine;

(R)-6-(4-tert-Butyl-benzenesulfonyl)-1-(4-fluoro-phenyl)-4a-(2-pyrrolidin-1-yl-ethyl)-4,4a,5,6,7,8-hexahydro-1H-1,2,6-triaza-cyclopenta[b]naphthalene; and (4aS,8aS)-6-(4-tert-Butyl-benzenesulfonyl)-1-(4-fluoro-phenyl)-4a-morpholin-4-ylmethyl-4,4a,5,6,7,8,8a,9-octahydro-1H-1,2,6-triazacyclopenta[b]naphthalene.

* * * * *